US009468560B1

United States Patent
Daneshvar

(10) Patent No.: US 9,468,560 B1
(45) Date of Patent: Oct. 18, 2016

(54) DANESHVAR SUPPORT UNITS MICRO AND METHODS

(76) Inventor: Yousef Daneshvar, West Bloomfield, MI (US)

(*) Notice: Subject to any disclaimer, the term of this patent is extended or adjusted under 35 U.S.C. 154(b) by 0 days.

(21) Appl. No.: 13/136,604

(22) Filed: Aug. 8, 2011

Related U.S. Application Data

(63) Continuation of application No. 12/931,694, filed on Feb. 8, 2011, now Pat. No. 8,764,694, which is a continuation of application No. 10/356,040, filed on Jan. 31, 2003, now Pat. No. 7,901,372, application No. 13/136,604, which is a continuation of application No. 10/330,732, filed on Dec. 28, 2002, now Pat. No. 8,469,912, application No. 13/136,604, which is a continuation of application No. 11/648,944, filed on Jan. 3, 2007, now Pat. No. 8,556,841, and a continuation of application No. 11/704,635, filed on Feb. 9, 2007, application No. 13/136,604, which is a continuation of application No. 11/648,944, filed on Jan. 3, 2007, now Pat. No. 8,556,841, application No. 13/136,604, which is a continuation of application No. 11/704,635, filed on Feb. 9, 2007.

(60) Provisional application No. 60/355,550, filed on Feb. 7, 2002, provisional application No. 60/771,819, filed on Feb. 10, 2006, provisional application No. 60/755,269, filed on Jan. 3, 2006, provisional application No. 60/345,551, filed on Jan. 7, 2002.

(51) Int. Cl.
*A61F 13/00* (2006.01)
*A61F 13/08* (2006.01)
*A61F 5/01* (2006.01)

(52) U.S. Cl.
CPC ......... *A61F 13/00038* (2013.01); *A61F 13/08* (2013.01); *A61F 5/01* (2013.01)

(58) Field of Classification Search
USPC ........... 602/60–64, 74–76, 79; 128/882, 888, 128/889; 606/201–204
See application file for complete search history.

(56) References Cited

U.S. PATENT DOCUMENTS

| | | | |
|---|---|---|---|
| 4,088,136 A * | 5/1978 | Hasslinger et al. | 604/179 |
| 4,149,540 A * | 4/1979 | Hasslinger | A61B 17/1322 128/DIG. 15 |
| 4,215,687 A | 8/1980 | Shaw | |
| 4,556,055 A * | 12/1985 | Bonner, Jr. | A61F 7/10 128/DIG. 15 |
| 4,991,234 A * | 2/1991 | Greenberg | A41D 20/00 2/16 |
| 5,113,877 A | 5/1992 | Johnson, Jr. et al. | |
| 5,248,292 A * | 9/1993 | Holland | A61F 5/05841 602/20 |
| 5,779,657 A * | 7/1998 | Daneshvar | 602/60 |

* cited by examiner

*Primary Examiner* — Kim M Lewis

(57) ABSTRACT

A wrap for encircling a portion of a living body having a strap of stretchable material allowing the strap to stretch along its length and having inner and outer surfaces of loop attachment material. The strap has a zone of hook attachment material disposed on the inner surface at a location along the length of the strap which provides for detachable/reattachable attachment of the hook attachment material to the loop attachment material of the outer surface. The strap further has a zone of hook attachment material on the outer surface of the strap at a location along the length of the strap which provides for detachable/reattachable attachment of the hook attachment material disposed on the outer surface of the strap to the loop attachment material of the inner surface.

18 Claims, 33 Drawing Sheets

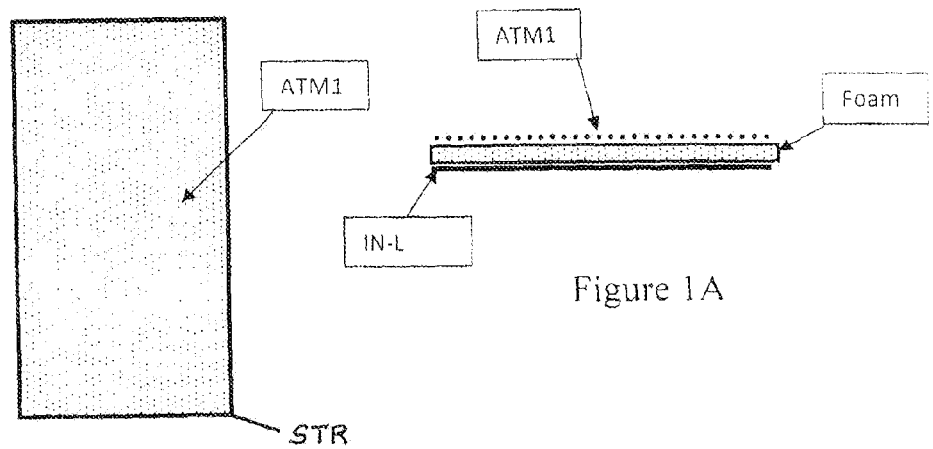
Figure 1A
Figure 1C
Figure 1
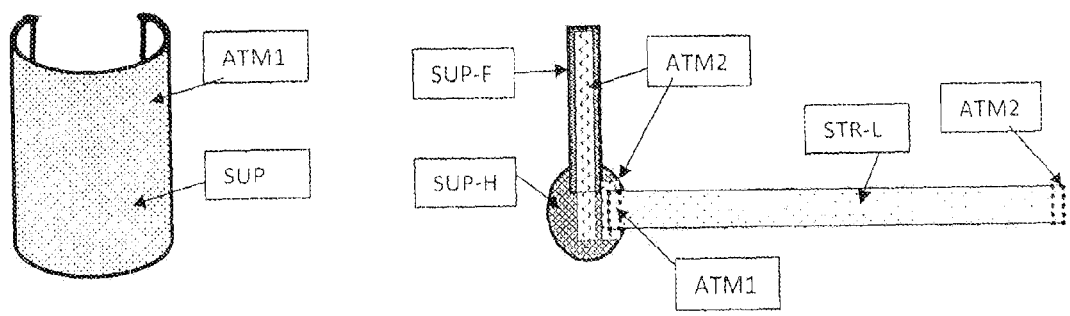
Figure 1B
Figure 1 CD

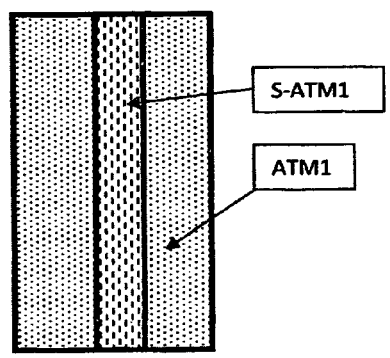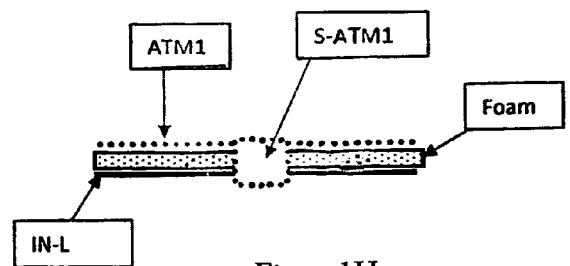
Figure 1G
Figure 1H

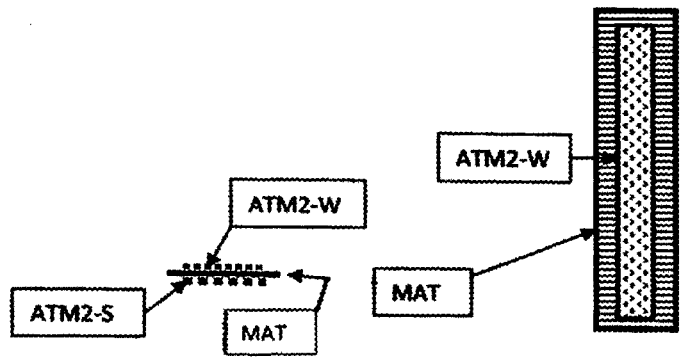
Figure 2A  Figure 2
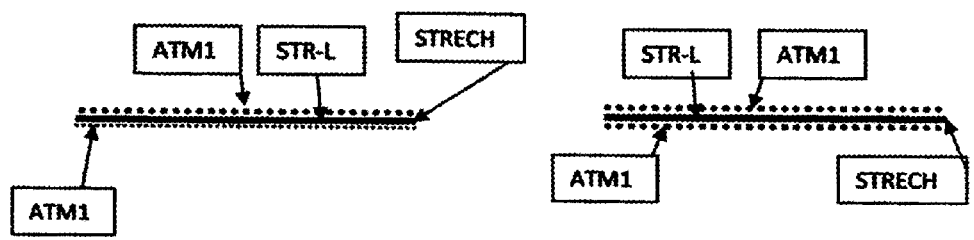
Figure 3  Figure 3A
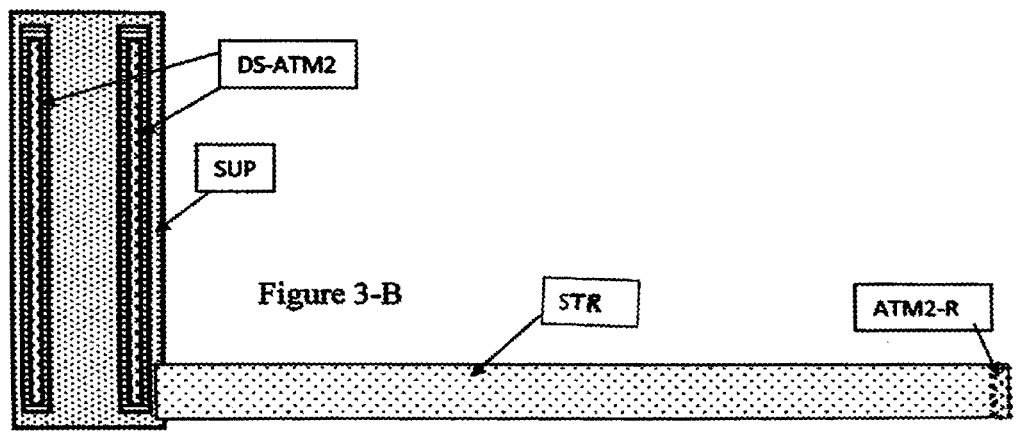
Figure 3-B

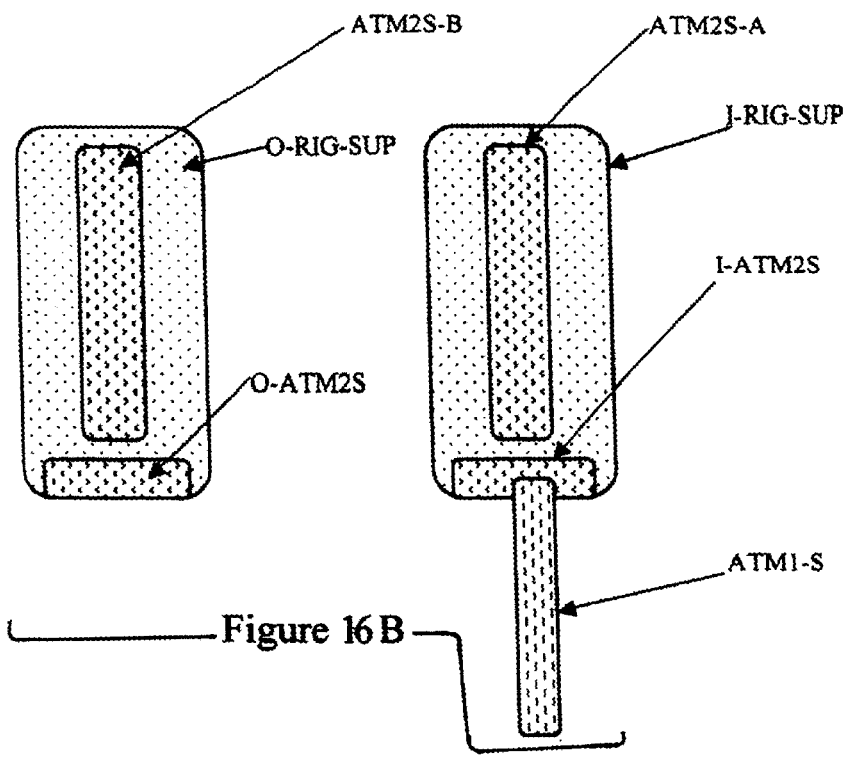
Figure 16B
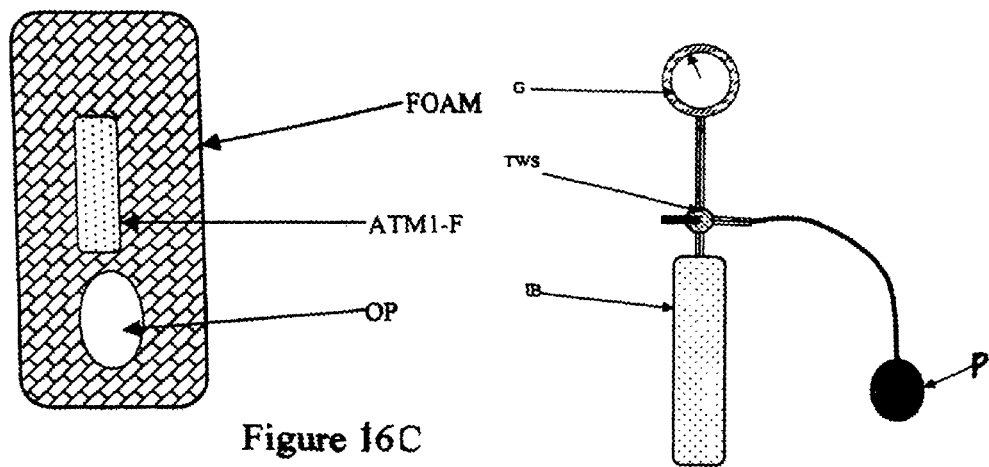
Figure 16C
Figure 16D

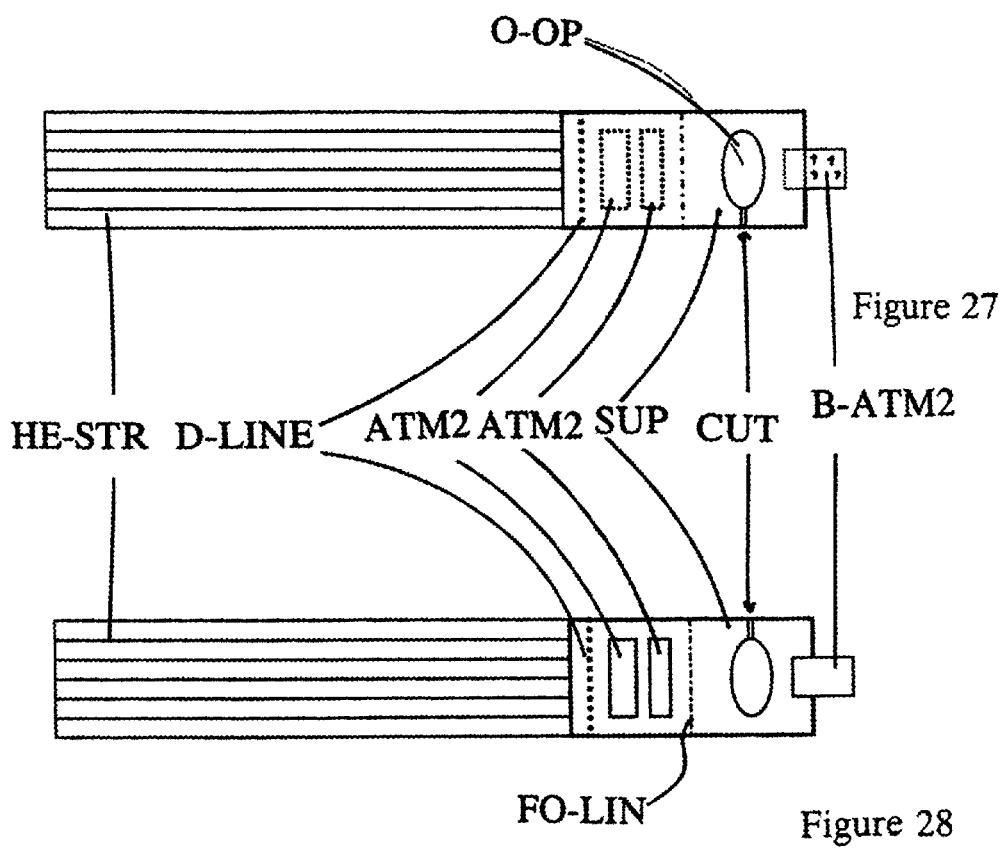
Figure 27
Figure 28
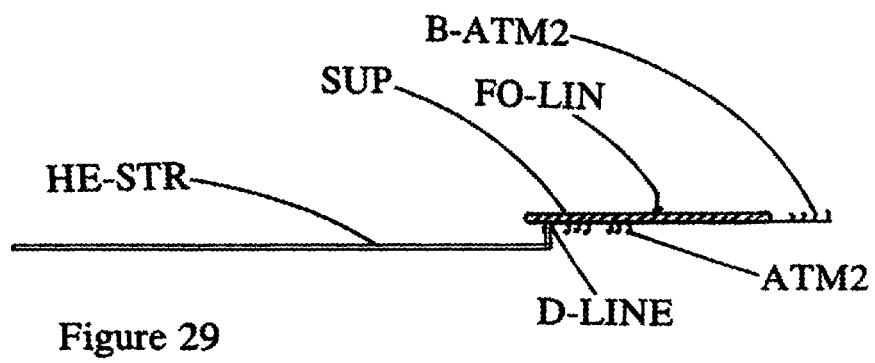
Figure 29

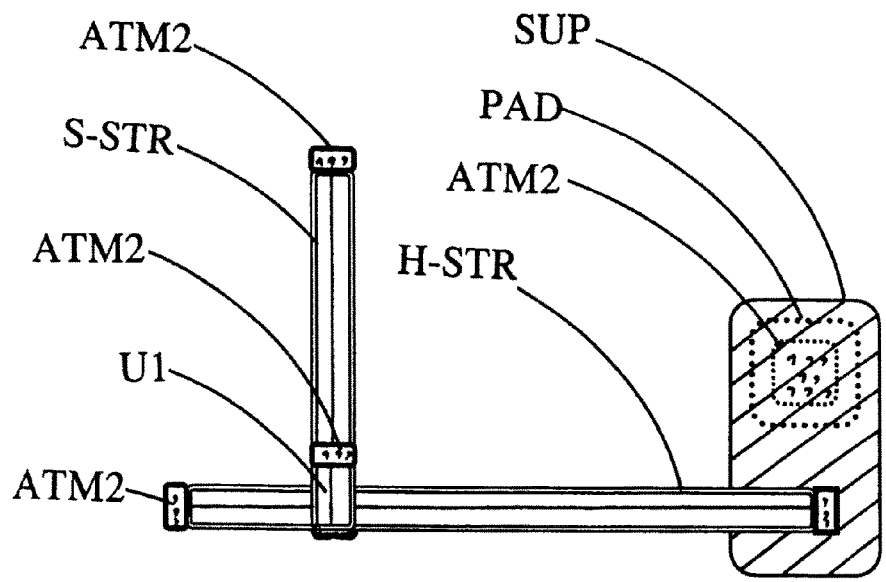
Figure 30
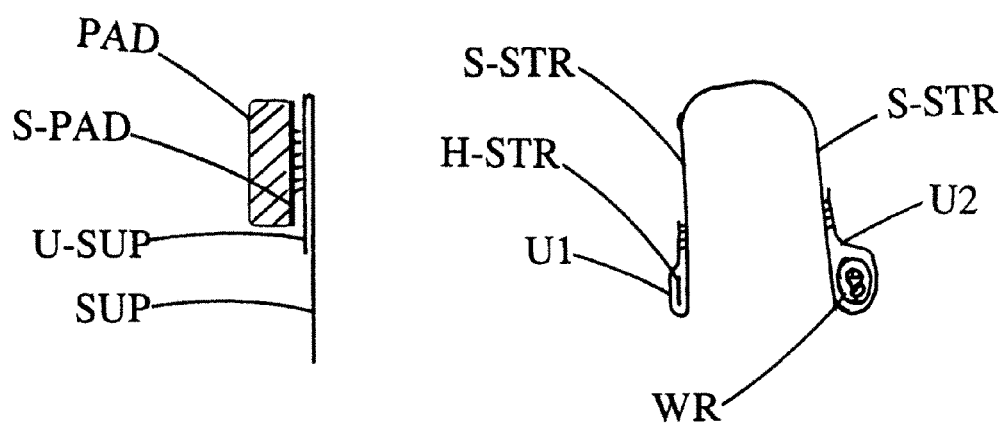
Figure 31
Figure 31A

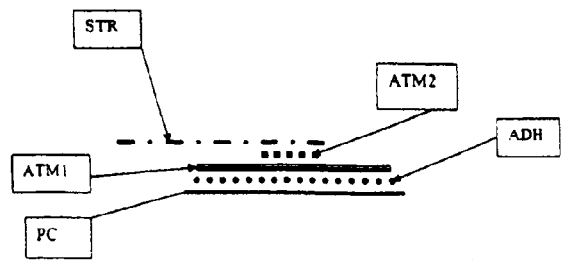
FIGURE 37
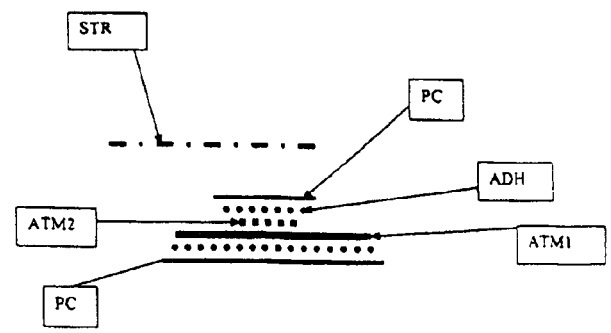
Figure 37A
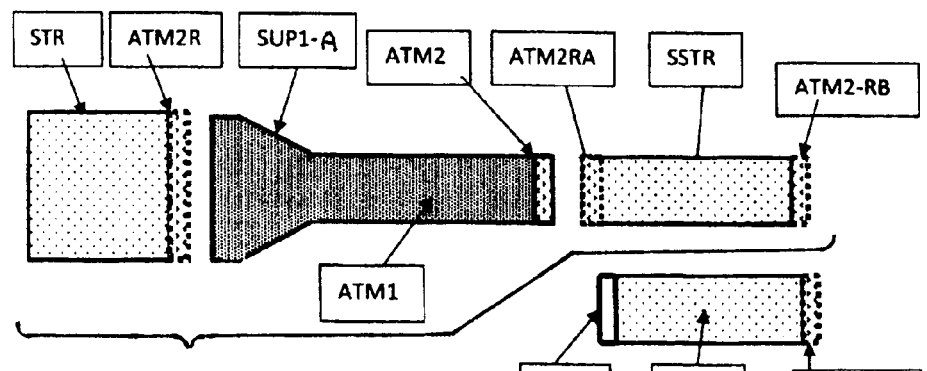
FIGURE 38
FIGURE 40
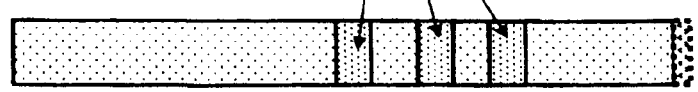
FIGURE 39

DANESHVAR SUPPORT UNITS MICRO AND METHODS

This application is a continuation, and claims priority, of: 1) currently application Ser. No. 12/931,694, filing date Feb. 8, 2011, now U.S. Pat. No. 8,765,694 with the title of invention: Daneshvar Wound Managing, System and Methods, which is a continuation of application Ser. No. 10/356,040, filing date Jan. 31, 2003 with the title of invention: Daneshvar Wound Dressing, support Units and Methods, now U.S. Pat. No. 7,901,372 issued Mar. 8, 2011, which is a non-provisional of provisional application No. 60/345,551, filing date Jan. 7, 2002, and of provisional application No. 60/355,550, filing date Feb. 7, 2002; 2) currently pending application Ser. No. 10/330,732, filing date Dec. 28, 2002 with the title of invention: Daneshvar Wound Dressing, support Units and Methods. Model Daphne, which is a non-provisional of provisional application No. 60/345,551, filing date Jan. 7, 2002, and of provisional application No. 60/355,550, filing date Feb. 7, 2002; 3) currently application Ser. No. 11/648,944, filing date Jan. 3, 2007 now U.S. Pat. No. 8,556,841 with the title of invention: Daneshvar Wrapping Means and Methods, which is a non-provisional of provisional application No. 60/755,269, filing date Jan. 3, 2006; and 4) currently pending application Ser. No. 11/704,635, filing date Feb. 9, 2007 with the title of invention: DANESHVAR Wrapping means II AND METHODS, which is a non-provisional of provisional application No. 60/771,819, filing date Feb. 10, 2006.

THE BACKGROUND OF THIS INVENTION

This invention is related to wound dressings and supports in humans and animals. Commonly, adhesives and wraps are used for this purpose. However, the use of adhesives has multiple problems: they are difficult to use with elastic gloves since adhesive tapes adhere to the gloves, they cause skin irritations and discomfort on removal, and do not adhere to hair-covered skin. Many times the hair has to be shaved, which is a separate process of its own. Wound inspections or the exchange of dressing multiplies their problems and prohibits this process and many other problems. Therefore this applicant has introduced a new means of wound support and dressings and now wishes to introduce some more new models and means which has its own merits.

THE BRIEF EXPLANATION OF THE INVENTION

Considering the above mentioned issues, this applicant has spent years and years and introduced a new means of wound support and dressings in the past and now introduces more new models and means which have their own merits. This application introduces a support unit made from a non-stretchable material, commonly rectangular- or trapezoid-in shape, with an outside surface covered with loop fastener attachment means which is designed for placement on a limb or other part of a body. The support is attached to a stretchable strap means with an end piece consisting of an attachment means which is capable of attaching to the outside of the support on a detachable, re-attachable basis. The applicant shows in this application how these support means can be shaped differently in order to make units for use by compromised patients such as elderly, wounded or with neuromuscular problems. Importantly, the applicant also shows how his previous inventions can be modified to make multiple simpler units so that the wound care for humans and animals would be much simpler, easier and adjustable. By doing so he hopes to achieve part of his goal of many years in helping humans in a large scale.

BRIEF EXPLANATION OF THE FIGURES

FIG. 1. Shows front view of a support, with a surface covered with loop fastener attachment means.

FIG. 1A. Shows the cross cut view of a support unit shown in FIG. 1.

FIG. 1B. Shows a shaped support in the shape of half of a cylinder.

FIG. 1C. Shows a shaped spring for shaping the support shown at FIG. 1.

FIG. 1CD. Shows front view of a splint/shaped support unit, made from two pieces with of strap.

FIG. 1G. Shows a zones of none stretchable support with zone of stretchable part.

FIG. 1H: Shows a cross-cut view of FIG. 1G.

FIG. 2. Shows the front view of a double sided, hook fastener attachment means, DS-ATM2.

FIG. 2A. Shows the cross cut view of the DS-ATM2 shown in FIG. 1.

FIG. 3. Shows cross cut of a stretchable fabric which functions as ATM1, more in one side.

FIG. 3A. Shows cross cut of a stretchable fabric which functions as ATM1 in both sides.

FIG. 3B. Shows a support, with 2, DS-ATM2, attached to it and a strap.

FIG. 7AB shows a stretchable strap with both surfaces that functions as ATM1.

FIG. 7CA shows the side view of the unit shown at FIG. 7C.

FIG. 16A shows front of a support unit for the ankle area.

FIG. 16B shows side views of rigid pieces for use with the U-shaped extension for the leg support.

FIG. 16C shows a foam, FOAM, designed for use with the unit shown at previous FIG. 16B.

FIG. 16D shows an inflation balloon, IB, with a gauge, G for use with the unit for the leg.

FIG. 18B shows a strap means for use with the unit shown at FIG. 18 which goes around the head.

FIG. 22 A shows the side view of the unit shown at FIG. 22 placed in the lower leg.

FIGS. 27-28 show the front and the rear view of a support means for the ear.

FIG. 29 shows the side view of the support means for the ear.

FIG. 30 shows a support means for the Pacemaker-Defibrillator Wound.

FIG. 31 shows the side view of a support means shown in previous FIG. 30.

FIG. 31A shows the side view of the arrangement of the straps for the unit shown at FIG. 31.

FIG. 37 shows lower surface of ATM1, which has an adhesive, ADH, a strap with ATM2 attached.

FIG. 37A shows the side view of a unit similar to FIG. 37 with modification.

FIG. 38 Shows front view of a strap-support, means for attaching to the end of a strap means.

FIG. 39. Shows strap means with zones of ATM1 on its front surface.

FIG. 40 shows a modification for a part of FIG. 38.

DETAILED EXPLANATION OF THE FIGURES

Figure 1D:
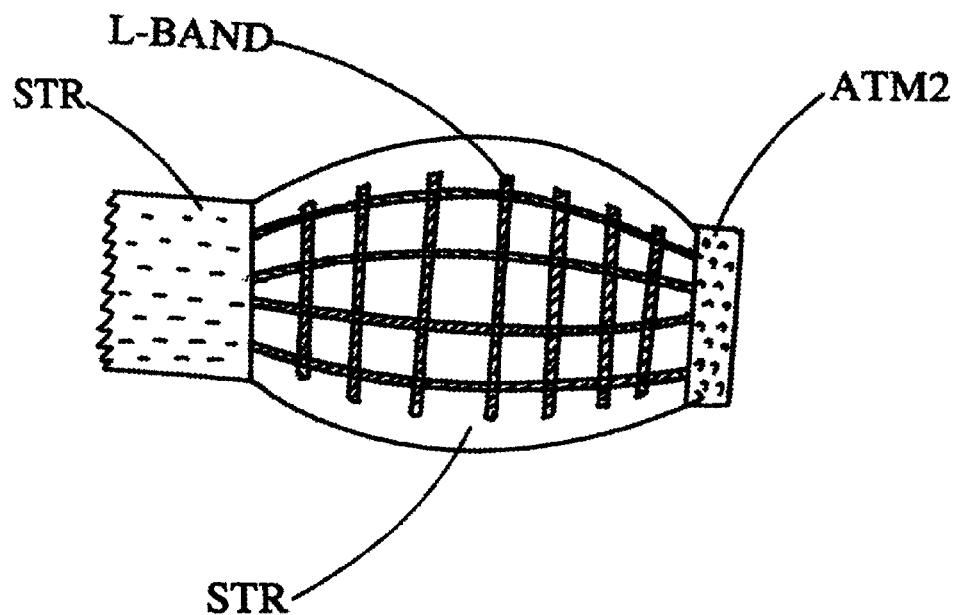
FIG. 1D. Shows front view of a stretchable support unit, with zone of stretchable material in it.

With regard to the figures: Please notice that different parts of this invention are shown in different figures. This is to prevent a crowded picture. Importantly, many of the options are designed to be used in one model or more when applicable.

FIG. 1 shows a support means SUP made from a non-stretchable fabric with an outside surface covered by, or functioning as, loop fastener attachment means, i.e. loop fastener attachment material, here shown at ATM1. This support stands away from the skin of the user and this allows the end of the strap means, such as one shown at STR-L at FIG. 4C, with a zone of hook fastener attachment means ATM2 to attach to any part of the outer surface of this support on a detachable, re-attachable basis. A more common form of this support is made from a laminar material, consisting of three layers, an inner layer, shown in FIGS. 1 and 1A. In FIGS. 1 and 1A the outer layer shown at ATM1 is made from a loop fastener attachment means and the support means has an inner lining, In-L, which is a soft fabric that will stand on skin. The support means also has a layer of foam in between these two layers ATM1 and In-L, shown at FIG. 1A.

In FIG. 1 the general shape of the support means, is a rectangular piece, covered with a loop fastening attachment means, ATM1. This unit will have strap/s attached to it in one side which will be pulled and attached to the outer surface of the support.

FIG. 1A shows the cross cut view of the unit shown in FIG. 1 and the upper surface of the support which is a loop fastener attachment means shown at ATM1 and the inner soft layer of fabric at IN-L and a layer of foam FOAM in between.

FIG. 1B shows an example of a shaped support. In this model the support has the shape of half of a cylinder, and has a spring body that can stretch and coil. In some models it may also have a memory so that the support can be easily shaped to be placed on forearm, arm or leg with a reasonable steadiness. This unit will have straps attached to it in one side which will be pulled and attached to the outer surface of the support. The outer surface of this support is covered with a layer of loop fastener attachment means, ATM1, and allows the ends of the straps with ATM2 to be attached to it, Thus such a shaped support will make the placement of such units in these areas much easier. To understand this importance consider a wounded person or a person with neuromuscular problems or an aged person who has difficulty placing and keeping of a flat support on his/her limb. This model of the support means makes the placement a lot easier, since it will stand in the areas with the first placement and will allow the straps to be attached. Note in this figure the straps are not shown but they will be attached to the border of the support as shown in figures such as FIGS. 4, 4A and 4B.

Importantly, the means that gives shapes to the body of the supports may even be a detachable piece/s of a spring or metal. In this case it can be a semi-ring or similar that can be attached to a layer of a support on a detachable re-attachable basis. One, two, or more pieces of these units, or a longer piece, can be attached to the outside of the supports or to the inner part of the support for doing the job. Such units may have different make-ups and shapes for serving the purpose. A model of this is shown at FIG. 1C.

Importantly, the unit shown at FIG. 1B may be also used to protect the underlying tissue from incoming objects when the body of the support is more protective, and thus these units would be very useful in patients who have tendency for bumping their shins against objects, such as elderly or patients with neuromuscular problems who have a limb that needs to be protected from incoming objects. They can even be used as a splint.

FIG. 1C shows a spring means designed to attach to a flat support for giving a shape. This unit is made in the shape of a semi-ring, and is capable of being attached to the outer or the inner surface of a flat support means in order to make it into a semi-cylindrical shape. One, two, or more pieces of these units, or a longer piece, can be attached to the outside or the inner surface of a support to make them the desired shape. They may have many make-ups or shapes for serving the purpose. This piece may be attached to the support means on a detachable re-attachable basis, by use of snaps, fastener means, adhesives etc. Importantly, it can be part of the skeleton of the support for doing the job. Importantly, the size, shape, the material used, the thickness and other important variables of such skeletons may vary to allow different units to be made for different uses.

FIG. 1CD shows schematically the rear surface of a shaped support, which has a relatively rigid body composed of two pieces, SUP-F, to be placed in the forearm, and SUP-H, for placement on the back of the hand, which are attached to each other on detachable, re-attachable basis. The lower piece of this support, SUP-H has a body with curvature such as a large spoon or spade. The upper piece, SUP-F has a long rectangular shape almost like a handle of a spoon, except with a curve to fit the elbow. The two pieces are attached to each other to make a unit in the shape of a large spoon or spade with curvatures to stand in the posterior surface of forearm and hand and function as a splint. The support has a long zone of hook fastener attachment means, i.e. hook fastener attachment material, shown at ATM2 on the rear surface of the SUP-F and SUP-H. Also attached to the support is a long strap shown at STR-L, made from a stretchable, loop fastener attachment means with ATM1 zone on the rear surface of its first end and hook fastener attachment means ATM2 on the rear surface of its second end so that the first end with ATM1 will attach to the outer surface of the body of support, SUP-H and can wrap around the support obliquely and move up wrapping to hold the support around the hand and the elbow securely, and the second end will attach to the outer surface of the strap itself. The advantages of this unit are many: they allow the size of the handle and main body of this support to be changed, since the hands of people have different sizes, or the needed padding may have different sizes. Having a model for everybody in hospital or emergency center is not possible or will be costly, however, this model allows two pieces of different sizes to be attached to each other for making a unit that would fit a given case it is very light it is very easy to handle and can be packed compactly to be carried by users for potential circumstance, such as going to the woods, mountains, bike riding and in army. Note, the two pieces of the supports may be attached to each other by use of attachment means on a detachable re-attachable basis, as shown in FIG. 1CD where the lower end of the support SUP-F is attached to the rear surface of the support SUP-H by use of ATM2. It should be noted that the support may also be used with more than one strap as shown in the units in FIG. 16 for the leg or in FIGS. 14 and 15 for the units for the arm and thigh. Advantages of the units with multiple straps allow each strap to be easily adjusted, which is very important.

FIG. 1D shows an example of another shaped support, as well as a stretchable support. In this model the front of a special stretchable support unit is made from shaping the material used for the strap or Lycra™. Here, the Lycra™ is modified with use of bands made from materials such as latex, silicon or similar as shown at L-BAND. The shaping of this stretchable material or the use of sewing or other techniques allows a stretchable, shaped support to be made. Such a support will be very useful in areas with a Particular shape and function such as knees, ankles, elbows, toes, head etc. Such a shaped, stretchable support allows better handling and placement of these units in certain cases. In this figure the attachment means of the support is shown at ATM2 and the strap at STR. A D-Ring may also allow the strap to be adjusted. Note the strap made of Lycra™ will wrap and attach to the ATM2. The support may be made to be shaped but non-stretchable.

The following advantages are to be noted:

a. When the support has a stretchable body it can be pulled to keep the area under tension and provide pressure to underlying tissue when needed. This is advantageous in conditions where compression is needed.

b. The support unit stretches and conforms and accepts the shape of the area. Also, such a body allows this body of the support to change with change of the wound areas such as over joints, knees, ankles, hips, elbows with extension and closure.

c. The inner part of the support will be a soft, non-irritant fabric and does not cause skin reaction.

d. On the scalp and other areas it will allow an easy dressing of the wound.

e. Importantly, the side where the strap is attached stretches in both direction and allows this unit to fit a shaped area, such as the scalp. A transverse strap allows this unit to be further stable on the scalp and will make a cross-shaped stable unit.

Figure 1E:
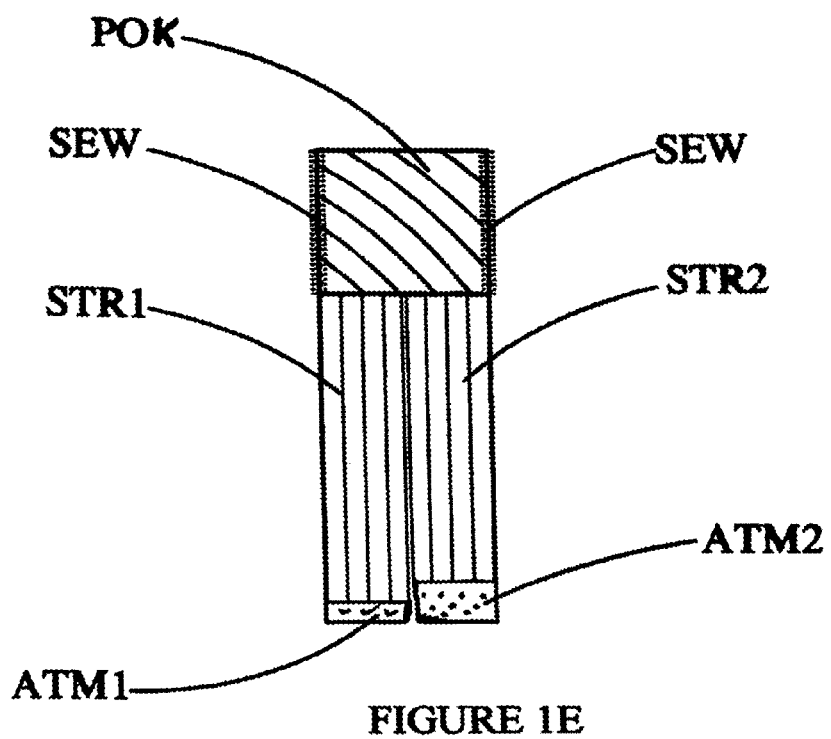
FIG. 1E. Shows a support unit in shape of a pocket with two straps attached.

FIG. 1E schematically the general view of yet another shaped support for dressing the toes. This unit has a support in the shape of a pocket, POK, made from a combination of a front and rear wall attached to each other along their borders, as shown in lines, SEW. In this particular model, the fabric is folded so the front border is closed as well. The rear wall of this unit has two stretchable straps, STR-1 and STR-2, made from Lycra™ and is attached to the body of the rear wall. The free ends of these straps have a complementary attachment means made from loop-fastener attachment means, ATM1, and hook-fastener attachment means, ATM2, respectively. Importantly, please note that one of the attachment means will be in front of one of the straps and the other will be on the rear surface of the other strap. This method will allow the end of these straps to attach to each other on a detachable, re-attachable basis.

Figure 1F:
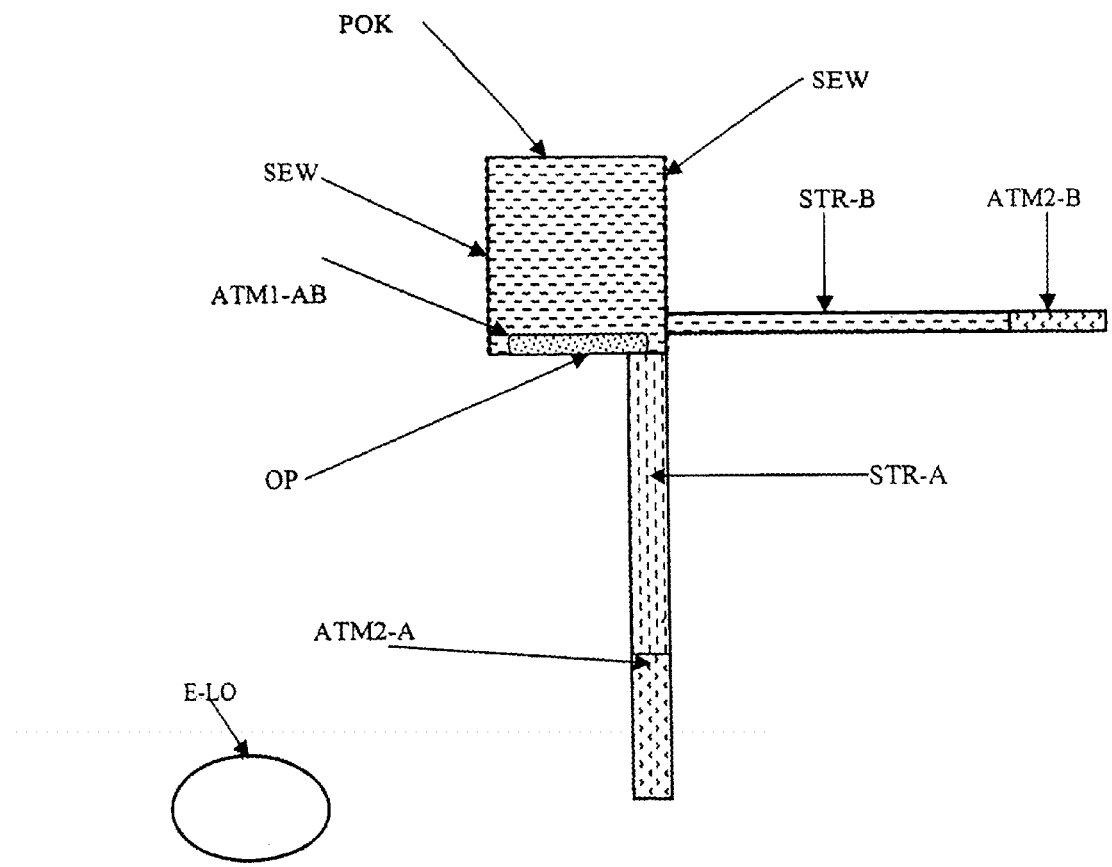
FIG. 1F. Shows another pocket shaped support with straps in different directions.

FIG. 1F. Shows schematically, the general view of a support unit similar to the unit shown at FIG. 1E, except that the two bands or the straps of this unit, strap, STR-A, and strap, STR-B are placed in different directions. This unit also has a pocket, POK, made from a folded layer of a stretchable fabric, particularly, LYCRA™ whose sides are sewn or attached together along the lines, SEW. The outer/top surface of this pocket, POK has a zone of loop fastener, attachment means, ATM1-AB. The rear/bottom surface of the pocket, POK, has one elastic strap, STR-A made from LYCRA™ attached to it. The free end of the strap, STR-A, has a zone of loop-fastener, attachment means, ATM2-A, that allows this strap to wrap around the ankle and attach to the attachment means, ATM1-AB of the top of the pocket, POK. Importantly, when the body of the pocket is made from LYCRA™ then the ATM2-A, of the strap, STR-A, will attach to the outer surface of the pocket, POK, on a detachable, re-attachable basis.

The unit may have another elastic strap, STR-B, made from LYCRA™ that wraps around the base of the pocket, POK, and attaches to the loop-fastener, attachment means, ATM1-AB or the body of the pocket, POK, on a detachable, re-attachable basis. The function of the strap, STR-B, is to hold the base of the pocket together if there is a need for it.

FIGS. 2 and 2A show the front and cross cut view of a unit referred to by this applicant as a double sided hook fastener attachment means This unit has a flat body a matrix shown at MAT with zones of hook fastener attachment means ATM2 on both sides so that combination makes a flat body with ATM2 on both sides. When the matrix is cuttable, this unit can be cut to pieces of various shapes and be attached to the surface of the support, SUP (not shown) on a detachable, re-attachable attachment basis, when such support is made with an outer surface made from loop fastener attachment means. Importantly, the makeup of the matrix may vary; it can be made of a fabric, adhesive layer, PVCs, metal or similar. It may be made to flex or shape, to have a memory, or may be made to be a relatively rigid and not to shrink or easily bend. Or the matrix may have any other consistency or construction which is needed for special use. The strength or the degree of attachability of the zones of hook fastener attachment means ATM2 may also vary to make them weaker or stronger to attach, so that the attachments of these to the support can be stronger and to the straps weaker. In this figure the matrix is shown at MAT, and the weaker hook fastener attachment means at ATM2-W and the stronger hook fastener attachment means at ATM2-S. Thus when this particular piece is attached to the support and strap at the same time by attaching the stronger hook fastener attachment means, ATM2-S to the support and the weaker hook fastener attachment means at ATM2-W to the strap, the strap will be detached from the ATM2-W but the ATM2-S will still be attached to the support when the strap is pulled away. These Pieces may be also made like a cylinder with an outer surface made of ATM2 that can roll on the surface of the support means made of ATM1, but still will be attached to the support on a detachable, re-attachable basis.

FIG. 3 shows the cross cut view of a stretchable fabric, STR-L which has an upper surface that functions as loop fastener attachment means ATM1. In this figure, the body of the stretchable fabric is shown schematically at STRECH, and the upper surface of the strap which has capability of functioning as loop fastener attachment means is shown at ATM1. Also importantly, the lower surface of this strap, shown with smaller dotted line, has the same capability to function as ATM1 and attaching to ATM2, however it is less potent in doing so than the upper surface. Thus in practice both sides of this strap attach to ATM2. The applicant refers to this model of strap as STR-L, and he means that both sides of this stretchable fabric have the capability of attaching to ATM2, since technically they are. Importantly, such stretchable fabric may be manufactured to have both of its surfaces function as a strong loop fastener attachment means. An example of this is shown in FIG. 3A.

FIG. 3A. shows the cross cut view of a stretchable fabric, which has a body made of a stretchable fabric shown schematically at STRECH, and both the upper and the lower surfaces of the strap have the capability of functioning as loop fastener attachment means shown at ATM1. This kind of fabric may be made either by manufacturing such material or by sewing the fabric mentioned in FIG. 3 together, so that both upper and lower sides of this fabric would function as the stretchable, loop fastener attachment means. This applicant refers to this model strap as STR-L since technically is about the same as the other strap shown at FIG. 3.

FIG. 3B shows schematically, the general view of a support unit similar to the unit shown at FIG. 1, which has two pieces of double-sided attachment means such as the one shown on FIG. 2 being attached to its surface and it has a long stretchable strap made from STR-L with a zone of hook fastener attachment means ATM2-R at its rear surface. This unit is particularly designed for placement on the front of the leg or arm and allows the strap to wrap around moving up wrapping obliquely so that when it reaches to the end of the support the end of this strap will attach to its own rear surface by use of ATM2-R. Importantly, in this model the body of the DS-ATM 2 is made from a relatively rigid piece of PVC so that it would not allow the support to shrink and be moved down due to the shape of the leg, movement of the muscles and force of gravity, which is a very important function. Note also importantly, similar zones of DS-ATM2 may be also placed horizontally on the support to prevent the body of the support from shrinking in a horizontal direction. Note the reason the body of the DS-ATM2 is wider than that of the ATM2 in FIG. 3B is that it prevents the edges of the ATM2 from attaching to the side of the surface of the support and becoming disfigured; also a wider body will be more stable, and this is an important factor to mention.

Figure 4:
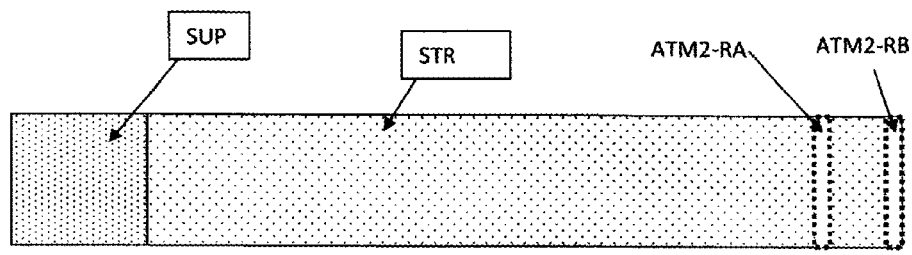
FIG. 4. Shows front of a strap attached to a support and zones of ATM2 in rear end of the strap.

FIG. 4 shows the front view of the prototype of the main embodiment of this invention in simplest form. This unit has a non-stretchable support SUP with an outer surface; made from a layer of loop-fastener attachment means, ATM1, and inner surface, made of a soft lining that stands on the skin, and a thin layer of foam sandwiched in between. The unit has a stretchable strap; STR attached to its right border either on a permanent or detachable basis; the other end of the strap STR has two zones of hook fastener attachment means, ATM2-RA and ATM2-RB, on its rear/lower surface, shown better in FIG. 4A so that after wrapping around a limb these zones can be attached to the outer surface of the support SUP on a detachable, re-attachable basis. Importantly, the unit may have only one zone of hook fastener attachment means, ATM2-R, in its lower surface, but the research of the applicant shows that it will be easier to handle if the strap has two or more such zones so that the ATM-RA will attach to the support first and keep the strap steady and allow the second ATM2-RB to attach to the support afterward.

Importantly, it should be known that at present the applicant has stretchable straps that allow the ATM2 to attach to both sides of the strap but one side attaches more than the other.

Figure 4A:
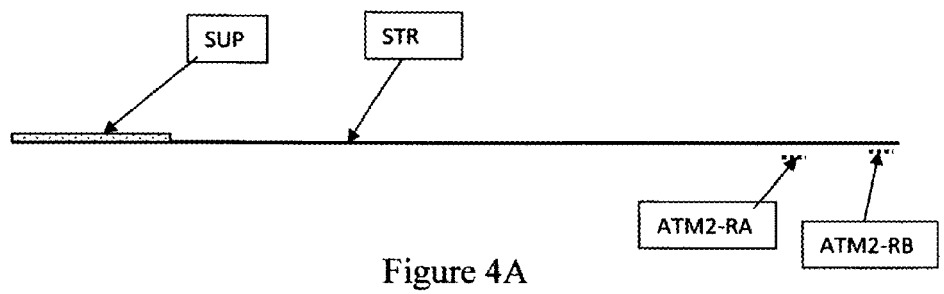
FIG. 4A. Shows cross cut view of the stretchable fabric and support shown at FIG. 4.

FIG. 4A. Shows the cross cut side view of the unit shown in FIG. 4, here the support, SUP is shown and the stretchable strap STR is attached to the right border of the support, the other end of the strap STR has two zones of hook fastener attachment means, ATM2-RA, AND ATM2-RB on its lower surface.

Figure 4B:
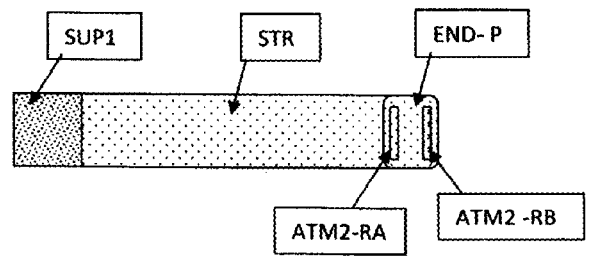
FIG. 4B. Shows a strap-support unit with an end piece at the end of the strap.

FIG. 4B. Shows the front view of a modified version of the unit shown in FIG. 4 except the end of the strap in this unit has an end piece, END-P, which has zones of hook fastener attachment means, ATM2-RA AND ATM2-RB, on its lower surface. The reason for the end piece is that the experiment of this applicant has shown that at times this modification makes the attachment of straps to the support easier and more manageable, particularly when the straps are wide. Thus it is advantageous to have this end piece, (may be referred as tongue) or similar. Also as mentioned earlier having more than one zone of ATM2 is important since the attachment of the first zone of ATM2-RA will make the strap attached to the support and will keep it stable, while the user still has the grab at the end of the end piece and can control and adjust it, then to attach the second zone ATM2-RB.

Figure 4C:
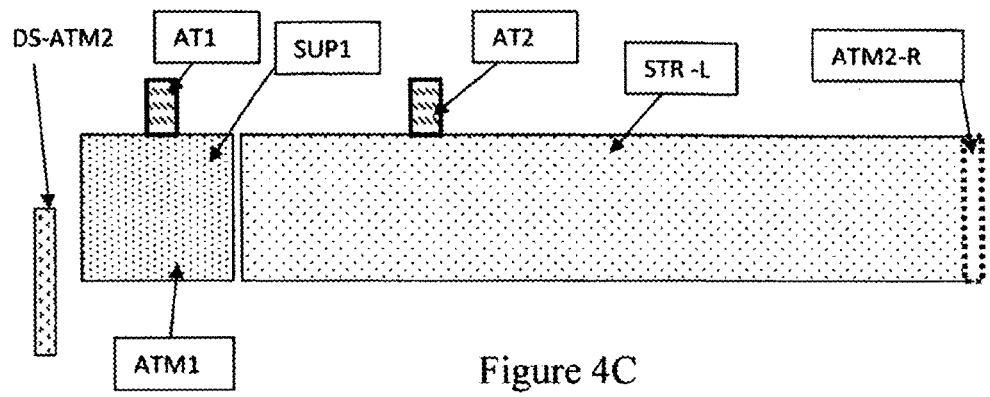
FIG. 4C. Shows a strap-support unit with zones of adhesives in their rear surfaces.

FIG. 4C shows the front view of a modified version of the prototype of this invention, which in this case the strap STR-L is made from a special stretchable fabric that is able to attach directly to the zone of hook fastener attachment means ATM2 of the support on a detachable, re-attachable basis. A sample of this strap is shown in FIG. 3. In this model the strap STR-L is also attached to the side of support; SUP1 either on a permanent or detachable basis, on the right border of the support. The other end of the strap STR-L has only one zone of the hook fastener attachment means, ATM2-R, in its lower surface so that the strap STR-L attaches to the DS-ATM2 of the support and will be stable. The support, SUP1 of this model also has a laminar body as mentioned earlier, and the important thing is that the outer surface; of the support shown at ATM-1 is made from a layer of loop-fastener, attachment means, ATM-1. This support has an inner soft lining and a thin layer of foam sandwiched in between. Importantly, in the left side of this figure, a long, narrow zone of double sided hook-fastener attachment means, DS-ATM2 is shown. By having both sides made from a hook fastener attachment means, ATM2, as explained in FIGS. 2 and 2A, this piece can be attached to the outer surface of the support means SUP1 on a detachable, re-attachable basis. Thus after attachment to support SUP1 it will allow the body of the strap STR-L to be attached to it directly on a detachable, re-attachable basis. The zone of hook fastener attachment means, ATM2-R, on the lower surface of the strap STR-L will attach to the outer surface of the support SUP1 on a detachable, re-attachable basis. This figure also shows that the support, SUP1, has an optional adhesive tape of its own, shown at AT1, which allows the SUP1 to be adhered to the skin. This adherence will prevent the movement and falling of the support in areas such as the thigh and groin where the particular shape of the area and the function of the muscles moves the support and strap down toward the knee. Also note that alternatively, this adhesive tape may be a zone of adhesive under the support, to be adhered to the skin and prevent the support from moving down. Also this figure shows the strap, STR-L, has an optional adhesive tape, shown at AT2, which will be adhered to the skin on an area such as the thigh to prevent the strap from moving and falling. These adhesive tapes are optional and each one of these adhesive tapes will have their own protective layer, which will be removed before use.

Figure 4D:
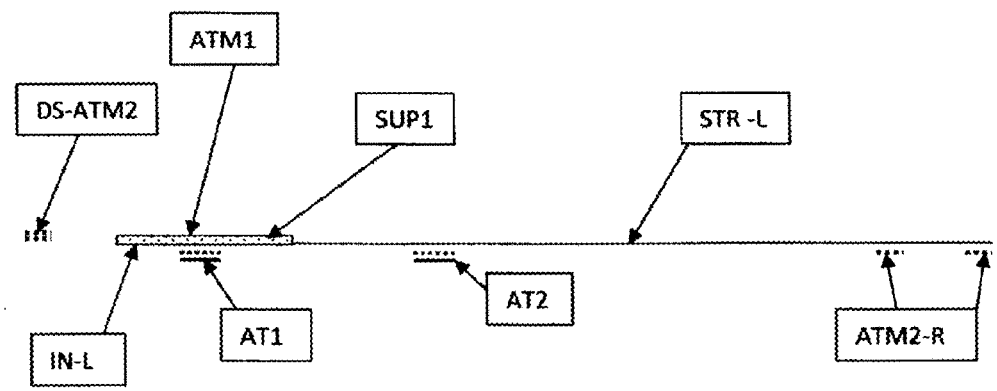
FIG. 4D. Shows cross cut view of the strap-support unit shown at FIG. 4C.

FIG. 4D shows the cross cut side view of the unit shown in FIG. 4C, here the support, SUP1 is shown, the outer, or the top, surface of this support is made from a layer of loop-fastener, attachment means, ATM1. This support has a laminar body with a non-stretchable body with an outer surface, its inner surface IN-L being a soft lining that stands on the skin. Also the cross cut of the flat, double sided hook-fastener attachment means, DS-ATM2 is shown. The adhesive tapes AT1 and AT2 are shown.

FIG. 4 E shows the front view of a support, SUP, with a body made from loop fastener attachment means, ATM1, which has a zone of adhesive, AT-S on its left border, covered with a protective layer. The adhesive, AT-S allows the end of a strap, to be attached to this support, SUP, for making a strap support unit which has a desired strap length. Also the rear surface of this support, SUP, has zones of adhesive layers, which are not shown at this figure but at FIG. 4F. This unit and method is designed to allow the length of the strap to be decided for a particular site. This may be used with every possible unit for example in units for the legs, which the length of the straps cannot be decided in each case before use.

Figure 4E:
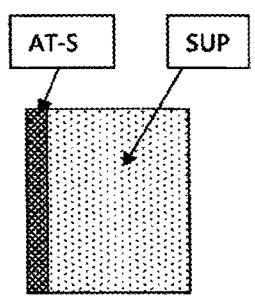
FIG. 4E shows a support with a zone of adhesive for attaching a strap.
Figure 4F:
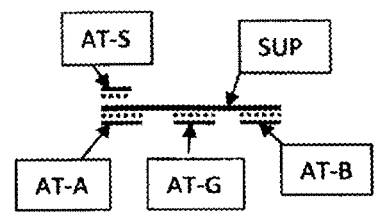
FIG. 4F shows the side view of the unit shown in FIG. 4E and with adhesives under.

FIG. 4F shows the vertical cross cut view/side of the support, SUP, shown in previous FIG. 4E. This figure shows the adhesive zone, AT-S shown at the upper surface on the left side with a dotted line, which has a protective layer, on its surface. Also the lower surface of the support, SUP, has three zones of adhesives, AT-A, AT-B AND AT-G. which are protected by a covers. These allow the following.

a. The adhesive, AT-A and AT-B is designed to allow the support, SUP, to be adhered to the skin and to prevent the movement and falling of the support on the wound site.

b. The adhesive zone, AT-G, allows a gauze pad, to be adhered to the body of the support.

c. The adhesive zone, AT-S shown at the upper surface of support on the left side, allows the end of a strap, to be adhered to the border of this support, SUP, for making a strap support unit with a proper length of the strap.

Figure 5:
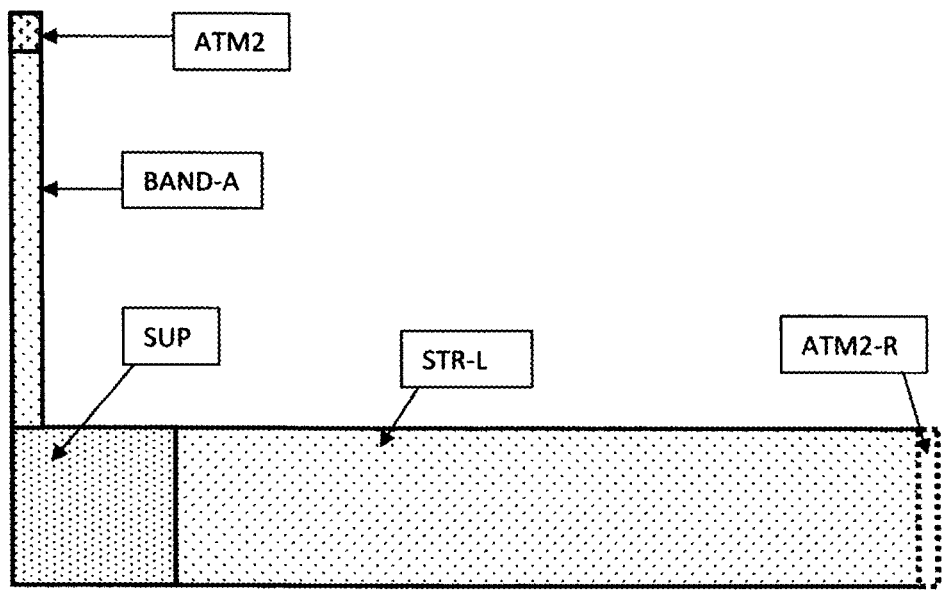
FIG. 5 shows a unit similar to FIG. 4 with one band, BAND-A attached in different direction.

FIG. 5 shows a unit similar to FIG. 4, except it shows how a strap may be attached in different direction. In this model one band, BAND-A is attached to the support in a vertical direction to the first strap and allows this band to go vertically and keep the support in stable status and prevent it from falling or moving vertically. The ATM2 at the end of the band will attach to the surface of the support, SUP, this band may also attach to another support if needed.

Figure 6:
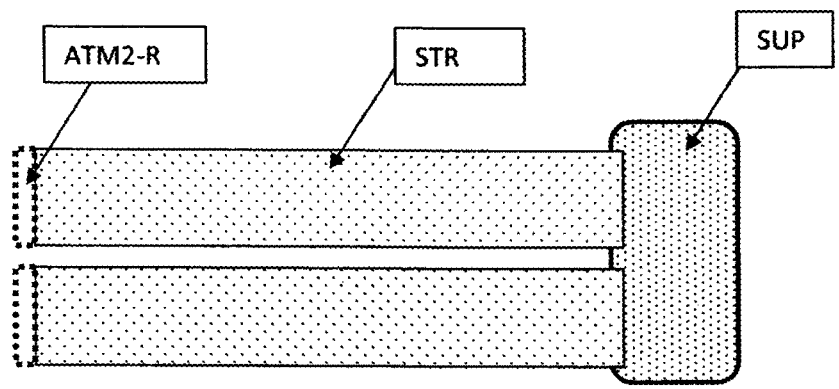
FIG. 6 shows a support with two straps attached to it in one direction.

FIG. 6. shows a unit similar to FIG. 4, except this figure shows that the support can have more than one strap, STR attached to it. In this model two straps, one shown at STR is attached to it. This is very important since in certain areas such as a long limb, arms or legs the long limb will need more than one strap to cover the area and this model allows such a coverage. Also Importantly, handling of a support with two straps allows an easy handling since the first strap will keep the support stable and the second straps can be placed with ease then the first strap to be adjusted. Thus a full, easy adjustment is possible with this method.

Figure 7:
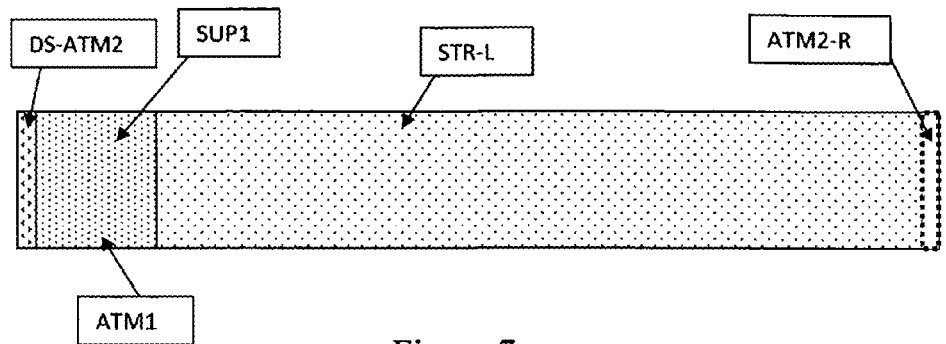
FIG. 7 shows a strap with ATM1 capacity, a sup and zones of double sided ATM2 attached.

FIG. 7 shows the front view of a modified version of the prototype of this invention shown at FIGS. 4 and 4A, except in this model the strap is made from a stretchable fabric that also functions as a loop fastener attachment means, ATM1, so that it not only is a stretchable strap but it can also attach directly to the zone of hook fastener attachment means ATM2 of the support on a detachable, re-attachable basis. This strap is referred here as strap STR-L. The strap is attached (permanently or removably) to the right border of the support, and in contrast to the model shown at FIGS. 4 and 4A in this model the other end of the strap STR-L has only one zone of hook fastener attachment means, ATM2-R, on its lower surface, so that after being wrapped around a lint, it will attach to the outer surface of the support SUP on a detachable, re-attachable basis. The reason for this is that the body of this strap will attach to the ATM2 of the support and will be stable before the attachment of the ATM2-R. In the left side of the support there is a long, narrow zone of double-sided hook-fastener attachment means DS-ATM2 that is attached to the outer surface of the support SUP1 (made of loop fastener attachment means ATM1) on a detachable, re-attachable basis. This will allow the body of the strap, STR-L, made of stretchable, loop fastener attachment means to be attached to this zone and the support SUP directly on a detachable, re-attachable basis.

Figure 7A:
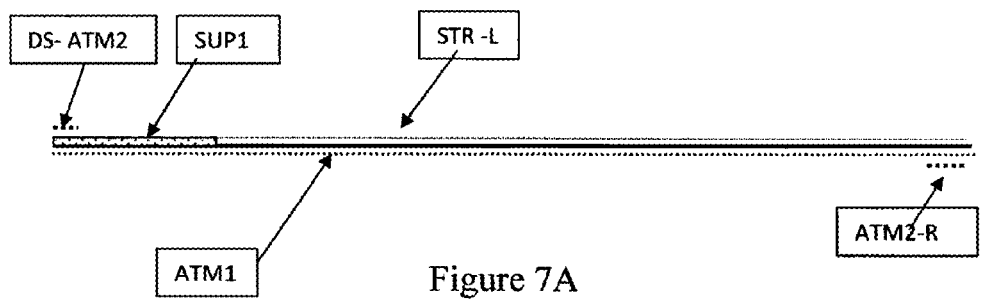
FIG. 7A shows the side view of the unit shown at FIG. 7.
Figure 7A:
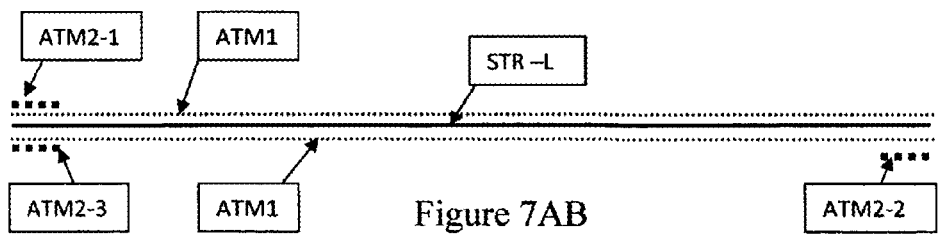

FIG. 7A. Shows the cross cut side view of the unit shown in FIG. 7, here the support, SUP1 is shown and the stretchable strap STR-L is attached to the right border of the support, the other end of the strap STR-L has a zone of hook fastener attachment means, ATM2-R, on its lower surface. Also the narrow zone of double sided hook-fastener attachment means, DS-ATM2 is shown on the upper surface of the support.

FIG. 7AB shows schematically the cross cut side view of a strap means similar to one shown in shown in FIG. 7A, which has zones of hook fastener attachment means on its ends, one on front and one on its back shown at ATM2-1 and ATM2-2. The strap is a stretchable strap STR-L which can attach directly to the zone of hook fastener attachment means ATM2 of its own end on a detachable, re-attachable basis. This model allows the strap to be wrapped around a limb and its body to attach to the attachment means ATM2-1 of its own first end on a detachable, re-attachable basis, then the rest of the strap to continue wrapping, and then the attachment means ATM2-2 on the second end to attach to the outer surface of the strap itself on a detachable, re-attachable basis. Thus this strap is functional and can be used alone and may be used as desired. Although adding the support to such straps as introduced by this applicant makes the use significantly simpler and easy to handle.

Having another hook fastener attachment means ATM2-3 will allow the first end of this strap to be attached to the support on a detachable, re-attachable basis.

Figure 7C:
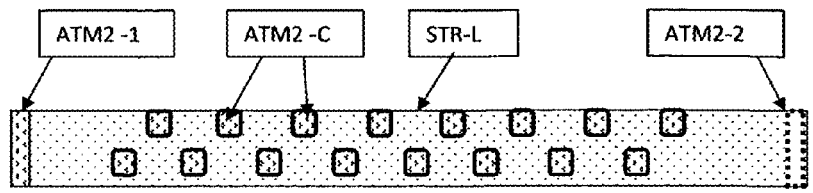
FIG. 7C shows a strap with ATM1 capacity, and zones of ATM2 in one surface and in back.
Figure 7C:
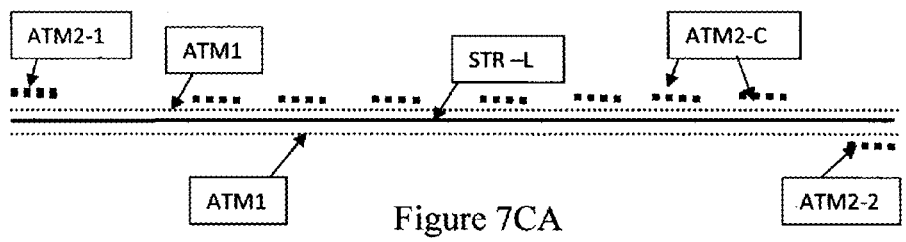

FIG. 7C schematically shows one surface of a strap means similar to one shown in FIG. 7AB, except this strap has more zones of attachment means ATM2 on its surface as shown at ATM2-C. The purpose of having such zones is to allow the body of the strap to attach to these zones, after wrapping the limb on a detachable, re-attachable basis. Such attachments make the strap more secure and would prevent its slippage. Please note that the numbers and position of the zones ATM2-C on the strap may vary and both sides of the strap may have zones ATM2-C and also zones of ATM1 as shown in FIG. 8.

FIG. 7CA shows schematically the cross cut side view of the unit shown in FIG. 7C, in this figure the body of the strap means is shown with zones of attachment means ATM2-1 and ATM2-2 as well as multiple zones of attachment means ATM2-C on the surface of the strap.

Figure 8:
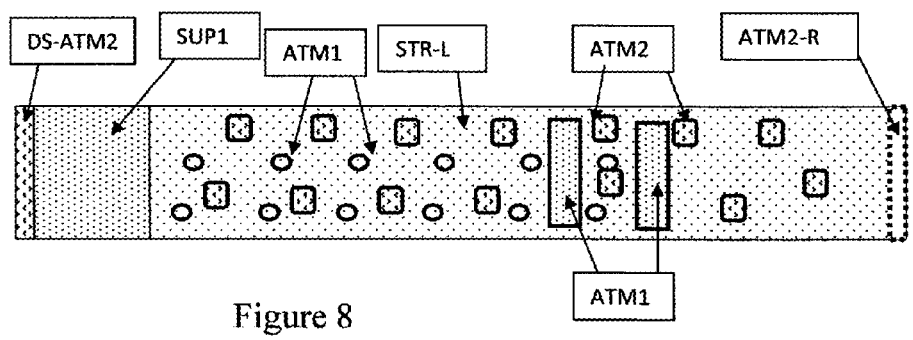
FIG. 8 shows a unit similar to FIG. 7 with multiple zones of ATM1 and ATM2 on its surfaces.

FIG. 8 shows the front view of a modified version of the unit shown in previous FIGS. 7 and 7A except in this unit still the strap STR-L is made from a stretchable, loop fastener attachment means, but it has multiple zones of loop and hook fastener attachment means on its surfaces. The advantage of this model is significant and allows a secure attachment of the straps to each other when they overlap and also more secure attachment to the support. Importantly, the size, the locations and the attachability of these zones may vary and it is important, for example, that there are two large zones of attachment means ATM1 in the front surface of the strap which will allow the end of the strap to attach to one of them or to the other small ones after wrapping the limb and if the strap reaches those spots. The importance of this is to control the extra length of the strap that wraps around and attaches to the support then attaches to its own rear surface and will not be loose.

Figure 8A:
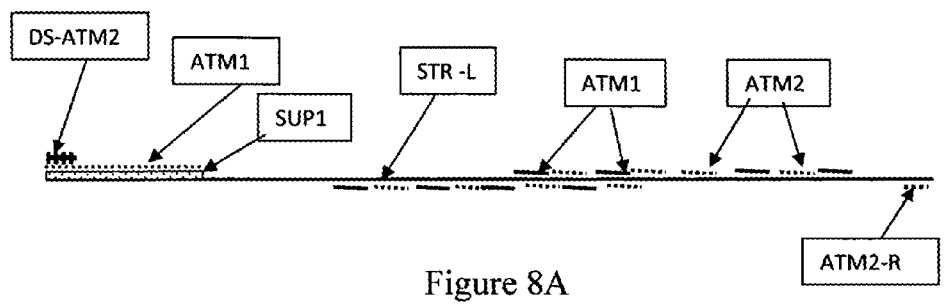
FIG. 8A shows the side view of the strap-support unit shown in FIG. 8.

FIG. 8A. Shows the cross cut side view of the unit shown in FIG. 8 and shows the zones of the hook, ATM2 and loop, ATM1 attachment means on the upper and lower surfaces of the strap STR-L. Importantly, please note that the size, numbers and locations of the zones of ATM1 and ATM2 in both upper and lower surfaces of the strap shown at FIGS. 8 and 8A may vary to allow different models to be made.

Figure 9:
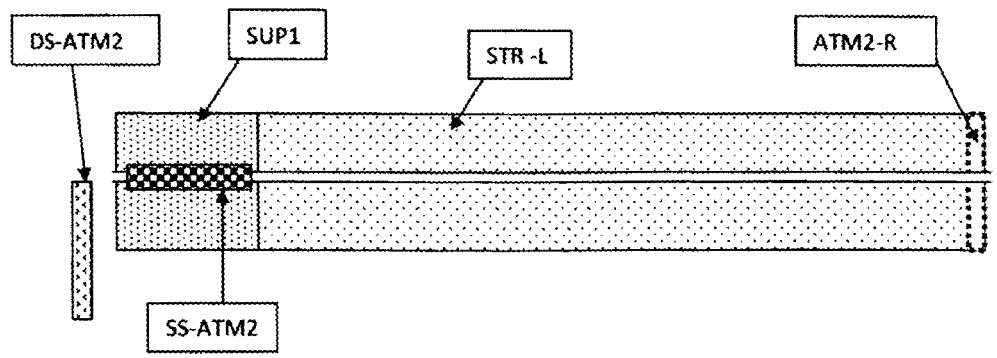
FIG. 9 shows two strap-support units similar to one at FIG. 4, attached to each other.

FIG. 9 shows the front view of a dressing unit that is made from combination of two units such as the unit shown in FIGS. 4 and 4A. This figure shows two narrower units similar to one shown at FIG. 4 with their supports attached to each other by use of a piece of hook fastener attachment means, ATM2, shown at SS-RTM2, on a detachable, re-attachable basis. This method allows the combined unit to function as a single unit with two straps and also allows one piece of this unit to be reversed and make a unit similar to one shown at FIG. 9B. The advantage of this newly made unit is that it allows one strap to come from one direction and the other strap, from the other direction of the support means. As it is explained in the text, the experiments of this applicant have shown that this method makes an easier placement and adjustment of the whole unit in some cases. Note the outer surface of the piece SS-ATM2 may be made from attachment means ATM1 so that it will match the surface of the support and allow the end of the strap to attach to it.

Figure 9A:
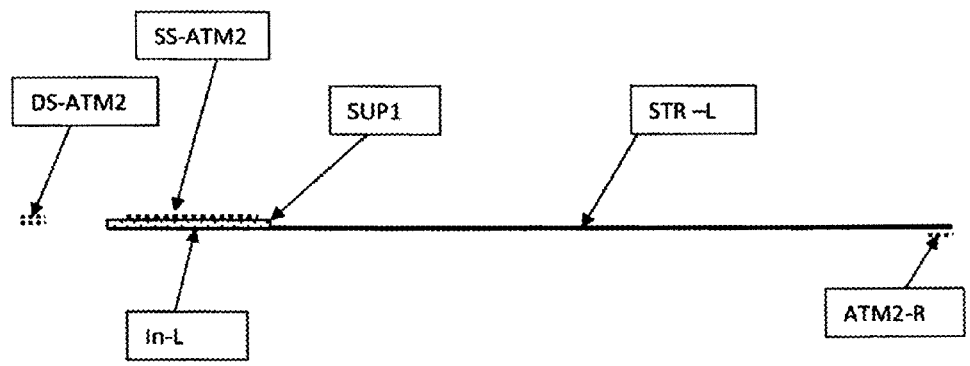
FIG. 9A shows the side view of the unit shown in FIG. 9.

FIG. 9A. shows the cross cut view of the unit shown at FIG. 9.

Figure 9B:
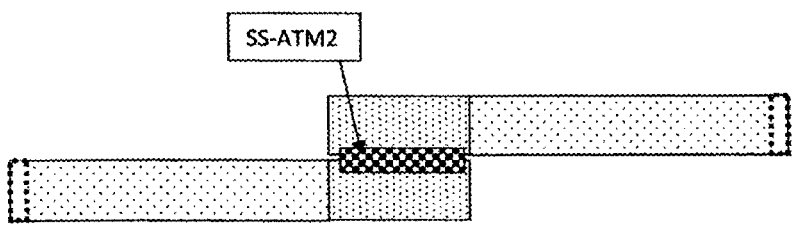
FIG. 9B shows the front view of unit shown at FIG. 9 with supports attached in different direction.

FIG. 9B shows the front view of the unit shown at FIG. 9 except in this model the supports pieces are attached to each other by use of a hook fastener attachment means, SS-ATM2 in a reverse manner so that the straps are positioned opposite to each other, and can be wrapped in opposite directions.

Figure 10:
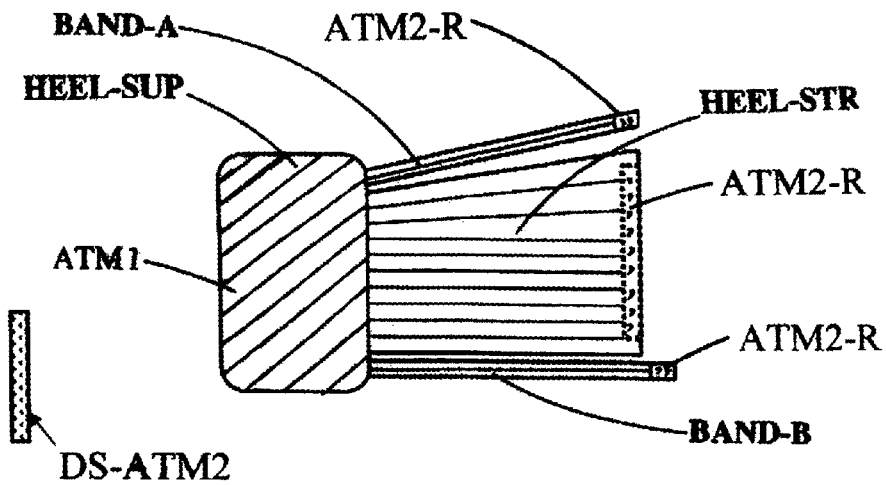
FIG. 10 shows the front view of a straps and support designed for use in ankle.
Figure 10A:
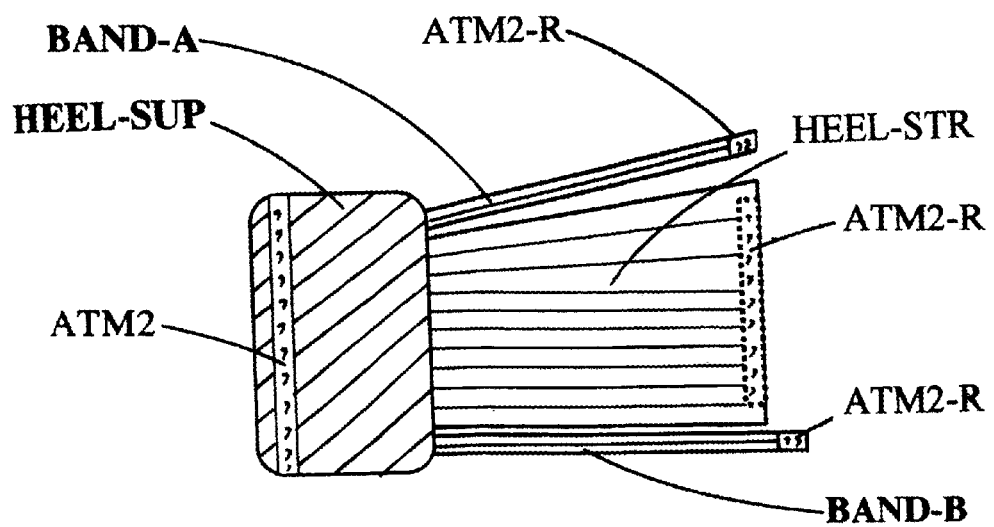
FIG. 10A shows front view of the unit shown at FIG. 10 with a zone of ATM2 attached to SUP.

FIG. 10 shows schematically the general view of a support unit for the ankle which is made with modification of the basic unit explained in this application shown at FIGS. 4 and 4A. This unit also consists of a non-stretchable, support, shown at, HEEL-SUP, that stands on the front or the upper surface of the ankle. The heel support, HEEL-SUP has a laminated body with the outer surface made from a layer of loop attachment means, ATM1, an inner surface, a soft lining with a layer of foam in between, although only the outer layer of ATM1 is essential. A stretchable strap, made from a stretchable fabric shown at HEEL-STR, is attached to the right border of the HEEL-SUP. The free end of this strap has a zone of hook-fastener, attachment means, ATM2-R on its rear surface. There are two narrower straps, referred here as the bands BAND-A and BAND-B which are very similar to the strap HEEL-STR and are made from a stretchable fabric similar to HEEL-STR, except they are narrower. These bands are attached to the right border of the HEEL-SUP and also the free ends of these bands have zones of hook-fastener, attachment means, ATM2-R on their rear surfaces. At the time of use the HEEL-STR will wrap around the heel and the ATM2-R at its end will attach to the outer surface of the heel support, HEEL-SUP, on a detachable, re-attachable basis. The two bands, BAND-A and BAND-B will also wrap around the heel and their end pieces will attach to the outer surface of the heel support, HEEL-SUP, on a detachable, re-attachable basis, by use of their end zones of hook-fastener, attachment means, ATM2-R located on their rear surfaces.

Importantly note, that a zone of double-sided hook fastener attachment means, shown in the left side of this figure at DS-ATM2 can be attached to the left border of the support and will allow attachment of strap to it on a detachable, re-attachable basis if the strap and bands are made from a stretchable, loop fastener stretchable attachment means, STR-L explained in the text. This model is shown at FIG. 10-A in more details.

FIG. 10-A shows schematically the general view of a support unit for the ankle similar to the support, shown at, HEEL-SUP, at FIG. 10 except with few difference. This unit is also designed to stand on the front or the upper surface of the ankle. It has a heel support, HEEL-SUP which is similar to the unit shown at FIG. 10 and is made from the laminated material with an outer surface made from a layer of loop attachment means, ATM1. Importantly, the left border of this support has a long, rather narrow zone of hook attachment means, shown at ATM2. which can be fixed or be made from a zone of double-sided hook fastener attachment means, shown in the left side of FIG. 10 at DS-ATM2, which can be attached to the left side of the support close to its border. This zone of ATM2 will allow the attachment of strap to it on a detachable, re-attachable basis if the strap and bands are made from a stretchable, loop fastener stretchable attachment means, STR-L explained in the text. Thus it allows this strap to attach to the hook attachment means, ATM2 of the support on a detachable, re-attachable basis. Please note that although the straps of this unit are not marked different but their function will be similar to STR-L. This model facilitates the placement of this unit on the ankle significantly and has significant importance. The free ends of the heel strap, HEEL-STR has a zone of hook-fastener, attachment means, ATM2-R on its rear surface that will attach to the outer surface of the heel support on a detachable, re-attachable basis. At the time of use this strap will wrap around the heel and its body will attach first to the ATM2 of the Heel support and its end piece will attach to the outer surface of the heel support, HEEL-SUP, on a detachable, re-attachable basis, by use of its end zone of hook-fastener, attachment means, ATM2-R located on its rear. Also the unit has two bands, BAND-A and BAND-B which are also made from a loop fastener, stretchable fabric, STR-L similar to HEEL-STR, and are attached to the right border of the HEEL-SUP, with their free ends of having zones of hook-fastener, attachment means, ATM2-R on their rear surfaces. Similar to the heel strap, these bands will wrap around the heel and their body will attach to the ATM2 of the heel support, HEEL-SUP, on a detachable, re-attachable basis also their end pieces will attach to the outer surface of the heel support, HEEL-SUP, on a detachable, re-attachable basis, as well by use of their end zones of hook-fastener, attachment means, ATM2-R located on their rear surfaces.

This system and method is very important and will facilitate the application of this unit very significantly.

Figure 11:
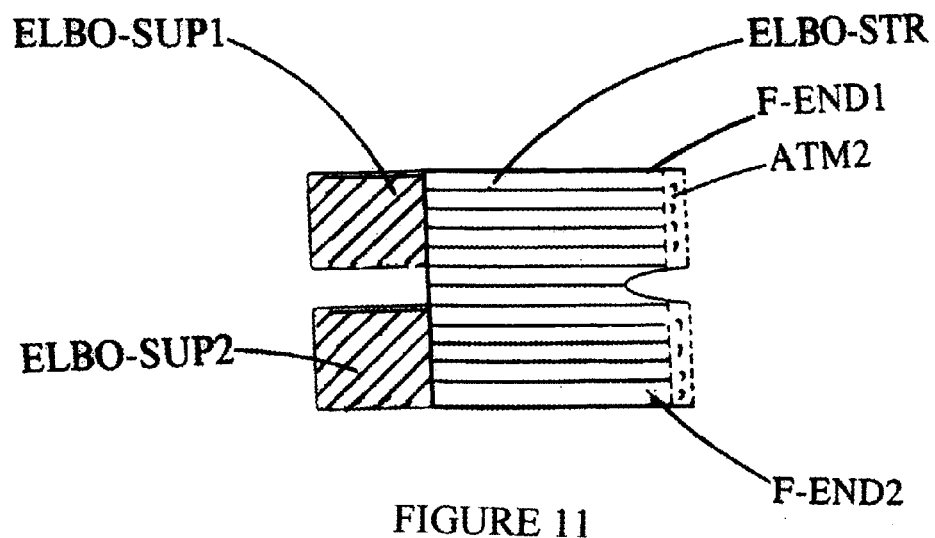
FIG. 11 shows a strap-sup unit designed for use in elbows, without ATM2 on supports.

FIG. 11. Schematically shows the general view of a support unit for the elbow. This unit has two pieces of a non-stretchable, support shown at ELBO-SUP1 and ELBO-SUP2 that are designed to stand on the front part of the elbow, above and under the elbow crease. These supports are made from support means, SUP1 which has a laminated body with an outer layer made of loop-fastener attachment means, ATM1 as mentioned earlier. A wide, continuous elastic strap, shown at ELBO-STR, is attached to the right border of the elbow supports, ELBO-SUP1-2. The elbow strap, ELBO-STR, has two free ends, F-END1 and F-END2. The inner surface of these free ends has a zone of hook-fastener attachment means, ATM2 (this can be a double sided, hook-fastener, attachment means). This strap is designed to wrap around the elbow and have its free ends, F-END1 and F-END2, attached to the outer surface of the elbow supports, ELBO-SUP1 and ELBO-SUP2, on a detachable, re-attachable basis.

This method makes a comfortable, sturdy unit for the elbow joint. Importantly, this leaves the front of the elbow open to bend freely.

Figure 11A:
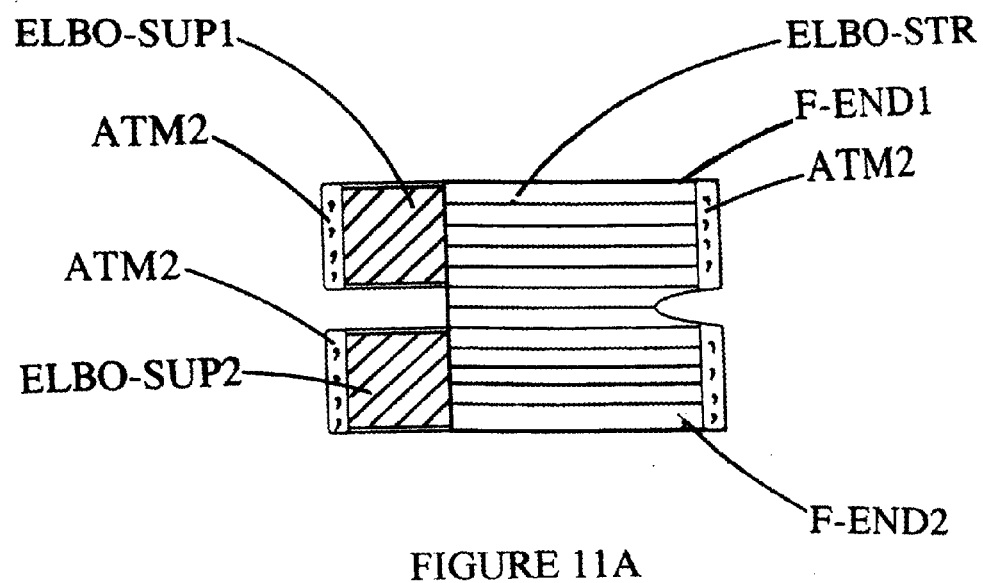
FIG. 11A shows a strap-sup unit similar to FIG. 11 with a zone of ATM2 on supports.

FIG. 11A. schematically shows the general view of a support unit for the elbow very similar to the unit shown at FIG. 11 except.

a. the support has a zone of double sided hook fastener attachment means attached to it on a detachable, re-attachable basis, shown at ATM2.

b. The stretchable strap is made of a loop fastener, stretchable fabric shown at ELBO-STR, which as explained in the text, as STR-L and is both stretchable and functions as a loop fastener attachment means and is capable of attaching to the zone of hook-fastener attachment means, ATM2 from the outer surface of the elbow supports, ELBO-SUP1 and ELBO-SUP2, on a detachable, re-attachable basis. This unit not only will work like the unit shown in previous FIG. 11, but also gives the option to the user to place an double sided attachment means to the support and use it much easier if need comes. Please note otherwise these units is very much the same.

Figure 12:
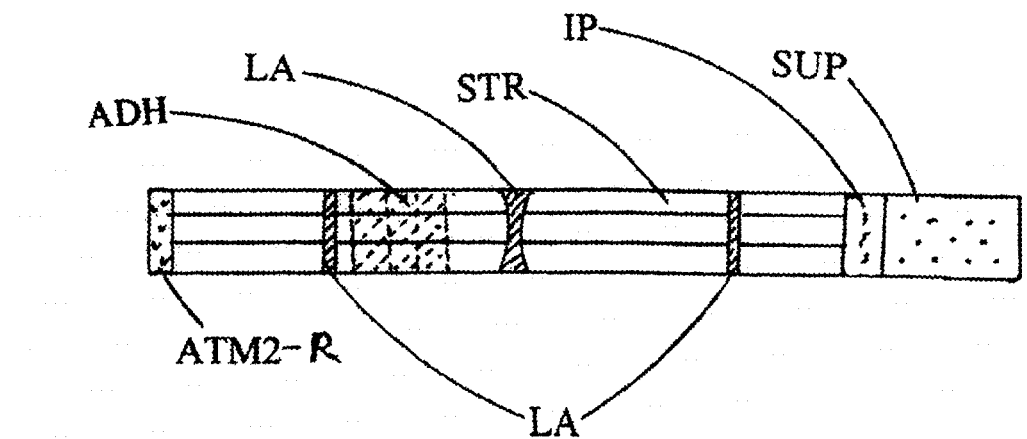
FIG. 12 shows a support unit and a strap with latex or shaped means on it, and a zone of adhesive.

FIG. 12. Shows a long strap, STR attached to a support that has a transparent pocket, IP attached to it. This figure also is meant to illustrate few important points and parts:

1. The support is covered with a loop fastener attachment means ATM1, so that the end of the strap with a zone of hook fastener attachment means, ATM2-R on its rear will be able to attach to it. Note that if the strap is made from a loop fastener, stretchable fabric and a zone of hook fastener attachment means, ATM2 is attached to the surface of the strap a double attachment will occur as explained.

2. A transparent pocket for placement of information, here referred to as the Information Pocket, IP is utilized, which can be part of the support, SUP or on the strap. The Information Pocket, IP, allows a piece of information to be placed inside the pocket. This information may be, time of the use of the dressing, giving medication, time of placement of an underlying IV line, or other information about the person using the unit, etc., and can be exchanged as needed.

Importantly, the information pocket, IP, may be placed on the wall of the strap to be part of the wall or simply attached to it.

3. Importantly, the body of the straps, STR, may have zones of materials such as latex, LA, in or on it to allow the shape of the strap to be conformed or modified to a desired shape. Such a modification many be used to prevent curling of the strap, etc. The shape, width, thickness, materials, and other characteristics of these zones may vary.

Importantly, two straps may criss-cross to allow a better placement. This is more useful in strapping the head wounds, with one strap going around the front and the occipital area and the other going from the vertex to the under chin area.

Figure 13:
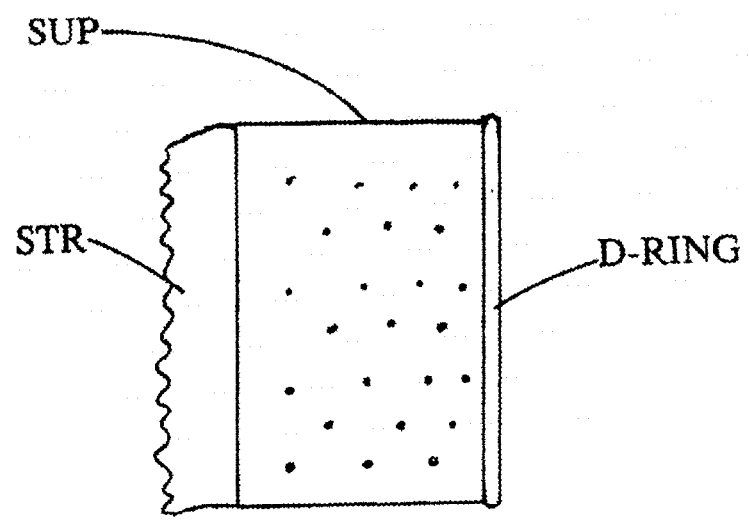
FIG. 13 shows a D-Ring on the side of the support that allows the strap to make a U-turn.

FIG. 13. Shows schematically use of a D-Rings with the support unit, to allow a strap to go through and make a U turn and the end of strap to attach to its own rear surface by various means for having the size of the strap adjusted. In this figure a transparent support, SUP, the D ring, D-RING and part of strap STR are shown.

Figure 14:
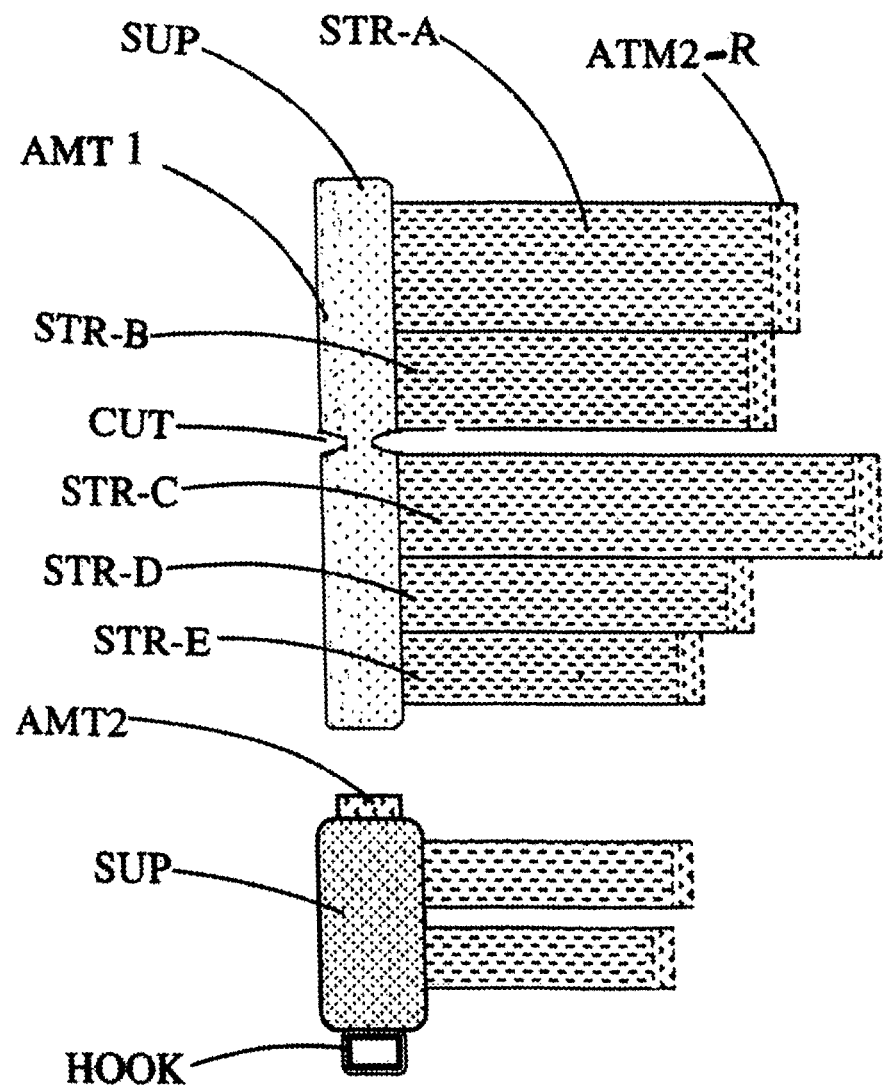
FIG. 14 shows a strap-support means for use in the arm, forearms and hand.

FIG. 14. Shows the general view of a support unit made of loop fastener attachment means, ATM1, similar to main units shown in FIG. 1. Except it is modified for use in the arm and forearm to allow the wound dressing and/or compression of limb in these areas. In this model, the support, SUP, has a long, rather rectangular shape with cuts in its sides, CUT, for the elbow crease. The support, SUP stands on the front of the arm and forearm, or on its rear side. The support, SUP allows the end of the straps, such as STR-A, with a zone of ATM2 in its rear, marked at ATM2-R to be attached to the outer surface of the support on a detachable, re-attachable basis. A series of straps: STR-A, STR-B are attached to the right border of the support, SUP, and will wrap around the arm, another series shown at STR-C, STR-D and STR-E, are designed to wrap around the forearm. These straps are attached to the border of the support, SUP, on a permanent or detachable basis, as for the leg support on FIG. 16. These straps are properly sized to be wrapped around the arm from the axillary area to the elbow-joint area to cover this area uniformly. Importantly, this unit may have three straps for the arm as well or more. The straps for the forearm will be placed in the upper, mid- and lower forearm. The free ends of these straps will attach to the support, SUP, by use of pieces of hook fastener attachment means, ATM2, located in the rear surface of their ends. Similar to the leg straps, shown in FIGS. 16 and 17 this method allows the unit to be used for dressing, supporting and compressing the arm and forearms in a very practical, adjustable manner. In this model the straps are made from a stretchable material and the support means, SUP, is made from a non-stretchable, material with a laminated body with an outer surface made from a layer of loop-fastener attachment means, ATM1, and an inner layer made from a soft lining that stands on the skin with a thin layer of foam in between. It may also be made from any other materials such as fabric or any other man-made materials. The support may have openings to allow sweat and air to go through and also allows a removeable layer of lining or pad to be placed under for prevention of irritation, application of pressure, or application of medication, etc. Importantly, this unit also allows the placement of electrical leads in the area for a programmed stimulation of the arm muscles and tissues for reasons such as the prevention of muscle weakness or prevention of phlebitis. Importantly, the narrow area of the support between two cuts, CUT, will function, to keep the lower part of the support in place and prevent it from falling and will function as a hinge and allows the lower segment of the support to rotate in different directions. Note importantly some of the straps may come in opposite direction as shown in previous figures.

The advantages of this unit are that:

1. It makes the placement of this unit with one hand possible.

2. It is possible to adjust the tension of each strap individually. This allows the pressure in each segment of the arm or forearms to be modified easily, without disturbing the whole unit, which is not possible by a commonly used wrapping system.

3. The arm and the elbow to function easily due to presence of the cut in the support.

4. The arm and elbow to be hung from a stand in order to facilitate the drainage of the tissue.

5. This unit can be placed and removed rather easily. Since placement of only one strap holds the support in place and allows the other straps to be placed. Then by adjusting each strap the whole unit can be adjusted.

6. Placement of a lining which may be attached to the support, SUP, of the unit on a detachable, re-attachable basis. This allows the lining to be washed or exchanged.

Figure 17:
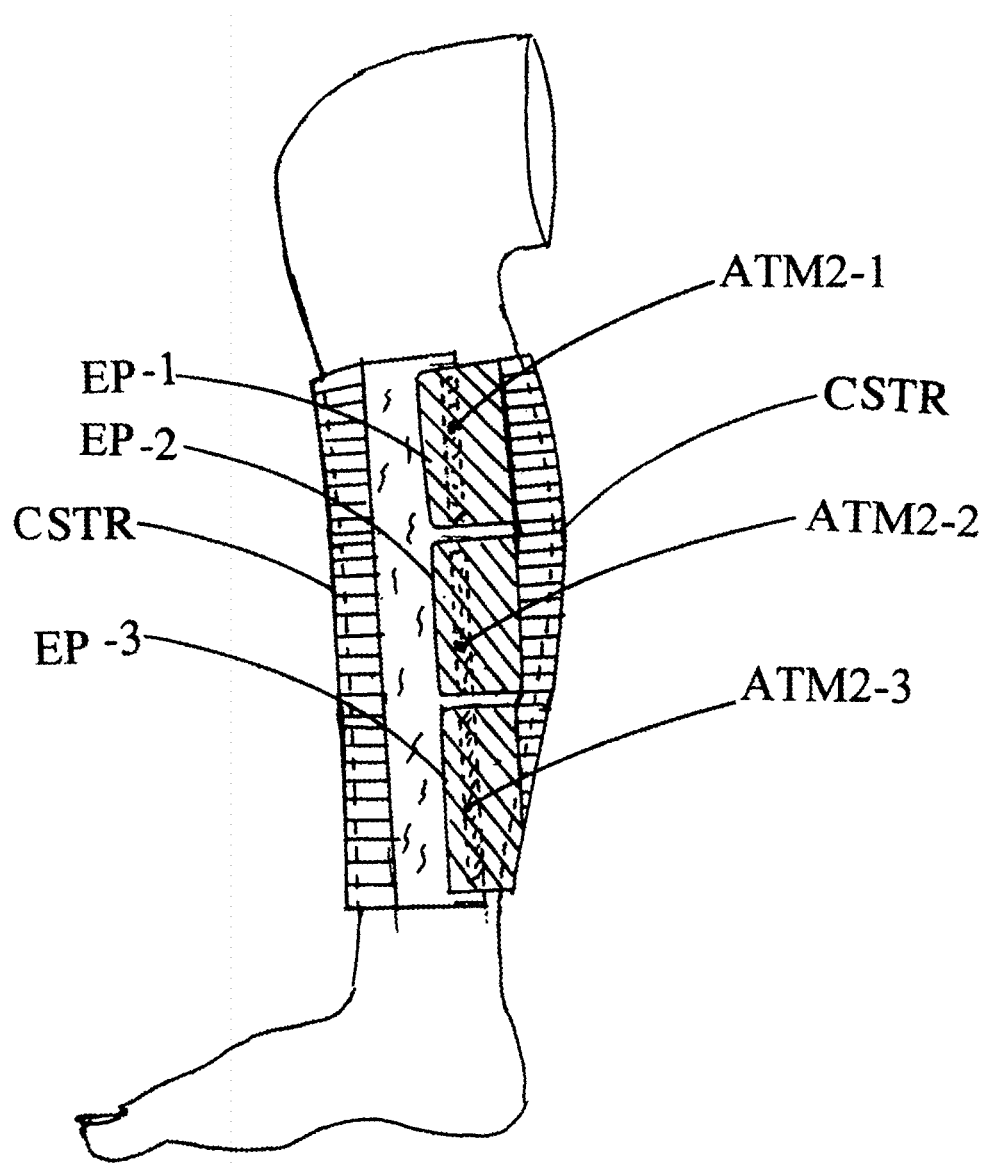
FIG. 17 shows the side view of a leg unit consisting of a single common wide strap, CSTR.

The lower part of this figure shows a piece that allows this unit to be extended to the hand and be attached to an automatic height elevator designed by this applicant. This part shows a support for hand, SUP that stands on the rear of the hand, and will be attached to the lower extension of the support of the arm-elbow by the hook-fastener attachment means, ATM2, in the upper end of the hand support. The straps of this support will wrap around the palm and fingers and will attach to the rear surface of the body of the hand support. The hook in its lower end allows this support to be attached to the hook, HOOK, of the remote-controlled elevator designed by this applicant and shown in his previous inventions. Importantly, note the straps are separate and not attached to each other but they overlap. They can be attached to the support individually. Importantly, the straps of these units may be attached to the support unit independently by having both their ends attached to each side of the support on a detachable, re-attachable basis. Importantly also, the straps may be made from a continuous layer of stretchable fabric, as shown in FIG. 17 for the leg, to allow a uniform coverage of the area. Thus it will be a continuous layer of the strap that will be attached to the border of the support without having a cut or space in the body of the strap in this side. However, it will have end pieces which will be separate to allow easy placement, similar to the units shown for the leg at FIG. 17 and is not repeated here to avoid a lengthy application. Importantly, the use of methods explained in this application will allow the end of the straps to attach to the outer surface of its own if the length of the strap is long and passes the support after being wrapped around the limb. Also importantly, the strap may be made from a stretchable, loop fastener fabric such as STR-L and the support may have a zone of double sided ATM2 attached to it in order to allow the strap to be attached to it after being wrapped around the limb.

Figure 15:
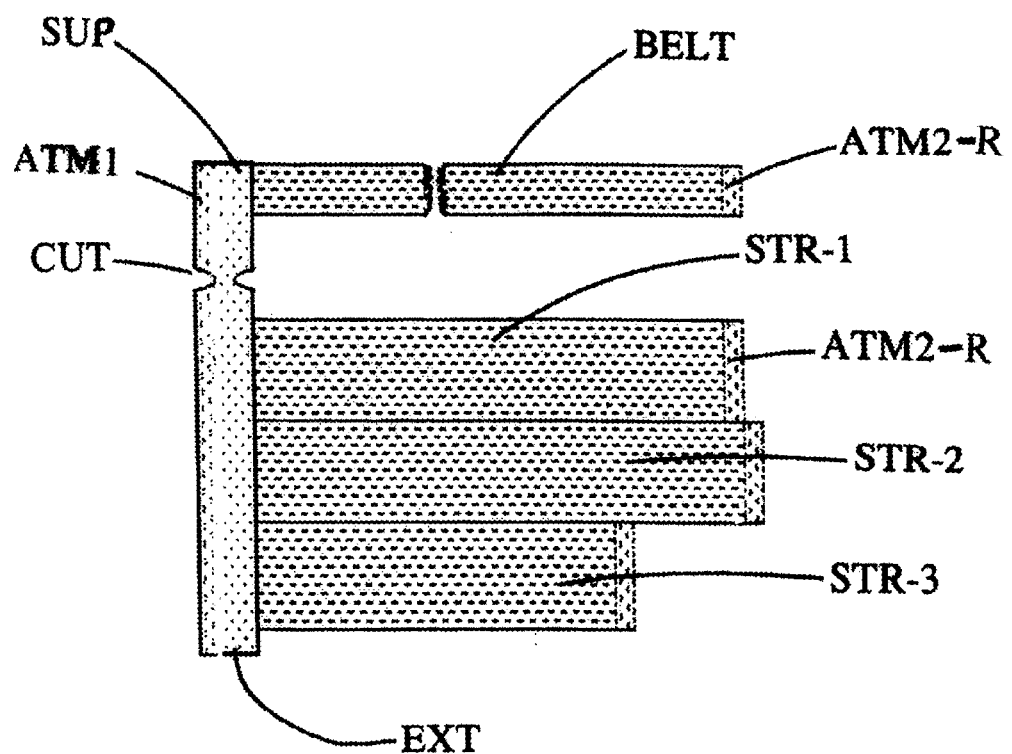
FIG. 15 shows a strap-support means for use in the thigh area.

FIG. 15 shows the general view of a support unit similar to the unit shown at FIG. 14, except this unit is modified for use in the thigh area. This unit also has a long support, SUP, with cuts, CUT in the sides as shown to stand on the hip joint and function as a hinge. The upper part, above the cut, CUT, of the support, SUP, is a belt like unit for placement on the waist and the lower part of this unit will be placed on the lateral side of the thigh. The area with cut, CUT, will function as hinge allow the lower part of the support, SUP, to rotate in the different directions without being disconnected from the upper part. The support, SUP, has a series of straps attached to it. The first strap functions as the belt and is marked at, BELT. This will hold the support and prevent it from falling. The BELT, goes around the waist and attaches its free end to the outer surface or the edge of the support, SUP, and then attaches the free end of the belt to the outer surface of its own. Using a D-Ring may help to have the length of these straps to be controlled. This is possible due to the presence of the attachment means at the end of the belt. Importantly, the belt may be made from a non-stretchable material to keep the unit in place sturdy, such as a commonly used belts, but modified to hold the support, SUP. The belt may have zone of ATM2, and ATM1 outside to allow the support and end of its own to attach to them. The other straps, STR-1, STR-2, and STR-3, are attached to the body of the support on a permanent/or re-attachable basis in one side. These straps will individually wrap around the thigh and attach to the support due to the presence of the hook fastener attachment means, ATM2, at the free ends of the straps on a detachable, re-attachable basis (as shown for the leg support). These straps are properly-sized to wrap around the thigh from the groin area to the upper knee. Importantly, the support, SUP, may have an extension to cover the knee area with a strap going around the knee. Importantly, the use of methods explained in this application will allow the end of the straps to attach to the outer surface of its own if the length of the strap is long and passes the support after being wrapped around the limb. Also importantly, the strap may be made from a stretchable, loop fastener fabric such as STR-L and the support may have a zone of double sided ATM2 attached to it in order to allow the strap to be attached to it after being wrapped around the limb. Importantly, the extension, shown at EXT, will allow the attachment of this unit to the support of the leg support. Importantly, the effective length of these straps may be modified by use of the methods and means explained in different parts of this application. Similar to the leg straps, this method allows the support and straps to be used for dressing and supporting the thigh in a very practical, adjustable manner. In this model the straps are stretchable fabric and the support means, SUP, is made from a non-stretchable, body with an outer surface made from a layer of loop attachment means, ATM1. It may also be made from any other materials such as fabrics or any other materials explained in the text in the support's explanation. Importantly, the thickness of the straps may vary in this unit and every other unit to fulfill the need, thinner straps will hold dressing in place while the thicker straps will allow more tension build up and pressure to the tissues. The support may have openings to allow sweat and air to pass through and also allows gauze pad or a long, removable layer of lining or pad to be placed under it to prevent irritation, place pressure, and allow application of medication, etc. This unit may allow electrical leads to be held in place for a programmed stimulation of the thigh muscles and tissues, for various reasons such as prevention of muscle weakness or prevention of phlebitis. The advantage of this unit is that it allows compression of the whole thigh with the option to adjust the pressure in every special segment of the thigh. Also the unit can be removed and placed with ease. Note these straps are not attached to each other and are separate. Importantly, the straps of may be attached to the support unit independently, by having their both ends attached to each side of the support on a detachable, re-attachable basis. Importantly, in this model also the strap may be made from a single layer of fabric to allow a uniform cover of the area although their end pieces or the attachment means and the area adjacent to it will be separate to allow easy placement. An example of this model is shown for the leg in FIG. 17 and will not be repeated to avoid a lengthy application. Importantly, the support may be made from a stretchable material or have zones of stretchable material in it. Importantly, the straps over lap each other to prevent from leaving gaps in between. Importantly, the belt may be made from strap made of non-stretchable ATM1, with a Zone of ATM2 at its end.

Figure 16:
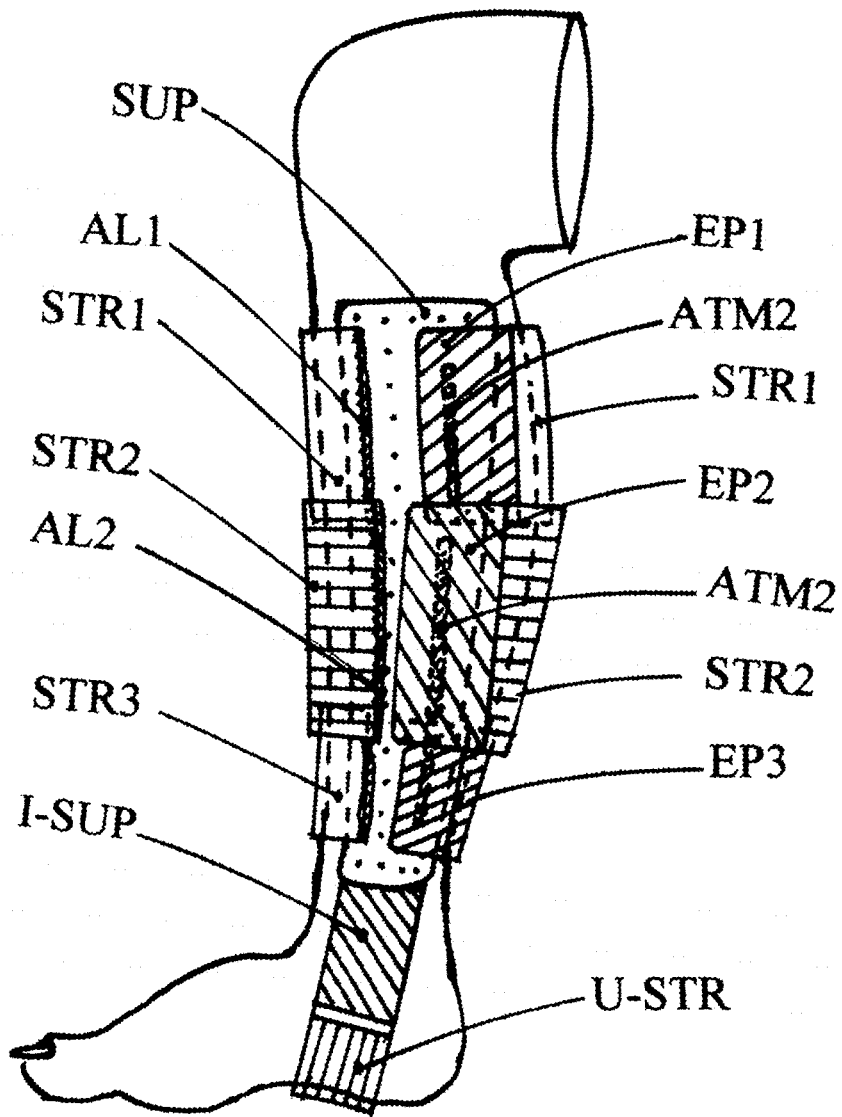
FIG. 16 shows a leg support with 3 straps attached to the border of the support and an ankle unit.
Figure 16:
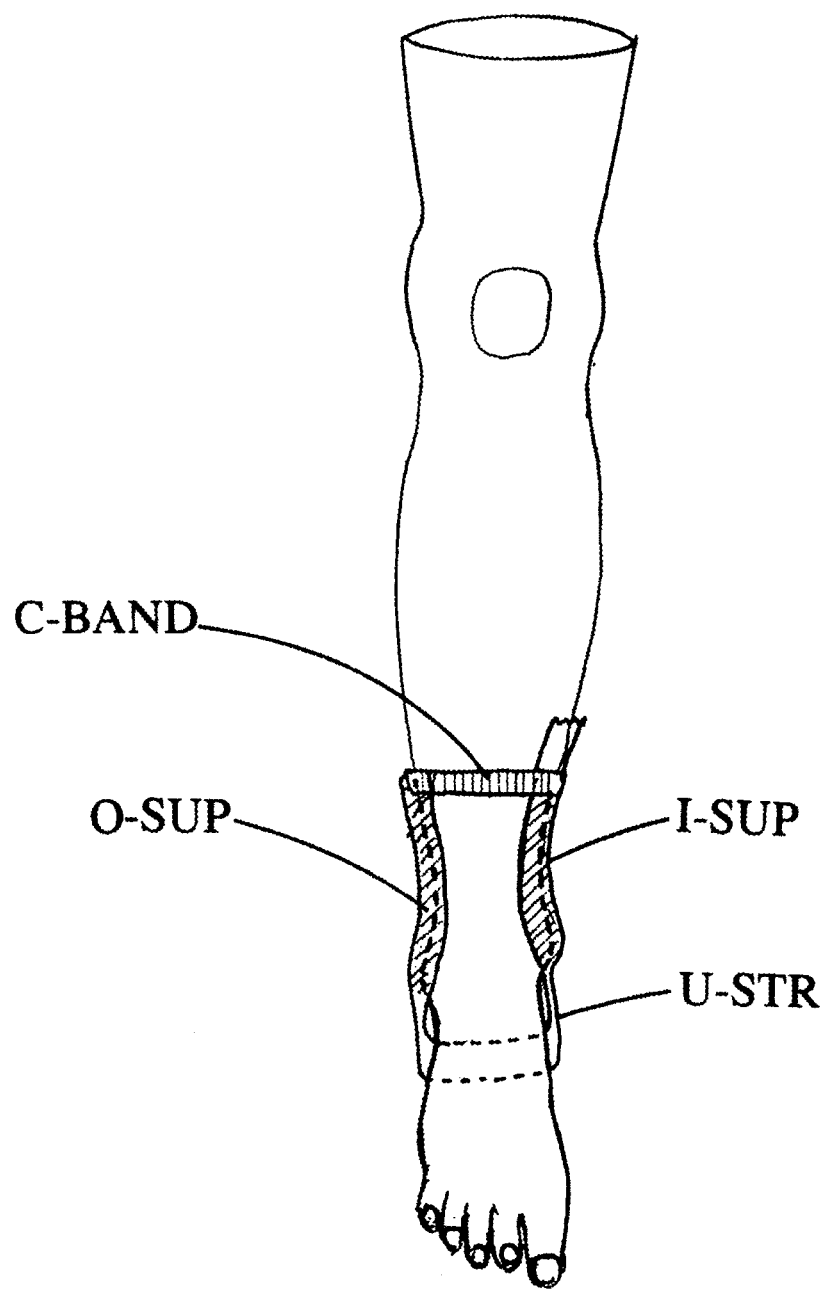

FIG. 16 shows a very important model of this invention. It shows the general view of a support unit for use on the legs. This unit allows secure and easy dressing of the legs or simply to compress the leg to a desired degree. In this model a support means, SUP, is used which has a long, rather trapezoid shape sized to stand in front of the legs or the wound site. In simplest form the support, SUP, is made from a layer of fabric made of loop attachment means, ATM1 in its entirety that allows pieces of hook-fastener attachment means; ATM2 to be attached to it on a detachable, re-attachable basis. On the left border of the support, SUP, three straps: STR1, STR2 and STR3 are attached to the support along the attachment lines, AL1, AL2 but the attachment line of the $3^{rd}$ strap STR3 is not shown to prevent a crowded figure. The attachment of these straps to the support can be fixed or by a detachable re-attachable, method. These straps are sized to wrap around the leg on its upper, middle and lower part, and their free ends to attach to the support by use of their end pieces. The end pieces (which may be referred to as tongues), EP1, EP2 and EP3 simply serve to allow a simple and easier handling and placement of the straps. The inner surface of these end pieces; EP1, EP2 and EP3 which is toward the support SUP has at least one zone of hook-fastener attachment means; ATM2 that allows the end pieces to be attached to the support, SUP, on a detachable, re-attachable basis. Note that the zones of hook-fastener attachment means ATM2 may be double sided and they may be attached to the support, SUP, made of attachment means ATM1 on a detachable, re-attachable basis, but will function the same. The use of double sided attachment means, ATM2, has the advantage that allows the location of the attachment means ATM2 on the support to be adjusted. Importantly, in this model the end pieces EP1, EP2 AND EP3 may be made from attachment means ATM1 so that they can attach to zones of attachment means ATM2 on the support. Importantly, note that it is possible as this applicant has shown before, to make the support means from vinyl, or any other non-stretchable material with zones of hook-fastener attachment means ATM2 so that when the end pieces are made from loop-fastener attachment means, ATM1 they can be then attached to the support, at ATM2 on a detachable, re-attachable basis. Also the support, SUP, may have a body with stretchable and non-stretchable segments.

Importantly, note this method allows the straps to overlap each other. For example in this figure the middle strap STR2, has a wide body and overlaps over the straps STR1 and STR3, such overlapping being medically very important since it will prevent a portion of a limb from being entrapped between two straps without being covered by a strap. If the straps did not overlap, the segment of vein between these two straps will not be pressured; thus it will be engorged with blood, the circulation will slow down and it will make a media for thrombosis which medically is to be prevented at all cost.

This figure also shows an optional U-shaped extension piece that is attached to the lower part of this unit. This U-shaped piece is designed to support the middle and lower ankle area in both sides of the ankle, inside and out, and allows the compression of these areas. In this ankle model a rectangular support, SUP, made of ATM1 similar to one that is explained in this figure or an extension of the support of the leg support is utilized and shown as the inner support, I-SUP, and functions to compress the inner part of the ankle. The front view of this part is shown in FIG. 16A. In this unit the inner support, I-SUP, moves down and covers the inner ankle area and connects to a piece of a stretchable strap shown at U-STR. This U-strap makes a U-turn under the foot and attaches to another non-stretchable support that functions as the outer support, O-SUP, shown in FIG. 16A. The outer support compresses and supports the outer ankle area and has a stretchable strap or a band, C-BAND, which wraps around the lower leg or ankle area and holds the outer support O-SUP in place. The band C-BAND allows a wider strap, such as strap STR3, shown at FIG. 16 to wrap around the supports I-SUP and O-SUP and to keep these supports in place, squeezing the tissue in between them. The importance of this unit is:

A. Having a U-shaped support means, which supports the middle, lower and lateral part of the ankle and allows the compression of the tissues in these areas. So that it allows the dressing and compression of the tissue and vessels in the lower inner ankle-foot area to occur for a better result. Importantly, the pressure in the area can be measured by placement of a balloon connected to a gauge and adjustable manner. Use of such compression is very useful in vascular problems such as the venous insufficiencies of the legs, where compression of vessels for decreasing the inner pressure of the vessels and prevention of extravasations of fluid is needed. Please note that in order to prevent confusion, the upper parts of the unit are not shown in this figure.

Importantly, in some cases there is a need for further compression of the lower leg to raise the amount of pressure on the tissue. In such cases the inner support, I-SUP and the outer support, O-SUP, are made from a rather rigid pieces, such as a shaped polymer or metal, that are connected to each other in the lower side by a strap. The position of this strap on the supports is adjustable and allows the distance of the inner support, I-SUP, and the outer support, O-SUP, to be adjusted. Importantly, the outer surfaces of the inner support, I-SUP, and the outer support, O-SUP, have attachment means, such as hook-fastener attachment means, ATM2. This allows a wider, horizontal strap or two straps similar to one shown at C-BAND to wrap around the lower leg and hold the I-SUP and the O-SUP in place to further compress the tissues in this area. This combination can be used as a separate unit, or in combination with the leg support. Importantly, the rigid supports can be pre-shaped or alternatively made from a material which accepts the shape of the area after placement. Pieces of shaped foams, gel filled units, pads or any other useful units may also be placed between the wound dressing and these supports. A flat, fluid-filled balloon attached to a measurement unit may be placed between the support and lining to monitor the pressure in the wound.

FIG. 16B shows the side views of the pieces for a U-shape extension for use with the leg support. This unit is designed to support the upper and lower ankle and allows the compression of this area for prevention and treatment of the wounds particularly, in the inner, lowers leg and the ankle area. This figure shows inner and outer supports, I-RIG-SUP and the O-RIG-SUP, that are made from rather rigid pieces, such as a shaped polymer or metal. The outer surface of these supports has zones of attachment means, such as hook fastener, ATM2S-A and ATM2S-B. These zones of attachment means allow a series of horizontal straps, similar to the band shown at C-BAND from FIG. 16 and other wider straps to wrap around them and hold the inner and outer rigid supports, I-RIG-SUP and the O-RIG-SUP, to squeeze them together, for further compressing the lower leg-inner ankle tissues in between. The lower ends of the inner and outer supports, I-RIG-SUP and the O-RIG-SUP are attached to each other by use of a piece of stretchable strap or a loop attachment means ATM1-S, that attaches to the inner hook fastener attachment means, I-ATM2S, and outer hook fastener attachment means, O-ATM2S, on a detachable, re-attachable basis. This method allows the distance between the two support pieces to be adjusted and match the width of the ankle area of a given user. The inner surface of the inner and outer supports, I-RIG-SUP and the O-RIG-SUP has at least one zone of hook fastener, attachment means, ATM2 that allows a foam pad shown at FIG. 16C to attach to the inner surfaces of the supports on a detachable, re-attachable basis.

These support units will hold one or two pads made from one or two kinds of foams, FOAM, which allows the ankle area to be compressed by the use of this pad. The foam pad may be made from:

1. A layer of rather non-compressible foam that stands outside of the ankle area.
2. A layer of rather soft foam that covers the ankle area and allows the foam to accept the shape for the ankle area.
3. A soft lining that will cover the inner surface of the inner foam and will stand on the wound dressing of the ankle.

The outer surface of the non-compressible foam has a zone of attachment means, ATM1-F that allows this pad to attach to the inner surface of the inner and outer supports, I-RIG-SUP and the O-RIG-SUP, on a detachable, re-attachable basis.

A series of stretchable straps will wrap around the supports to squeeze these two supports toward each other in order to compress the lower leg-inner ankle tissue in between.

Importantly, a flat, fluid-filled balloon attached to a measurement unit as shown at FIG. 16D may be placed under the inner support, and between another rather rigid units on the foam, FOAM. This unit will have proper shape and size to match the support unit, and will allow the pressure in the wound area to be known.

FIG. 16C shows schematically padding made from foam, FOAM that will be placed under the supports, to allow the compression of the wound area. The outer surface of the pad has a zone of loop-fastener attachment means, ATM1-F that allows this pad to attach to the inner surface of the inner and outer supports, I-RIG-SUP and the O-RIG-SUP on a detachable, re-attachable basis. Importantly, this unit has an opening that is designed to stand on the inner and outer bony prominence of the ankle joint. This is critically important, since this method will allow the soft tissue of the ankle to be compressed. Otherwise, the bony prominence of the ankle will prevent proper transmission of the compression to the soft tissue.

FIG. 16D shows schematically an inflation unit for use with the unit shown at FIG. 16B. This unit consists of a flat, fluid-filled inflatable balloon, IB, which is attached to a measurement unit, such as a gauge, G, by use of a three-way stopcock, TWS. The unit will be inflated by a pump, P, and after the optimum pressure inside the balloon is achieved the three-way stopcock can be closed and the pump and gauge removed. The inflatable balloon, IB, will be placed under the inner support, I-RIG-SUP a detachable, re-attachable basis. Importantly, the system may be a closed unit to allow the pressure to be noted all the time. An alarm unit may be incorporated to allow significant change of the pressure to be known. This unit also allows measuring the pressure on the leg supports shown in previous figures, thus by use of this unit the tension which the straps create in a particular length can be known.

FIG. 17 shows schematically the general view of a support unit similar to the unit shown at FIG. 16, except in this unit the body of the strap is made from a non-segmented fabric, or is made from a continuous fabric marked CSTR. This fabric is attached to the body of the support along one of its borders shown in the left side of this figure and it continues to wrap around the leg in one piece without cuts, but ends with three separate end pieces, EP-1, EP-2 AND EP-3. The end pieces have their own zones of hook-fastener attachment means, ATM2, shown at ATM2-1, ATM2-2 and ATM2-3 which allow these end pieces to attach to the outer surface of the support, SUP, on a detachable, re-attachable basis. Importantly, the value of this model is that it has a continuous body and does not leave any gap, open area or a line of compression on the legs, thus the leg will be universally covered. Also importantly, this unit is also chosen to show that a strap may have more than one ending. Importantly, note that the support, is like the support, SUP shown in FIG. 16 and is also made from a layer of fabric made of loop attachment means, ATM1 on its entirety that allows pieces of hook-fastener attachment means, ATM2 to be attached to it on a detachable, re-attachable basis. Note Importantly, other support means such as stretchable supports or combinations of stretchable and non-stretchable supports may also be used in these models as well. Also Importantly, supports made of other kinds of non-stretchable material with different attachment means may be also used for these purposes. Please note that the end pieces may have more than one zone of hook-fastener attachment means, ATM2 at their end similar to the unit shown at FIG. 4B for easier placement as explained in the text. Importantly, in this model the end pieces, EP1, EP2 AND EP3 may be made from ATM1 so that they can attach to zones of ATM2 on the support. Note in such model zones of hook-fastener attachment means, ATM2 may be double sided and they may be attached to the support, SUP, made of ATM1 on a detachable, re-attachable basis, but will function the same. The use of double sided attachment means, ATM2, has the advantage that allows the location of the ATM2 on the support to be adjusted.

Figure 18:
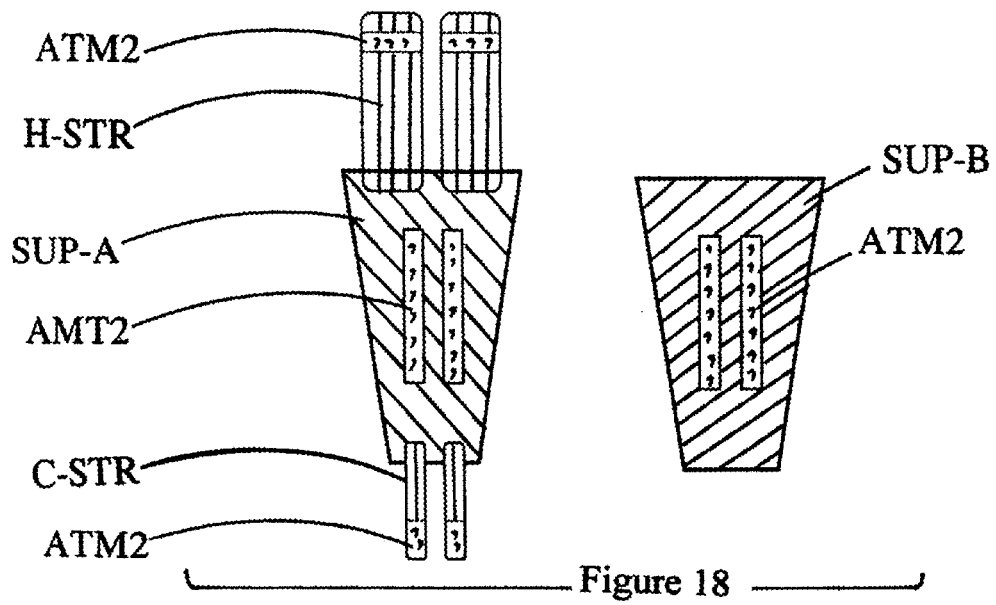
FIG. 18 shows two support units, SUP-A and SUP-B, and straps designed for the sides of head.

FIG. 18 shows the general view of a support unit designed for use on the head. This model also is intended to show how the supports may be more than one support; they may have different shapes and also can be placed at opposite sides of a place on the body and can also combine with multiple straps. This unit consists of two similar support units, SUP-A and SUP-B that will be attached to each other by use of straps; H-STR and C-STR. The supports have a trapezoid body as shown at SUP-A, with a wider, upper area for the head area and a narrower, lower area for placement on the chin area. Importantly, this support has a laminated body with an outer layer made of loop-fastener attachment means, ATM1, an inner layer which is a soft, fabric, lining to contact skin and a layer of foam in between. In the units shown here, the outer surface of the support, SUP, has two zones of long and narrow hook-fastener attachment means, ATM2, that allow the body of a strap made from Lycra™ with a smaller support on its end almost similar to the other straps shown in this application and is to be attached to the support on a detachable, re-attachable basis. This strap, shown in more detail at FIG. 18B, will attach to the unit shown at FIG. 18 on a detachable, re-attachable basis. This is important since the body of this particular strap is made from Lycra™ and allows such an attachment, which will keep the unit stable and prevent it from moving. The upper border of the trapezoid support, SUP-A, has two stretchable straps made from Lycra™, shown at H-STR. These straps attach the head areas of these two support pieces together on a stretchable, detachable and re-attachable basis. The free ends of these two straps have a hook-fastener attachment means, ATM2, that allow the ends of these straps to be attached to the outer surface of the other support, SUP-B, on a detachable, re-attachable basis.

The lower border of the support, SUP-A, for the chin area also has two stretchable, but narrower, straps made from Lycra™, shown at C-STR, that attach the chin areas of the supports SUP-A AND SUP-B together on a stretchable, detachable and re-attachable basis. The free ends of these two chin straps, C-STR, have small zones of hook-fastener attachment means, ATM2, that allow the ends of these straps to be attached to the outer surface of the second support, SUP-B, on a detachable re-attachable basis.

The second support, SUP-B, has a similar body, except that it does not have the H-STR and C-STR straps, since these straps will be attached to it on a detachable, re-attachable basis.

Figure 18A:
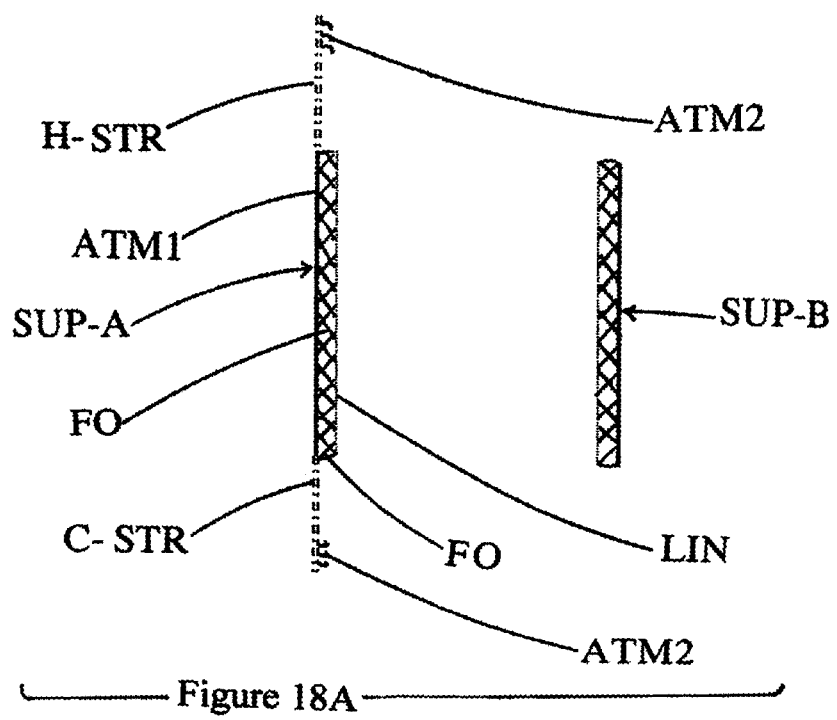
FIG. 18A shows the side view of the units shown at FIG. 18.
Figure 18:
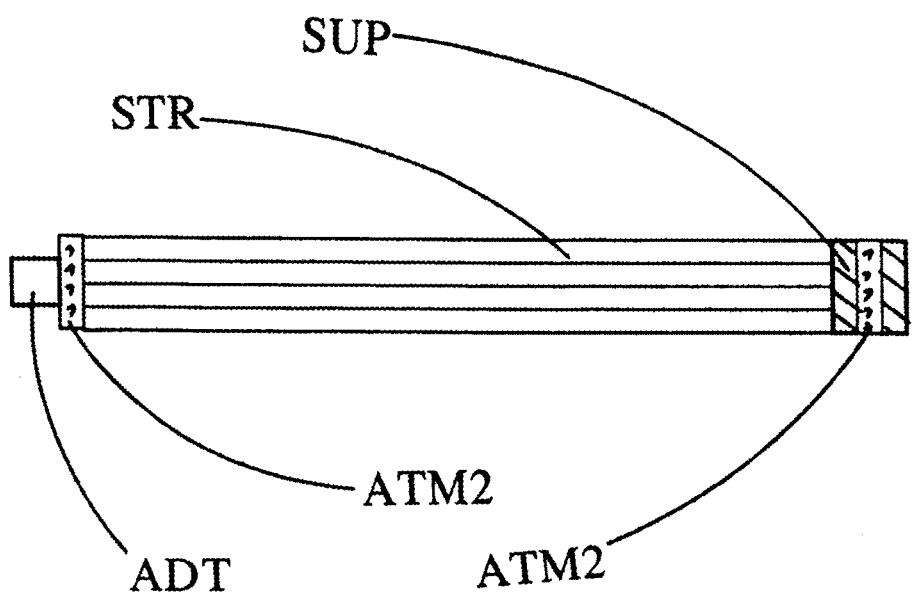

FIG. 18A shows schematically the side view of the unit for the head shown at FIG. 18. In this figure, the body of the support, SUP-A, is shown, and is a laminated support explained in text with an outer surface made from a layer of loop, fastener attachment means, ATM1, an inner layer, LIN and a layer of foam, FO in between. The elastic strap for the head is shown at H-STR and the elastic strap for the chin is shown at C-STR both of these have zones of attachment means, ATM2.

FIG. 18B shows schematically the general view of a complementary strap for use with the head unit shown at FIG. 18. This strap is a long, stretchable, ATM1 strap, STR which functions as loop fastener attachment means as well as explained in text that is attached to a support, SUP. The support has a zone of hook-fastener, attachment means, ATM2, on its front surface that allows the body of strap, STR, to attach to it on a detachable, re-attachable basis. The rear surface of the support, SUP of this strap, STR, may also have another zone of hook-fastener attachment means, ATM2, (which cannot be seen in this view) that allows the support, SUP, from this strap to attach to the outer surface of the support, SUP, for the head and chin on a detachable, re-attachable basis. Please note that the support for the head and chin has a laminated body with an outer layer made from a layer of loop-fastener attachment means, ATM1.

The free end of the strap, STR, shown on the left side of this figure has an adhesive piece, shown at ADT that allows the end of this strap to be attached to the outer surface of the strap, STR. This end may also have a zone of hook-fastener attachment means ATM2 to allow the end of the strap to attach to the outer surface of the strap on a detachable, re-attachable attachment basis when the outer surface of the strap allows. Importantly, note that this applicant has considered and introduced that the body of these straps allows an end of strap with a zone of hook-fastener attachment means ATM2 to attach to the outer surface of the strap on a detachable, re-attachable basis, and he has specified that his units made from Lycra™. have this capability to a degree and it can be increased by various means, such as double sided straps, having zones of loop fastener attachment means on the straps and different manufacturing and similar.

This combination of strap and head and chin support makes a valuable unit, since it allows a very stable and versatile unit for use for the wounds of the head and face, which is commonly difficult to wrap. This unit allows the head straps, H-STR, for the head site to be opened to adjust the size or tension of the unit or for the examination of the wound site. Also the chin straps, C-STR allow the size and the tension of the unit to be adjusted, as well. The strap, STR, goes horizontally around the head and allows the size of the strap and thus, the horizontal tension to be adjusted. Also, it allows the wounds in the occipital or the frontal part of the head to be checked. Importantly, the body of this strap may have other zones of attachment means, ATM1 and ATM2, as shown in FIGS. 8 and 8A.

Figure 19:
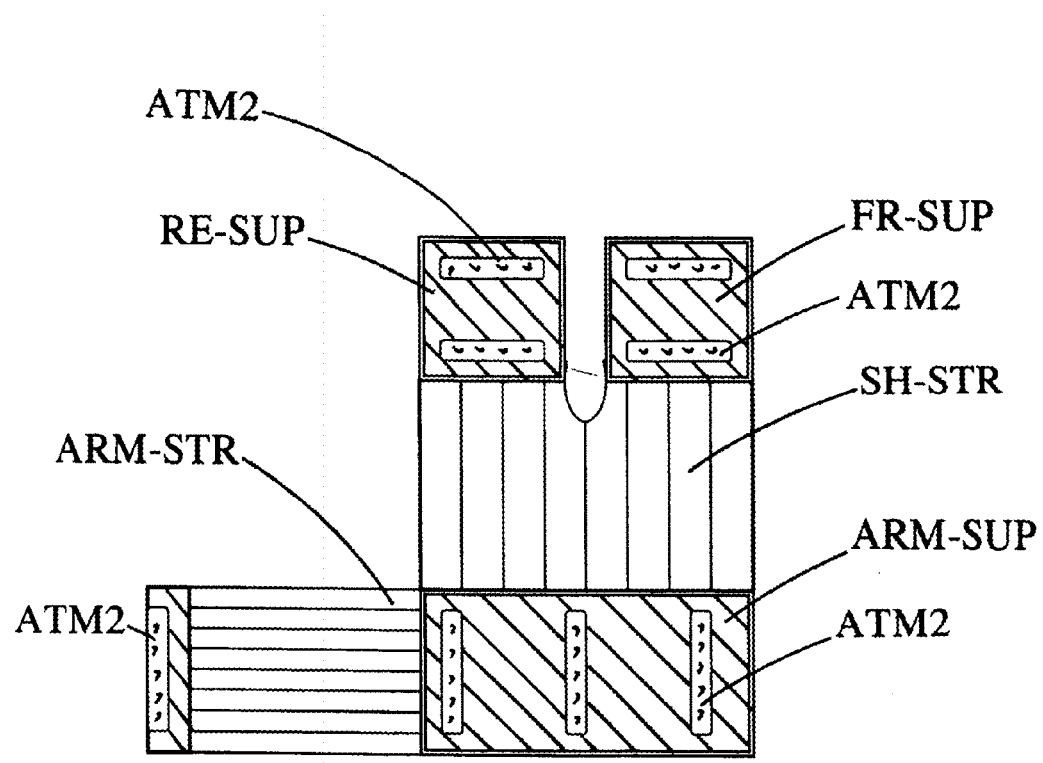
FIG. 19 shows a support means for shoulder.

FIG. 19 shows schematically the general view of a support unit for the shoulder. This model also is intended to show how the multiple supports may be used and be placed in different parts of the body and can combine with multiple straps for performing a dedicated job. This unit has a non-stretchable support unit shown as ARM-SUP that covers the outer side of the arm. This support has a laminated body with an outer layer made from a loop-fastener attachment means, ATM1, and an inner layer which is a soft fabric lining to contact skin and a layer of foam/sponge in between. In the units shown here, the outer surface of the support, SUP, will have at least two long and narrow zones of hook-fastener attachment means, ATM2. This allows the body of an arm strap, ARM-STR, made from LYCRA™, with a smaller support on its free end, to be attached to the arm support ARM-SUP. The strap, ARM-STR, is designed to wrap around the upper arm and attach to the surface of the arm support ARM-SUP on a detachable, re-attachable basis.

Another wider, stretchable shoulder strap, SH-STR, is also made from LYCRA™ and is attached to the upper border of the arm support ARM-SUP. The shoulder strap, SH-STR is designed to cover the shoulder and keep the dressing securely on it. Importantly, the stretchable body of this strap allows the shoulder to move easily. The shoulder strap, SH-STR, has two support pieces of its own that cover the front and rear (FR-SUP and RE-SUP) upper part of the chest. These two supports are made from the same material as the arm support, ARM-SUP, and also have zones of hook-fastener attachment means, ATM2, on their front surfaces. At the time of use, the front support FR-SUP is placed on the front of the upper chest and the rear support RE-SUP placed on the rear surface of the chest against the user's back. A strap STR shown at FIG. 20 goes in front of the chest and wraps in the armpit of the opposite arm, with one free end of the strap attaching to the outer surface of the FR-SUP and the other to the outer surface of the RE-SUP on a detachable, re-attachable basis.

Figure 20:
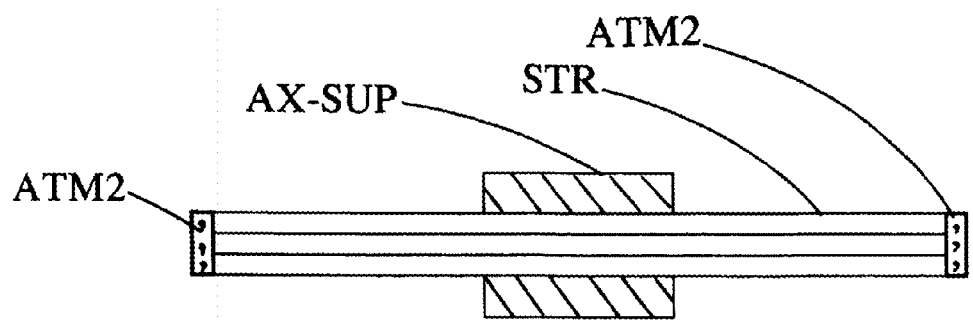
FIG. 20 shows a strap means for use with the unit shown at FIG. 19.

A piece of support, shown as axillary sup, AX-SUP, in FIG. 20 and made from same laminated material will go under the armpit and function as a stabilizer, preventing the strap from curling.

FIG. 20 shows schematically the general view of a strap for the shoulder support shown at FIG. 19. In this figure the body of the axillary support, AX-SUP, is shown. The front/outer surface of this support has a zone of hook-fastener attachment means, ATM2, which is under the strap, STR, and cannot be seen in this view. Both free ends of the strap, STR, have zones of hook-fastener attachment means, ATM2. As mentioned above, one free end of this strap will be attached to the front of the front support, FR-SUP. The strap will then be wrapped around the chest, and go under the opposite armpit to have its other free end attach to the outer surface of the RE-SUP on a detachable, re-attachable basis. The body of the axillary support, AX-SUP, covers the axillary area and will keep the strap, STR, in proper position, simultaneously preventing it from curling.

Figure 21:
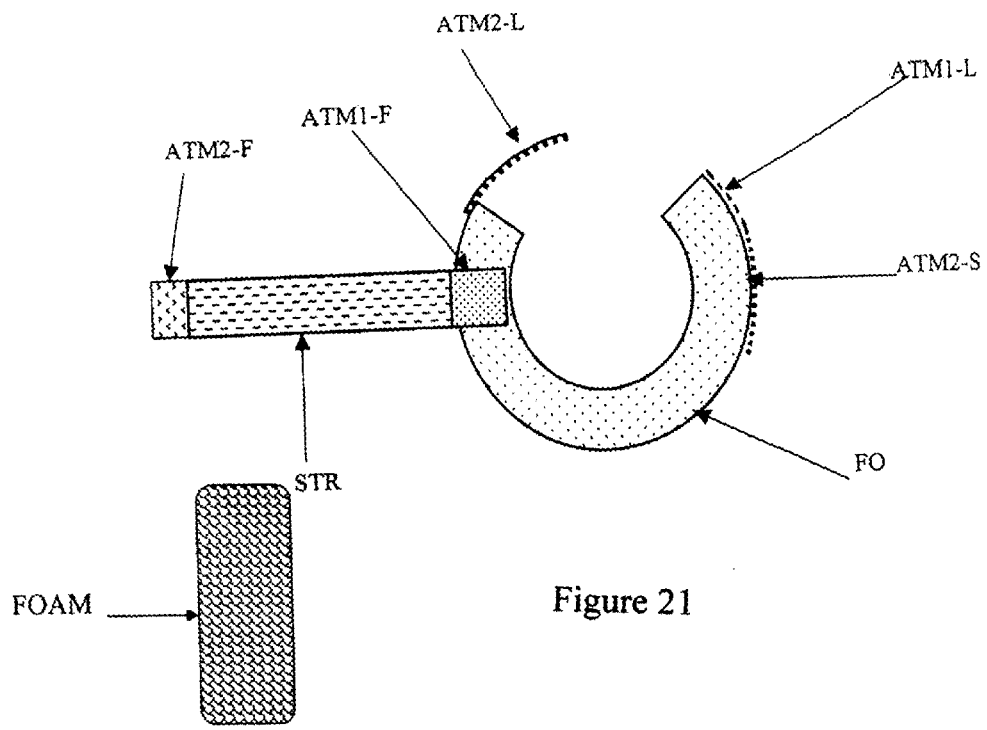
FIG. 21 is a doughnut shaped support unit designed to go around the lower leg close to the ankle.
Figure 22:
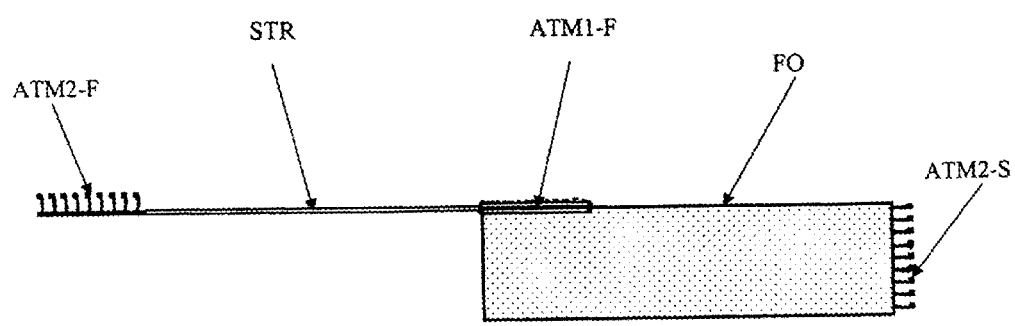
FIG. 22 shows the side view of the support unit shown at FIG. 21.
Figure 22:
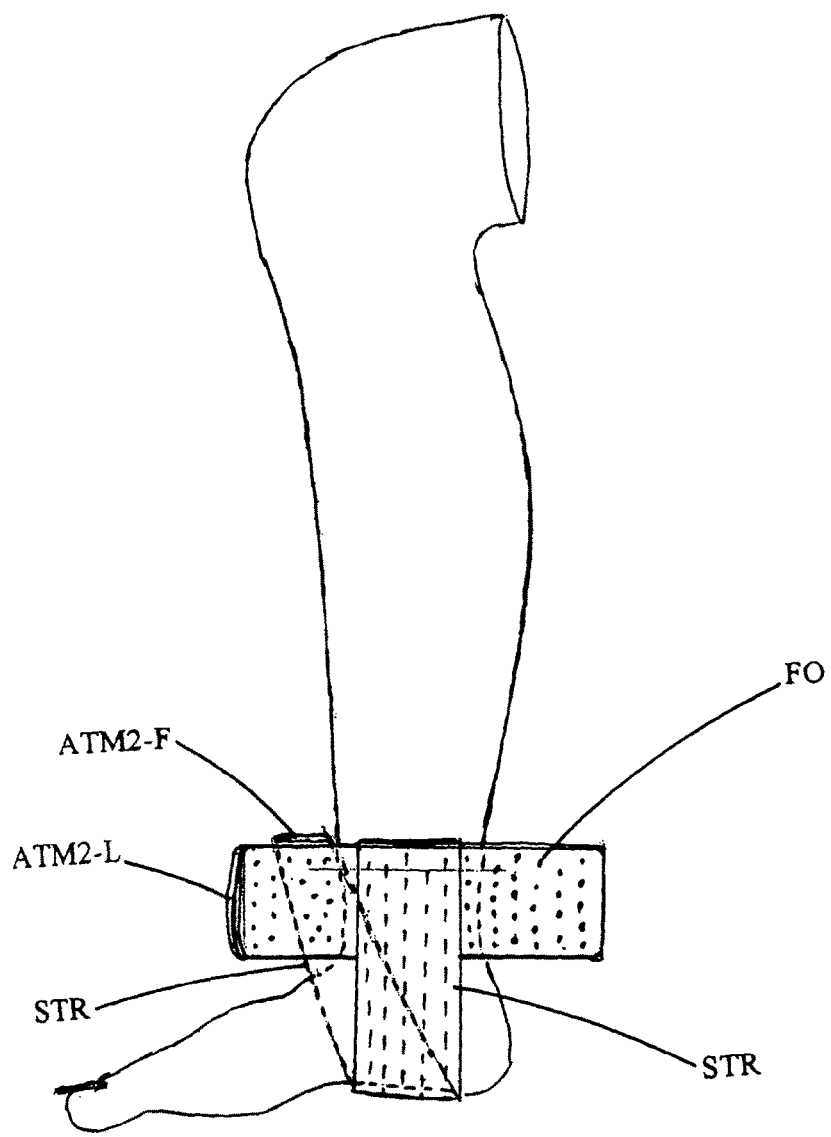

FIG. 21 shows schematically, the general view of a protective-support unit for the feet, designed to prevent pressure to the heel and the sides of the ankle by the mattress and sides of the bed. This unit consists of thick foam, FO, balloon/s or similar pad means which are shaped for being placed on the ankle area and to wrap around it, to make a doughnut-shaped thick unit. This unit has other properties, methods and means that allows the piece of foam FO or pad means to be held in place properly and it consists of: a pad means or a foam FO that has a circular shaped body as shown, which is sized so that when placed around the ankle it will prevent the foot from touching the surface of a mattress or objects close by. The first end of the foam has two zones of hook and loop fastening means, shown at ATM2-S and ATM1-L, which are shown in the right side of the figure and are placed at the ends of the foam FO. The other, the second end of the foam FO has a strap of hook-fastener attachment means, ATM2-L which is designed to attach to the zone of loop-fastener attachment means, ATM1-L, from the outer surface of the first end of the foam, FO, for making a doughnut-shaped thick foam around the ankle. A stretchable strap, STR, shown at left is attached to the body of the foam, FO, of this unit. Importantly, this strap, STR, is made of a double-sided, stretchable, loop fastener fabric such as LYCRA™ and has an free end with a zone of hook fastener attachment means, ATM2-F, shown at left. The inner end of the strap, STR, is attached to the side of the foam, FO, somewhat distant from the second end of the foam FO. At the site of attachment of the strap, STR, to the foam, FO, the strap, STR, has a zone of loop fastener attachment means, ATM1-F, facing away from the foam. Importantly, this zone of loop fastener attachment zone ATM1-F may be part of the foam FO or attached to it. The side view of this unit is shown at FIG. 22. At the time of use the foam, FO, will be wrapped around the lower leg above the ankle and held in place by attaching the attachment means ATM2-L, to the attachment means ATM1-L, and will make doughnut-shaped thick foam around the ankle. Importantly, the strap, STR, is sized to move down from one side of the ankle and wrap around the sole of a foot in a U-shape fashion and to move up in the other side of the ankle and attach to the zone of the hook attachment means ATM2-S located on the side of the foam FO. Then importantly, the strap, STR, will follow its move and will be pulled in front of the shin to attach to the zone of the loop fastener attachment means ATM1-F located on the foam FO, on a detachable, re-attachable basis, by use of the attachment means ATM2-F. Importantly, this method allows the elastic strap, STR, to create a reasonable tension in order to keep the foam, FO, in place securely. This method and means will prevent the foam, FO, from moving up in the leg and the prominences and shape of the ankle of the humans will prevent the foam, FO, from moving further down to the foot. Note, importantly that the body of the elastic strap STR is made so that it is not irritant to the leg and this is an advantage and makes the use of such a unit possible. Please note that the design of this unit is important since it will prevent the movement of the foam, FO, along the shin, up and down on the leg. Also importantly, it will prevent the rotation of the foam FO around the shin since the strap, STR, will prevent such a move. Also, importantly, the body of the strap, STR, allows it to attach to the surface of the foam, FO, by attaching to the attachment means ATM2-S, due to the special property of the strap. This plays a very important role in function of this unit. Importantly, the strap may have a Y shape with two end pieces, in order to allow one of the ends of the strap, to move in the rear part of the leg and the other end of the strap to move in front of the leg and to attach to the ATM1-F. This may give some more stability to these units.

Importantly, the strap may also have an attachment means to allow it to be attached to the hook of the leg elevator unit, described by this applicant in his previous applications. Please note that the foam, FO may have a cover made from fabric on its surface or to go over it in order to make it a comfortable unit and to allow the attachment means to be fixed on it.

The foam may have extra pieces attached to it to add thickness to the body of the foam, and to function as a further protective means. Also importantly, a similar piece of foam, shown at FOAM, may be attached to the body of the strap, STR, to stand on the sole of the foot and prevent the sole from touching the foot piece of a bed if such prevention is necessary.

The shape of the foam may vary and have more thickness in the bottom to prevent the heel from reaching the bed etc. This unit may be used with the units shown at FIGS. 16-17 to prevent pressure to the foot. In this case the unit may be used alone or be attached to the sides of the U-shaped supports. Importantly, instead of the foam, the body of this unit may be made from inflatable balloon(s), and similar, to function the same.

FIG. 22 shows schematically the side view of the unit shown at FIG. 21. In this view, the body of thick foam means, FO, is shown with a zone of hook-fastener attachment means, ATM2-S on the right side of the foam, FO. The cross-cut of the strap, STR, is shown on the left with the zone of the loop-fastener, attachment means, ATM1-F attached to the foam, FO and the zone of hook-fastener, attachment means, ATM2-F on its left border.

FIG. 22A shows schematically the side view of the unit shown at FIGS. 21-22 when placed on a leg. In this view, the body of foam means, FO, is standing around the leg with the piece of hook-fastener attachment means ATM2-L being attached to the zone of loop-fastener attachment means ATM1-L on the body of the foam FO. The strap STR is pulled down from the side of the ankle and wraps around the sole of the foot in a U-shaped fashion, then has moved up on the other side of the ankle and is attached to the hook-fastener attachment means ATM2-S on the side of the foam FO which cannot be seen in this view. Then the strap STR is further pulled in front of the shin and is attached to the zone of the loop-fastener attachment means, ATM1-F (not shown in this figure) due to the attachment of the attachment means ATM2-F. In this figure only the attachment means, ATM2-F, is shown.

Figure 23:
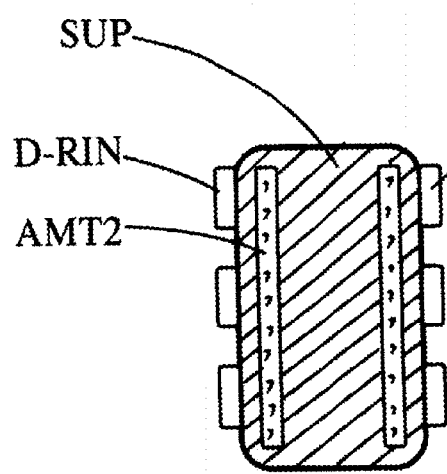
FIG. 23 shows a support unit means for the hip that also uses D-Rings. The straps are not shown.

FIG. 23 schematically shows the general view of a support unit for the hip. This unit consists of one non-stretchable, support unit shown at SUP, for the hip/joint area. This support has zones of hook-fastener attachment means, ATM2, on its front/outer surface that allows a strap with a loop-fastener attachment means, ATM1, to be attached to it on detachable, re-attachable basis. Alternatively, this support may have a series of D-Rings shown at D-RIN, on its sides in order to allow the free end of the straps to go through, make a U-turn, and attach to their own outer surface on a detachable, re-attachable basis. This method allows the length of the straps to be adjusted. In the models made, the applicant has used three straps with these units which worked well. This unit may have another similar support unit such as the support shown in this figure for being placed on the other hip joint in order to hold the straps in a stable position. A pad will be placed under the support for a uniform compression of the wound site and a better result. This pad may have different construction such as being made from foams, plus a relatively rigid piece, or similar, in order to allow a uniform compression to the wound site. The support may be made from a relatively rigid piece, to stand over the foam or a pad means.

Figure 24:
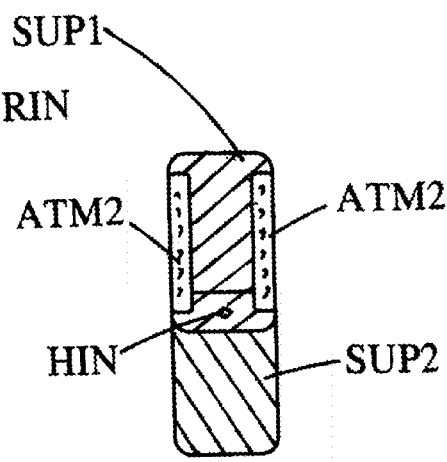
FIG. 24 shows a hinged-support unit means for the hip that allows the support to angulate.

FIG. 24B schematically shows a support unit for the hip that consists of hinging two support pieces so that it allows the person to bend the hip joint. In this view, the first support made from a non-stretchable piece; is shown at SUP1 and hinges to the second support, SUP2, at hinge HIM. The outer surfaces of the support pieces have zones of hook-fastener attachment means, ATM2. These zones are not shown for the second support, SUP2, to prevent a crowded Figure. These allow a series of the straps made from stretchable loop-fastener attachment means, ATM1, to be attached to the supports on a detachable, re-attachable basis. This support also may have a series of D-Rings on the sides. The supports shown at these two figures will hold a cushion pad made from foam covered with fabric that will be attached to the support unit on a detachable, re-attachable basis. This allows the cushion to compress the wound area. This unit may also have D-Rings as well or any other methods of attaching and controlling the straps to and on the support.

Figure 25:
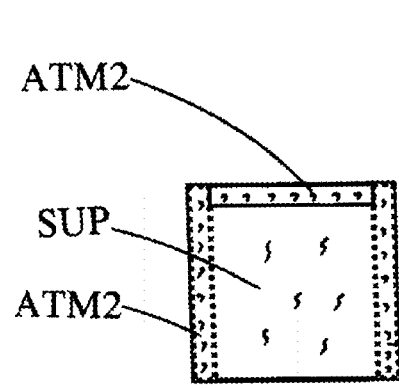
FIG. 25 shows a protective support unit for chest that prevents clothing from touching the wound.

FIG. 25 schematically shows a protective support unit for the chest or any other sites. This is designed to keep clothing away from the wound site of various forms, particularly after open-heart surgeries. This unit prevents clothing from touching the chest wound, and has a rather rigid and clear support piece that will be held away from the chest wall by use of walls made of foam pads. The outer surface of the support, SUP, has zones of hook-fastener attachment means, ATM2, on its upper and side borders. This allows the stretchable straps made from loop-fastener attachment means, such as STR-L explained in the text to be attached to it on a detachable, re-attachable basis. These straps of this unit consists of following:

1. A vertical strap that hangs on each side of the neck, both end pieces attaching to the zone of the hook-fastener attachment means, ATM2, which is located on the upper border of the support.

2. One or two horizontal straps which wrap around the chest and their own body or their end pieces will attach to the zones of the hook-fastener attachment means, ATM2, which are located on the borders of the support on its sides. Commonly, in the prototype models of this applicant, one strap around the neck and two from the chest area are used with this unit.

Figure 26:
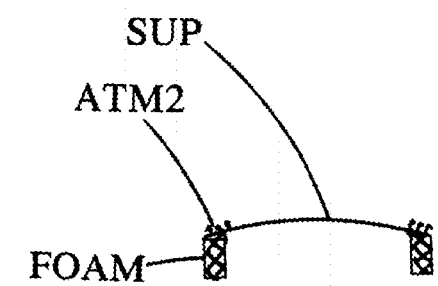
FIG. 26 shows the vertical, cross-cut view of the unit shown at FIG. 25.

FIG. 26 shows schematically the vertical, cross-cut view of the unit shown at FIG. 25. In this figure the body of the support, SUP, is shown and has a curve that keeps it away from the wound site. The upper/outer surface of the support has hook-fastener attachment means, ATM2, on its right and left borders. The lower surface of the support has two foam pads, FOAM, that will keep the chest support, SUP, away from the chest wall. The foam pads may also be placed in the other borders as well as desired.

FIGS. 27 and 28 schematically show the front and rear views of a support unit for the ear. The front view is shown at FIG. 27 and is rotated 180 degrees to show its rear image that looks somewhat similar to its mirror image at FIG. 28. This unit has a support, SUP, made from a laminated body, with an outer surface made of a layer of loop-fastener attachment means, ATM1, and an inner, soft lining for contacting skin with a thin layer of foam in between. In the process of use this support will fold along a line, FO-LIN. The body of the support, SUP, on the right side has an oval opening, O-OP, with a cut, CUT, on its lower pole. This opening allows the support to be placed around the base of the ear and prevent it from moving. The rear/outer surface of the support, SUP, on the left side has two zones of hook-fastener attachment means, shown at ATM2. A wide, elastic strap, made from LYCRA™, and shown at HE-STR, is designed to wrap around the head. This strap is attached to the body of the support, SUP, along the dotted-line, D-LINE. Importantly, the attachment line, D-LINE, is intentionally away from the edge of the support. This allows the band of attachment means, B-ATM2, to attach to the rear surface of the support, SUP, near the dotted-line D-LINE, so that the strap will finally wrap over this band.

At the time of use:

A. The oval opening, O-OP of the body of the support, SUP, will be placed around the base of the ear via the cut, CUT. This method will prevent the movement of the support after placement.

B. The rear half of the support, SUP, shown at the left side will fold along the folding line, FO-LIN, and cover the ear. The free borders of these two pieces will be held together by attaching the band of the attachment means, B-ATM2, to the rear surface of the support, SUP, adjacent to the D-LINE. The folded support holds the dressing of the ear on it securely.

C. Then the head strap, HE-STR, which is made from Lycra, will wrap around the head horizontally, on the front of the head, the temporal side and the occipital area respectively. So that ultimately, its free end will attach to the outer surface of the folded support, SUP, by use of the two zones of the attachment means, ATM2.

This method makes a secure and simple means of holding the dressing on the ear, which is commonly difficult. The body of the support may be made to have more foam and be thicker, or also to have a more protective, non-compressible body to avoid compression of the ear. The strap may also have a piece to go vertically and use the method shown for the head support.

Importantly, a small envelope made from fabric may be used to go over the wound of the ear and be held in place by this unit.

FIG. 29 schematically shows the side view of the unit shown at the previous two figures. This figure shows the support, SUP, the zones of the hook-fastener attachment means, ATM2, on its lower surface, (only one zone is marked), the folding line, FO-LIN and the head strap, HE-STR. Note that the point of the attachment of the head strap, HE-STR to the body of the support, SUP, which is marked at D-LINE is intentionally away from the very edge of the support. This is to allow the band of attachment means, B-ATM2 to attach to the rear surface of the support, SUP, near the D-LINE. This special design allows the head strap, HE-STR, to wrap over this band.

FIG. 30 schematically shows the general view of a support unit for the Pacemaker-Defibrillator Wound. This unit consists of a non-stretchable support unit, SUP, made of a laminated body with an outer surface made from a layer of loop-fastener attachment means, ATM1, and an inner soft lining for contacting skin, with a thin layer of foam in between. This support stands on the front of the upper chest and holds a pad, PAD, on the wound site. The pad, PAD, is attached to the inner surface of the support, SUP, on the upper half area of the support, by a hook-fastener attachment means ATM2. The body of the support on its upper half has a thicker body made from a folded support. In this area the support makes a U-turn and attaches to its own body, shown better at U-SUP in FIG. 31. Thus, this part has a body with a surface made of a loop-fastener attachment means, ATM1, on both sides. The support and attached pad will be held in the upper chest area by use of two straps made from laminated layers of loop-fastener attachment means, ATM1, providing both its outer and inner surfaces and with a thin layer of foam in between. The straps consist of the following:

a. A horizontal strap shown at H-STR that is designed to wrap around the chest and attach to the outer surface of the support, SUP, by use of a zone of hook-fastener attachment means ATM2. This is located on both ends of the strap or by use of an extra piece of a double-sided attachment means ATM2.

b. A vertical shoulder strap, S-STR, which covers the shoulder. The rear end of this strap makes a U-turn around the horizontal strap, H-STR, shown at U1, to attach to the surface of its own body. This will in turn keep the horizontal strap H-STR and the shoulder strap, S-STR, attached to each other on an adjustable basis, and is shown best at FIG. 31A.

c. The front portion of the shoulder strap, S-STR, stands in front of the support, SUP, and may attach to it by use of pieces of double-sided hook-fastener attachment means ATM2. The strap then moves down, and will wrap around the patient's wrist, where it makes a U-turn and moves up to attach to the rear surface of its own body as shown at U2 in FIG. 31A.

This unit:

1. Provides a compression to the wound site and prevents hematoma.
2. Holds the wrist of the patient in position and prevents it from moving.
3. Prevents other objects from reaching the wound site and causing pain.

Importantly, the size, shape and the makeup of the pads may vary. Also the nature of the straps may vary; the straps may be made to be:

1. Non-stretchable
2. Stretchable, elastic material.
3. Combination of non-stretchable and stretchable materials.

The stretchable straps may have their own attachment property such as STR-L or they may have pieces of attachment means attached to their body. Importantly, in these units the body of the support is primarily made from a material that has an outer surface made from a layer of loop-fastener attachment means ATM1 and its inner surface is a soft lining that would stand on the skin, with a thin layer of foam in between. This allows the shoulder and horizontal straps to be attached to the surface of the support in any area by placing a piece of a double sided hook-fastener attachment means, ATM2, between them. This design and method makes these units more versatile and stable.

Figure 32:
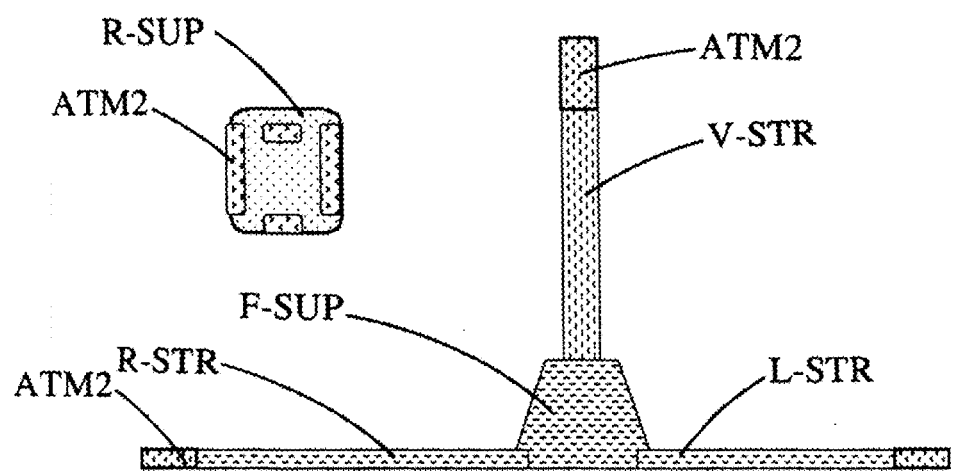
FIG. 32 shows a modified model of the unit shown in previous FIG. 30.

FIG. 32 shows a support unit similar to the unit shown in FIG. 30, except this unit has two complementary support pieces. The first support stands in the front of the chest and is referred to as the Front Support, F-SUP, and the second support stands on the back of the chest and is referred to as the Rear Support, R-SUP. The Front Support, F-SUP, stands on the wound site and will be kept in place through use of a strap in the right side, R-STR, another strap on the left side, L-STR and a vertical strap, V-STR that will come together and attach to the surface of the Rear Support, R-SUP. The free ends of these straps have pieces of hook-fastener attachment means shown at ATM2 that attaches to the surface of the R-SUP, made from the laminated body with an outer surface made of a layer of loop-fastener attachment means, ATM1, as explained earlier. The outer surface (the side that does not come in contact with the body site) of the support also has zones of hook-fastener attachment means, ATM2, which allows the body of the strap to attach to these attachment means on a detachable, re-attachable basis. Thus, the rear support, R-SUP, will in fact act as a catalyzer, allowing the ends of the straps to attach to each other easily. Alternatively, the free ends of the attachment means may be attached to each other by use of double-sided loop or hook fasteners, ATM1 and ATM2. The dressings or pads may be placed under the front or rear support. Importantly, this model makes the process of the dressing easier in some cases by preventing a crowded area in front. Importantly, the front support may have a body made of stretchable or non-stretchable layers.

Figure 33:
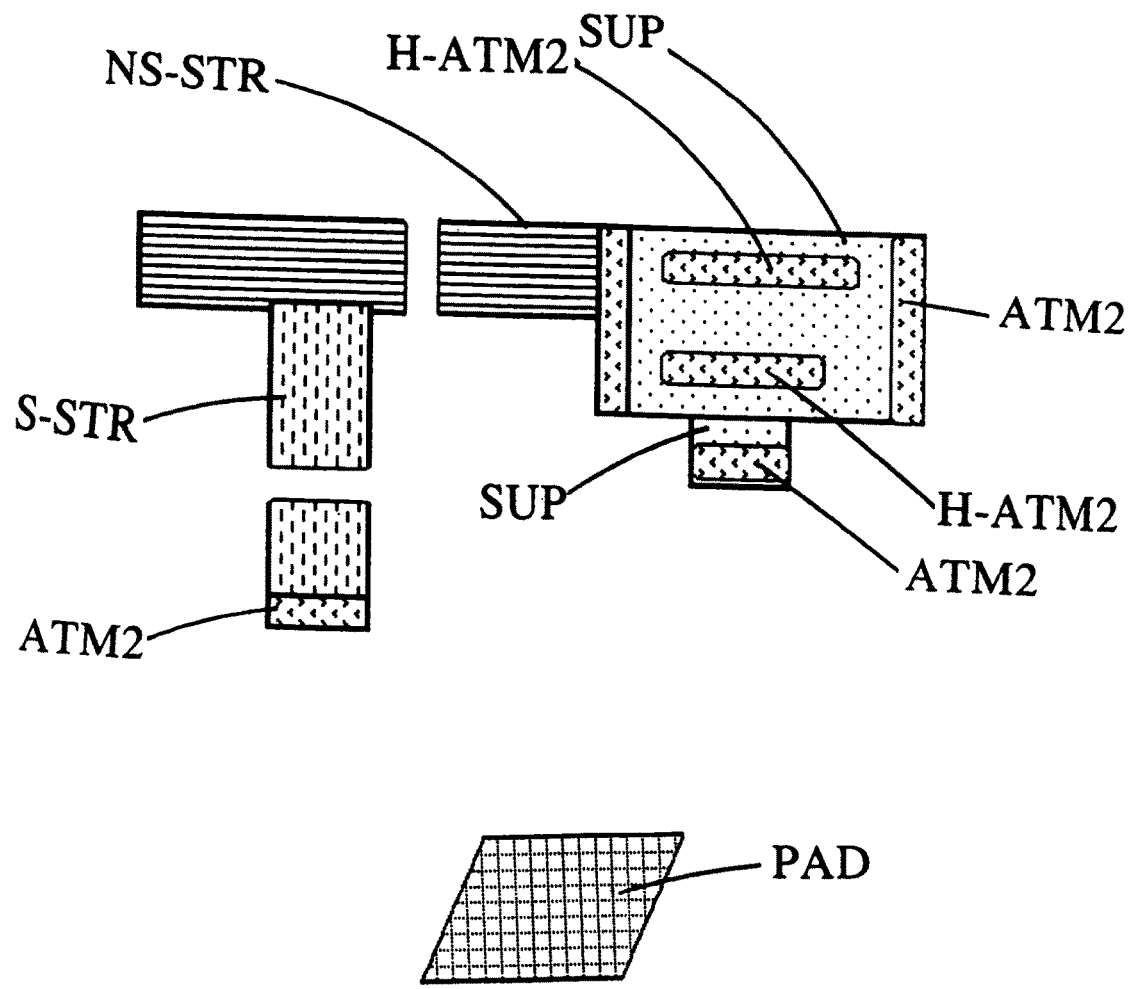
FIG. 33 shows a support means for use in the groin area.

FIG. 33 shows the general view of a support unit modified for use in the groin area to hold a pad over the wound in the inguinal area. A sample of such a pad is shown at, PAD, which has a trapezoid-shape and can be used after cases such as a hernia surgery in this region. This unit has a support, SUP, that extends and moves down to cover the inguinal area. The body of this support is made from a support means with laminated body, with an outer surface made from a layer of loop fastener attachment means, ATM1, an inner soft lining and with a thin layer of foam in between. It may also be made from any other manmade materials. The support, SUP, will be held in place securely by a non-stretchable strap, NS-STR, that is attached to the support, SUP, on one side in a permanent, or detachable, re-attachable basis, and allows the other end of the strap to wrap around the waist and function as a belt. The belt strap will hold the support, SUP, in a stable position. Please note that due to the extra length of the strap, NS-STR it is schematically shown with a cut in its length. A second, but stretchable, strap, S-STR, is attached to the body of the NS-STR, on a detachable, re-attachable basis, in the posterior surface of the NS-STR. This method allows the stretchable strap, S-STR, to more down the buttock area and pass the inner side of the groin, moving up and attaching to the horizontal hook-fastener, attachment means of the support, SUP marked at H-ATM2. This combination makes a secure unit for holding the support unit and compresses the pad, PAD, on the wound area in the groin. Importantly, when the stretchable strap, S-STR, is made from LYCRA™ it will:

1. Expand in the back to function as a comfortable layer of fabric

2. Shrink and roll in the groin area to limit its presence and the pressure to the sides of the groin.

3. Expand like a wing and cover a wider area in the inguinal area, to hold the support means, SUP, in a stable condition. Thus this design makes a very accommodating useful unit for this use. Importantly, the stretchable strap, S-STR, attaches to the body of the NS-STR on a detachable, re-attachable basis so that the position and location of such an attachment can be changed as needed. Importantly, the straps may be attached to the support unit independently, by having both their ends attached to each side of the support on a detachable, re-attachable basis.

Figure 34:
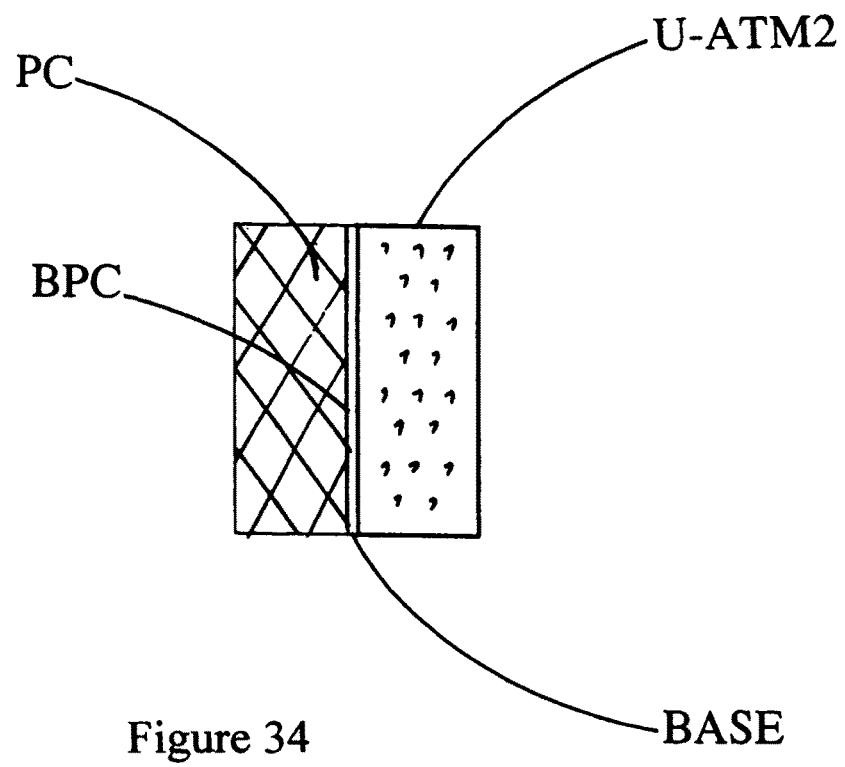
FIG. 34 shows an end piece with an adhesive zone and double-sided attachment means, U-ATM2.

FIG. 34 shows the front view of an end unit that will attach to the end of a strap in a desired spot and is designed for allowing the length of the strap to be adjusted, so that the strap will not be longer than needed and the end of strap to match the position of support. This unit has a rectangular, flat base, BASE, made from a layer of fabric or PVC with a zone of hook-fastener attachment means, ATM2 on its right side, placed both on its upper and lower surfaces. Here, the upper zone of attachment means, is shown on the right side at U-ATM2. A half of this unit on the left side is covered with a layer of adhesive, shown at ADH, at FIG. 34A, which is protected by a protective cover, PC. The inner edge of the protective cover is shown at BPC. The rear/lower surface of the base in the right side also has attachment means, L-ATM2, best shown at FIG. 34A. For better understanding please note FIG. 34A.

Figure 34A:
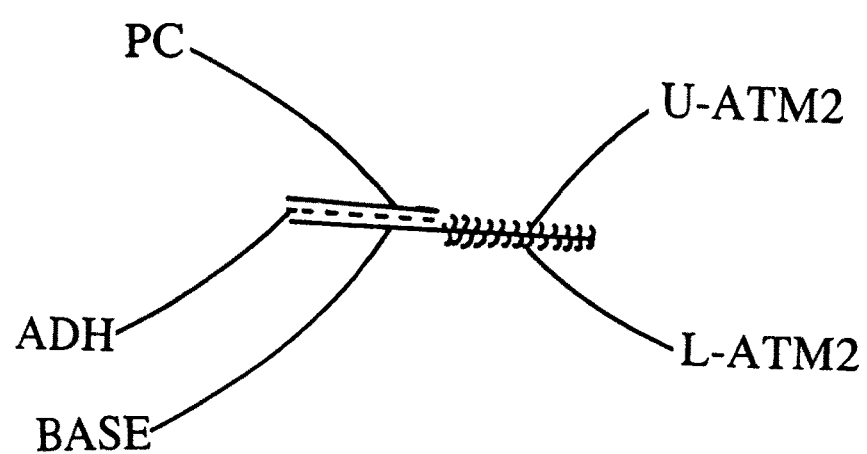
FIG. 34A shows cross-cut view of the unit at FIG. 34, with the ATM2 on its upper and lower.

FIG. 34A shows the cross cut view of the unit shown at FIG. 34. In this figure the unit has a base, BASE, made from a layer of fabric or PVC, with zones of hook fastener attachment means ATM2 on its upper and lower surfaces shown in the right side at L-ATM2 and U-ATM2. On the upper surface of the left half of the base, the layer of adhesive, ADH, with its protective cover, PC, is shown. At the time of use this piece will be attached to the top surface of a matching support by virtue of the lower attachment means L-ATM2. The stretchable strap will come from the right side of this unit and attach to the upper attachment means, U-ATM2, of this unit and proper length of the strap will be known. Then the extra piece of strap will be cut along the left border of the upper attachment means which is on the border of the protective cover. Then the user will remove the protective cover, PC, of this unit and adhere the base to the upper surface of the strap. This will make an end piece for the strap with a clean cut, and the combination will make a zone of attachment means, ATM2, on the lower end of the strap that can attach to the support on a detachable, re-attachable basis. This unit can be used in any of the above mentioned models when helpful—also it will be useful in the heel and shoulder units, etc. Please note that, instead of U-ATM2 the unit may have a zone of adhesive to allow the fabric to attach to it. And it will also allow the length of the strap to be adjusted.

At the time of use:

1. initially this piece will be attached in a proper position to the body of the outer surface of the support, SUP.

2. Then the strap will be pulled to attach to the ATM2 zone of this piece, which will be possible due to the capability of the strap made from Lycra™.

3. When the proper length of the strap is decided, then the extra piece of strap will be cut along the left border of the upper attachment means, ATM2 on the upper surface of this unit. Please note that at this point the strap is attached to hook-fastener attachment means, ATM2, from the upper surface of this piece.

4. Then the user will remove the protective cover, PC, and adhere the lower or base of this piece to the upper surface of the strap by use of the adhesive layer.

This combination will make:

a. the free end of the strap have a neat cut.

b. The combination make a zone of hook-fastener, attachment means, ATM2, in the lower surface of the free end of the strap that will be used to attach the free end of the strap to the outer surface of special supports that will accept this end. This will be very useful in units for use in various areas, such the heels and shoulder, etc.

The advantage of this unit is that allows a one-size unit to be used as a universal unit or will allow a better adjustment of the length of the straps.

Figure 35:
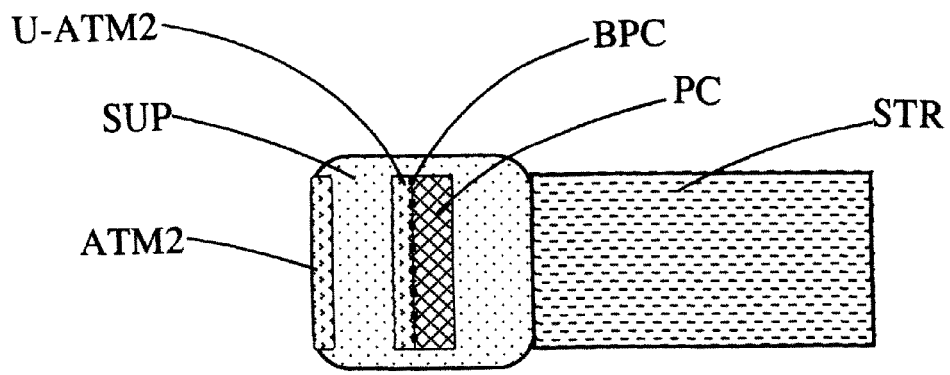
FIG. 35 shows an end piece unit shown at FIG. 34 attached to the front surface of a support, SUP.

FIG. 35 (also note FIG. 35A) shows the front view of an end unit shown at FIG. 34 which is attached to a support, SUP. This support has an outer surface made from a layer of loop-fastener, attachment means, ATM1. The strap, STR, is attached to the right border of the support. The outer surface of the left border of the support, SUP, has an optional long, narrow zone of hook-fastener attachment means, ATM2. The end unit is attached to the surface of the support, SUP, due to the attachment means, ATM2, on its lower surface; this part is shown better in FIG. 35.

Figure 35A:
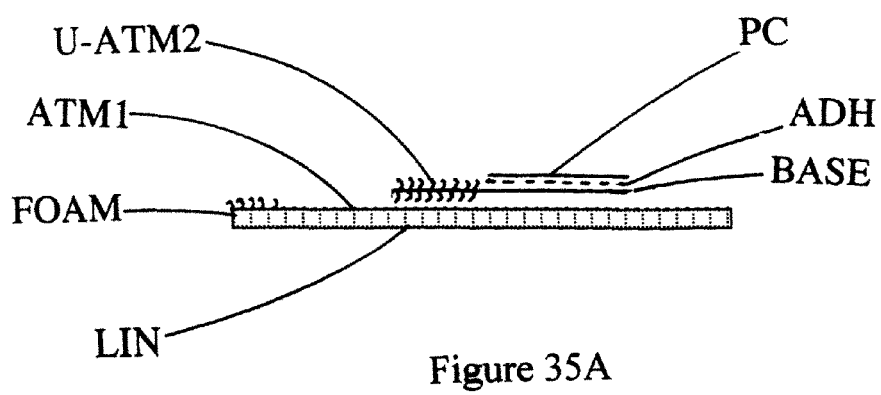
FIG. 35A shows a vertical, cross-cut view of the end piece attached to the upper surface of the SUP.

FIG. 35A shows the vertical, cross-cut view of the support, SUP, shown at FIG. 35 with an end piece close and parallel to it. The strap is not shown. The upper layer of the support is a loop-fastener attachment means, marked at ATM1, and its lower surface is a soft lining, LIN, with a layer of foam, FOAM is in between. The end unit is shown on top of the surface of the support, SUP, and consists of a base, BASE, made from a layer of fabric or a polymer, a zone of hook-fastener attachment means, ATM2 is on its upper surface, U-ATM2, and another zone of hook-fastener attachment means is in the lower surface which is not marked. The other segment of the base, BASE has a layer of adhesive shown at ADH, which has a protective cover, PC, on it. The method of use is explained above.

Figure 36:
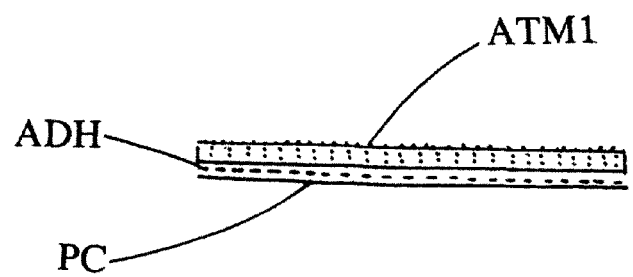
FIG. 36 shows a complementary unit that allows changing the surface of a vinyl support.

FIG. 36 shows the vertical, cross-cut view of a mating piece that allows the unit shown at FIG. 34 to be used with a support that is made from a material such as vinyl that does not have the loop-fastener means on its own surface. This piece has an outer surface made from a loop-fastener attachment means, ATM1, and its lower surface has a layer of adhesive shown at ADH covered with a protective cover, PC, on it. The method of use:

1. Initially, the protective cover, PC, of this mating piece will be removed and the unit adhered to the outer surface of the support, SUP, and thus this will modify the vinyl or similar supports, and allow the end piece ATM2 of the straps to be attached to the loop-fastener attachment means, ATM1, of this piece to function.

FIG. 37 shows the side view of a unit that allows the end of a strap to be attached to the outer surface of a support or the rear surface of the strap STR, itself. In this method the lower surface of the strap, STR, has a zone of hook-fastener, attachment means, ATM2, which is adjacent/attached to a longer zone of loop-fastener, attachment means, shown at ATM1. The lower surface of the loop-fastener, attachment means, ATM1, has a layer of adhesive, ADH covered with a protective cover, PC. This unit allows the user to adhere the loop-fastener, attachment means, ATM1, located at the lower surface of this unit to the outer surface of a support or a strap means on a desired place by removing the protective cover, PC and to use this unit on a detachable, re-attachable basis. Thus, the end of the strap can be attached to the support or its own surface on any desired area.

FIG. 37A shows the side view of a unit similar to the unit shown in the previous FIG. 37 except this model allows the end of a strap without ATM2 to be attached to any desired area of any support or a strap. In this model, the rear surface of a hook-fastener, attachment means, ATM2, has its own zone of adhesive ADH, which is protected by a cover, PC. The rest of the body of this unit is similar to the unit shown in the previous FIG. 37. This model allows the user to remove the protective cover, PC, from the lower surface of the loop-fastener, attachment means, ATM1, and adhere the combination to the outer surface of the support or the strap. The user will then wrap the strap, STR, over the support, or strap and adhere the end of the strap, STR, to the outer surface of the hook-fastener, attachment means, by removing the protective cover, PC. This will fix the hook-fastener, attachment means, ATM2, to the lower surface of the strap, STR, and loop-fastener, attachment means, ATM1, on the outer surface of the support or strap, STR, on a desired spot on a permanent basis. The user can then detach the zone of hook-fastener, attachment means, ATM2, from the loop-fastener, attachment means, ATM1, and re-attach it on detachable, re-attachable basis. Thus, any part of the strap, STR, can be attached to a support or the outer surface of a strap in any desired spot, thus the length of the strap can be decided as needed.

FIG. 38 shows a unit designed for use with the supports with long straps in which the strap wraps around a long limb such as arm or leg, and needs its free end to be secured. In this figure the end of such a strap STR is shown in the left side and has a zone of hook fastener attachment means on its rear surface shown at ATM2-R. A special shaped support means SUP1-A made from a laminated layer as explained in the text with an outer layer made of loop fastener attachment means ATM1 used. This support has a rectangular zone, a trapezoid zone and a long rectangular zone with a zone of attachment means ATM2 at its end. In the right side a short strap SSTR is shown and it has two zones of hook fastener attachment means attached to its rear surface shown as ATM2-RA and ATM2-RB. At the time of use the end of the main strap, STR, will be attached to the left side of the support SUP1-A and to its wide rectangular area by use of the attachment means ATM2-R to the outer surface of the support SUP1-A. Then the first free end of the short strap SSTR will be attached to the right side of the support SUP1-A and to its narrow rectangular area by use of the attachment means ATM2-RA to the outer surface of the support, SUP1-A. Then the second end of the short strap SSTR will be pulled and wrapped around the leg or arm or part of the body and, attach to the outer surface of the support SUP1-A by use of the attachment means ATM2-RB to make a circular ring and hold the strap system in place securely. At the end of this step the main strap STR will be pulled by use of the support SUP1-A and the short strap SSTR. Importantly, also or alternatively to strap SSTR in FIG. 38, the end of short strap, SSTR, can have a D-ring, DRIN shown in lower side of FIG. 40, so that the narrow rectangular end of the support SUP1-A can go through and attach to its own surface by use of the attachment means ATM2 at its end in order to allow the length of the whole unit to be modified. Note importantly, both sides of the support may have attachment means ATM1 properties. The D-ring is shown in this figure, with a strap, SSTR, attached to it and an end of the strap shown at attachment means ATM 2-R attached to it. Importantly, numbers of D-rings may be used in different areas of the straps in order to allow the length of the straps to be modified and match the support as needed, which is a known art.

FIG. 39 further shows strap means that allows the length of the strap to be modified by having zones of attachment means ATM1 on its outer surface so that the end of the strap can attach to one of these zones after wrapping around a limb. The free end of this strap will be attached to a support such as one shown at FIGS. 4 and 4A.

THE DETAILED EXPLANATION OF THE INVENTION

Addressing a Main Issue.

Before proceeding with more details of the units presented in this application the applicant wishes to bring a very important issue into consideration. The fact is that due to years and years of R&D this applicant has made its contribution to humanity by many of such units which some are presented to USPTO by the applications specified in the list of priorities. He believes that the teachings in those applications are so powerful that they allow many other versatile units to be made. To prove, consider the unit shown at FIGS. 7, 7A which was previously introduced to USPTO, except in the previous model the attachment means ATM2 On the support was fixed rather than removable. This unit can be easily modified to make the units shown in FIGS. 4 and 4A, only by removing the attachment means ATM2 from the support and making the stretchable strap non-functional as far as the loop fastening attachment means is concerned. The same is also true in models shown in FIGS. 10A and 10, FIGS. 11A and 11 and many other similar models, pointing out that many new models may be made simply by modification of this applicant's previous units. In fact only thing he did to make the new figures such as the one shown at FIG. 11 is to remove the attachment means ATM2 from the FIG. 11A, and he did that for making units in figures FIGS. 14 and 15. In other words the models shown at figures such as FIGS. 14 and 15 are exactly from his previous application documented in USPTO except the attachment means ATM2 from the supports are removed. Thus he wishes to point to one generic issue that by use of his teaching it is very easy to make many versatile units by simple modifications. This application is to do the same and add some more, except the added ones are by the person who has made the originals.

Definitions, please note that some abbreviations are utilized in this application many times, to save time and simplify understanding, for this reason please note the following.

ATM1, refers to all loop fastener attachment means, i.e. loop fastener attachment material, or those which functions such.

ATM2, refers to hook fastener attachment means, i.e. hook fastener attachment material, or those which functions such.

SUP, refers to support means, a layer designed to stand on a limb or part of body.

STR, refers to any types of stretchable straps.

STR-L refers to a stretchable fabric which is also capable of functioning as a loop fastener attachment means ATM1, and thus it can be directly attached to hook fastener attachment means.

DS-ATM2 refers to a piece in which both sides function as hook fastener attachment means, ATM2.

This application introduces different and improved versions of this applicant's inventions which were previously introduced to US PTO. These models are based on his years and years of R&D. The applicant here shows basically how his previous inventions may be modified to make similar units to work about the same and to make the process of body and limb wrapping and wound dressing simpler, faster and easier in humans and animals. The applicant's extensive R&D shows models that allow practically the coverage of wounds in almost all parts of the body. These inventions practically eliminate or reduce the use of adhesive tapes on skin and prevents the pain and problems related to their use. Besides wound dressing these units also have other uses, such as allowing a limb or part of a body to be wrapped tight. To illustrate these issues he explains the prototype model, shown at FIGS. 4 and 4A, and compares it with the applicant's previous invention shown at FIGS. 7, 7A and 7AB to appreciate the differences, and how easy it is to interchange them. The new units shown at FIGS. 4 and 4A is made from:

1. A support unit.
2. A stretchable strap means.
3. Means that allows the strap to attach to the support on a detachable, re-attachable basis.
4. And means, which allow the shape of the support to be modified for being used in different areas of the body for special reasons.

The basic unit is very simple, as shown in FIGS. 4 and 4A. It is made from combination of a stretchable strap STR and a support SUP which allows this unit to be wrapped around a limb. The end of the strap, SIR, has at least one hook fastener attachment means at its rear surface shown at ATM2-RA and ATM2-RB that allows the end of the strap to attach to the outer surface of the support on a detachable, re-attachable basis. The support, SUP is made from a loop, fastener attachment means, ATM1, as shown in FIG. 1. However, it may be made from a stretchable or a non-stretchable material which functions as a loop fastener attachment means ATM1. Commonly the support as shown in FIG. 1, has a rectangular- or a trapezoid-shape, and it is used to cover a limb, part of the body or a wound. The support can be used to hold a gauze pad or wound dressing, or a medicine pad in place. This support uses at least one stretchable strap STR as shown in FIGS. 4 and 4A which attaches to the support from one side, wraps around a portion of a body, comes and attaches to the support on a detachable, re-attachable basis, by use of attachment means. Please note that in this application the hook, ATM2- and loop, ATM1- fastener attachment means are utilized significantly and are mentioned very frequently too. Please note that the attachment means are not limited to these two types and any other types of attachment means may be also used in these units when feasible.

The Supports.

The supports as shown in figure FIG. 1 and FIG. 4 have a rectangular or trapezoid shape or similar and consist of the following:

a. They can be made from a non-stretchable material, such as a fabric, a vinyl, a shapeable material such as aluminum, other metals, PVC's etc. with having attachment means on its outer surface that allows the straps to attach to them on a detachable, re-attachable basis.

b. They can be made from a stretchable material, with attachment means outside that allows the straps to attach to them on a detachable re-attachable basis. This allows the support to stretch and fit the wound site best when needed, such as over the joints or when the tension in the area is needed.

c. Combinations of non-stretchable materials and stretchable materials may be also used in various forms to make support units for certain areas, such as general use or when tension in the area is needed.

Importantly the outer surface of this support will have one kind of attachment means or another for allowing the end of the strap to be attached to the body of the support either on its surface or on its borders. The prototype of these units shown at FIG. 1, shows a model that in which the surface of the support is covered with a loop fastener attachment means ATM1. Alternatively it may be covered with a hook fastener attachment means ATM2 or similar. Also in the prototype model, the support is made from a non-stretchable material referred as the support means1, SUP-1, which is made from a non-stretchable fabric, with an outer surface made of loop fastener attachment means, shown at FIG. 1 at ATM1 that stands away from the skin of the user and is specified as loop-fastener attachment means ATM1. Thus it allows the end of the strap with a zone of hook fastener attachment means, ATM2 to attach to any part of the outer surface of this support on a detachable, re-attachable basis. The support layer may have a soft lining for skin. Commonly, the support is made from a laminar material, consisting of three layers, an outer layer shown at FIG. 1A at ATM1 which is made of a layer of loop fastener attachment means, an inner layer, shown in FIG. 1A at IN-L made of a soft, fabric that will stand on skin, and a layer of foam in between these layers. In FIG. 1 the general shape of the support, is shown as rectangular shaped and is covered with a loop fastener attachment means ATM1. Importantly, this basic support means has many uses and can be used with any stretchable strap means which is attached to one end of the support by its first end and has a zone of attachment means on the inner surface of its second/free end which is capable of attaching to the outer surface of the support means on a detachable, re-attachable basis as shown in FIGS. 4 and 4A. The support may have different shapes and sizes and can be used in many different parts of bodies of humans or animals, by placing the support on a limb with the strap to wrap around the limb and attach to the outer surface of the support on a detachable, re-attachable basis, for holding a wound dressing, or pressing the limb or protecting the limb or for any other purposes. This basic support means allows other modifications and options, for example it allows having zone of attachment means ATM2 on it or by use of a zone of double-sided attachment ATM2, DS-ATM2 attached to its outer surface, as shown in FIGS. 4C, 4D and 7. This modification gives even more significant value and allows a strap means that has a body made of, or with, or having zones of loop fastener attachment means ATM1 to be attached to the zone of attachment means ATM2 on the support on a detachable, re-attachable basis and provides many options of use. Such a support may be used with different strap means, either a stretchable strap means STR or stretchable strap means with a body which also functions as a loop fastener attachment means STR-L as shown in FIGS. 3, 3A, 7 and 7A. This applicant has previously introduced to the USPTO that the fabric made from Lycra™ will function as such. The research of this applicant has shown that when the strap is made from Lycra™ it directly attaches to the zones of hook attachment means ATM2 of the support on a detachable, re-attachable basis, and he calls this strap as STR-L. This makes a very particular unit that allows the attachment of such a stretchable strap means having end pieces or zones of hook-fastener attachment means, ATM2, to occur on a double-function basis as follows:

1. The body of strap means, STR-L, which functions as a loop-fastener attachment means, ATM1, will attach to the zones of the hook-fastener attachment means, ATM2, located on the support as shown in FIGS. 4C, 4D, 7 and 7A on a detachable, re-attachable basis.

2. The zones of the hook-fastener attachment means, ATM2, from the ends of the strap shown at ATM2-R in same FIGS. 4C, 4D, 7 and 7A will attach to the outer surface of the support, SUP-1 (with an outer surface made of loop fastener attachment means ATM1) on a detachable, re-attachable basis. This makes very useful units, since they are very easy to handle and are stable and can be used in many models. The body of a support made of attachment means ATM1 also allows any other pieces or means such as information pockets, suction bulbs, different supports and straps which have a zone of matching attachment means of hook fastener attachment means ATM2 to be attached to the outer surface of the support on a detachable, re-attachable basis. Importantly, and alternatively, the strap means can be made from any stretchable fabric or material with zone/zones of hook fastener attachment means ATM2 at its body or ends that allows only the end or the zones of attachment means ATM2 of the strap means to attach to the support on a detachable, re-attachable basis. An example of this is shown at FIGS. 4, 4A and 4B. Note in these models it is advantageous to have two zones of attachment means ATM2 at the end rather than one for the reason that makes it easier to be handled.

Importantly, the supports may be also made from a layer of hook-fastener attachment means, ATM2, on its surface. The applicant refers to these as support means 2—(type II support means), SUP2, which are less popular. This makes a support means that allows the attachment of a stretchable strap made from a loop-fastener attachment means, ATM1, or with end pieces of loop-fastener attachment means, ATM1, to attach to the outer surface of type II support means SUP2 on a detachable, re-attachable basis. The surface of type II support means may have zones of attachment means ATM1, to also allow a double attachment as follows:

1. The zones of the loop-fastener attachment means, ATM1, from the ends of the strap will attach to the outer surface of the Type II support means on a detachable, re-attachable basis.

2. The body of the strap, made from a loop-fastener attachment means, ATM1, such as Lycra™ will also attach to the zones of the hook-fastener attachment means, ATM2, of the outer surface of the support means on a detachable, re-attachable basis as well. This is less Popular by this applicant since the surface of the support will be unfriendly and can be rough.

Note the Attachment of the first end of the strap to the support means can be on a detachable re-attachable basis.

Use of Double-Sided Hook Fastening Attachment Means on these Supports.

This applicant has introduced use of what he refers to as "double-sided hook fastener attachment means"; DS-ATM2 as shown in FIGS. 2 and 2A. This unit has a flat body MAT with both of its surfaces having zones of hook fastener attachment means; ATM2 on it. This is a very useful unit for use with the support SUP1 with an outer surface; covered with a loop fastener attachment means ATM1. As the applicant mentioned, it allows a piece of double-sided hook fastener attachment means DS-ATM2 to be cut to pieces of various shapes and be attached to the surface of the support; SUP on a detachable, re-attachable basis, when such support is made with an outer surface made from loop fastener attachment means, ATM1, as referred to as support 1, SUP-1. FIGS. 2 and 2A show the body of double-sided hook fastener attachment means DS-ATM2 has matrix shown at MAT that allows the hook fastener attachment means to be attached to it. The matrix may be made from different materials, such as a layer of adhesive, a fabric, vinyl, PVC's, sheet of metal etc. Importantly, the matrix can be a rigid material; the advantage of a rigid matrix is that it prevents the shape of the double-sided hook fastener attachment means DS-ATM2 from bending in some direction, shrinking or changing. The double-sided hook fastener attachment means DS-ATM2 may be shaped in any desired fashion, which is important since after attachment it will change the shape of the support. For example when a double-sided, hook fastener attachment means as shown in FIGS. 2 and 2A made with a rigid matrix is attached to the support, SUP1, made from loop fastener attachment means it will prevent the support from shrinking longitudinally and also will prevent the strap from moving down. Note importantly, when the body of the support or ATM2 on it is not rigid the support will gradually loose its shape and shrink due to the movement of the muscles under the support, shape of the limb such as the leg, weight of straps etc., which can be prevented by use of rigid double-sided hook fastener attachment means DS-ATM2 or a rigid support—note such prevention is very important. Importantly, the strength or the degree of attachability of each of these zones of hook fastener attachment means of a double-sided hook fastener attachment means DS-ATM2 may vary to make them weaker or stronger, so that for example the attachments to the support can be stronger and to the straps weaker. In the model shown at FIGS. 2 and 2A the weaker attachment means ATM2 is shown at ATM2-W and the stronger hook fastener attachment means at ATM2-S so that when this piece is attached to the support and the strap at the same time and the strap is being pulled away from the support, the strap will be detached from the attachment means ATM2-W but the attachment means ATM2-S will continue to be attached to the support despite being pulled away by the strap. This double-sided hook fastener attachment means DS-ATM2 may be also made in a shape of a rope or a thin cylinder with attachment means ATM2 around their outer surfaces, that can roll on the surface of the support means made of attachment means ATM1, but still will be attached to the support on a detachable, re-attachable basis. The half of the surface of such cylinder may have a weaker attachment means ATM2 such as ATM2-W and the other half to have a stronger hook fastener attachment means such as ATM2-S.

FIG. 3B shows schematically, the general view of a support unit similar to the unit shown at FIG. 1, which has two pieces of double-sided attachment means such as one shown in FIG. 2 attached to its surface and has a long stretchable strap made from STR-L with a zone of hook fastener attachment means ATM-R at its rear surface. Such a unit may be placed on the front of the leg and it allows the strap to wrap around moving up wrapping obliquely so that when it reaches to the end of the support, the end of this strap will attach to its own rear surface by use of attachment means ATM2-R.

Importantly, in this case the body of the double-sided hook fastener attachment means DS-ATM 2 is made from a relatively rigid piece of PVC so that it would not allow the body of the support to shrink and be moved down due to the shape of the leg, movement of the muscles and force of gravity, which is a very important function.

Note, that importantly, a similar zones of double-sided hook fastener attachment means DS-ATM2 may be also placed horizontally on the support to prevent the body of the support from shrinking in a horizontal direction. Note the reason the body of the double-sided hook fastener attachment means DS-ATM2 is wider than of the attachment means ATM2 is intentional and important since it prevents the edges of the attachment means ATM2 from attaching to the side of the surface of the support and be disfigured, and also a wider body will be more stable. This model is a very important and useful unit.

Continuation of Explanation of Supports.

Stretchable support means. Importantly, it is possible to make supports from a layer of stretchable attachment means such as stretchable loop fastener attachment means such as Lycra™ shown at FIG. 3 so that it allows the ends of the strap means to be attached to it and yet to stretch as well. An example of this unit is shown in FIGS. 1D and 1F. With a support made of a loop fastener stretchable fabric, this allows the support to function both as attachment means ATM1 and also to stretch.

Importantly, the support means may be made with a combination of stretchable attachment means such as stretchable strap means made from Lycra™ and parts of non-stretchable attachment means such as loop fastener attachment, ATM1, so that it can stretch and function as a loop fastener attachment means too. An example of this unit is shown in FIGS. 1G and 1H, with zones of non-stretchable attachment means such as loop fastener fabric in the sides shown at ATM1 and a zone of stretchable attachment means, shown at S-ATM1 in the middle. This method allows both of these zones to be used as attachment means ATM1 yet the support to stretch as well.

The support means may have zones of hook fastener attachment means at ATM2 attached to them in various forms such as fixed or removable such as double-sided ATM2, as shown at FIGS. 4C, 4D, 7 and many other figures in this application. The attachment of the end of the strap to the support means can be fixed or on a detachable re-attachable basis.

The support SUP-1 with outer layer of attachment means ATM1 also allows any other pieces or means which have a zone of hook fastener attachment means ATM2 to be attached to it on a detachable, re-attachable attachment basis. The support may have a door, to allow the door to be opened so that the wound site can be seen and the wound dressing to be changed without disassembling the whole unit. The support may hold various objects such as suction bulbs attached to its surface.

Shaped Supports.

Importantly, the support means may be modified to have different shapes or its shape may be modified by adding or using means, components or skeleton for ending in desired shapes. Some examples of these methods and means are as follows.

The supports may have various shapes due to their own skeleton/s, or structure, or alternatively a shaped unit or a skeleton may be attached to the outer or inner surfaces of the support, for such modification so that the final shape will emerge to fit easily in a particular place or for a particular usage. An example of a shaped support is shown at FIG. 1B. In this model the support has shape of a half of a cylinder, so that it can be placed easily on a limb such as arm or leg or any other desired place. This goal may be also achieved by having one or more shaped bodies attached to it, for example a spring that can stretch and coil as shown in FIG. 1C. In this model, a C-shaped spring will be attached to the outside of the support to give a curved, half cylinder body. The body of the support may be capable of being shaped such as by being made from aluminum or similar so that it can be shaped to be placed on forearm, arm or leg with a reasonable steadiness, to allow the straps of this unit to be pulled and attached to the outer surface of the support. Such placement will make the handling much easier. Consider a wounded person, an aged person, or a person with neuro-muscular problems who has difficulty in placing and holding a flat support on a limb to note how a shaped support will make such placement significantly easier. Please note that in FIG. 1B, the straps are not shown but they will be attached as shown in other figures. Importantly, means that gives shapes to the body of the supports may be an attachable, detachable piece/s of a spring, shaped metal or a semi-ring or similar that can be attached to the support on a detachable re-attachable basis by use of different attachment means. An example of such a shaped support means is shown at FIG. 1C. These pieces can be attached to the outside, or to the inner part of the support's body to modify the shape of the support and will have different make ups or shapes for doing the job. The use of the unit shown at FIG. 1C will give the support the shape of a semi-cylinder to stay around a limb and then to be wrapped easily. In other model the support may have the shape of a cup or be curved to have a matching shape, note such an example at FIG. 1D. The shape and curvature of a given unit will be designed to stay on the area which is needed such as heels, the knees, and elbows, around the elbow, the head and similar. Importantly, the unit shown at FIG. 1B may be modified further by making its body rigid or adding a rigid layer for protecting the underlying tissue from the incoming objects. Thus these units would be protective and very useful in patients who have tendency for bumping their shins against objects, such as elderly or patients with neuromuscular problems who have a wound.

Importantly, the size, shape, the material used, the thickness and other important variables of such shape-givers or skeletons may vary to allow different units to be made for different uses.

Also importantly the support may be made from a non-stretchable layer such as vinyl, PVC or metal and to have zones of attachment means on it. In order to allow the incoming straps to be attached to them on a detachable, re-attachable attachment basis.

Use of these Supports as Splints.

One important aspect of the shaped support is that it allows them to be used as splints. In these units the body of the support is modified to be in the shape of a splint, except the outer surface of the support or the splint has a zone of attachment means such as attachment means ATM2 that allows the body of the strap to attach on a detachable re-attachable basis. Although a stretchable strap will be used with these units, the most useful strap would be a strap made of the stretchable loop fastener fabric, STR-L, which is capable of attaching to the attachment means of the support ATM2 on a detachable re-attachable basis directly. The splints may be made from one single shaped piece or from a combination of two or more pieces. The body of the splint can be made from PVC, a layer of metal such as aluminum or similar, which can be shaped so that the shape can match the area which is being used. For example in the arms, legs, elbow or ankles it will be like a cradle that allows the hand, elbow, the leg or the ankle area to sit inside it comfortably. The outer surface of the splint as shown in FIG. 1CD has an attachment means such as hook fastener attachment means ATM2 that allows the body of the strap to attach to it and wrap around and move up until it covers the whole intended area. Importantly, the significant advantage of this unit is that the body of the strap is stretchable. This allows the adjacent moving muscles and tissues to flex and rest which otherwise with use of non-stretchable straps would not be possible. This is significant advantage in certain cases. The splints may be made from a single piece, a combination of two pieces or even more. Note the use of more than one support is shown in multiple figures such as the unit made for the shoulders, head and arm etc. and in FIGS. 11, 11 A, 16 A, 18,18 A and 19 and will not be repeated and an example of splint made of two pieces is shown in FIG. 1CD. This figure shows schematically the rear surface of a shaped support which has a relatively rigid body composed of two pieces, SUP-F, to be placed in the forearm and, SUP-H, for placement on the back of the hand, which are attached to each other on a detachable, re-attachable basis. The lower piece of this support SUP-H has a body with curvature such as a large spoon or spade. The upper piece SUP-F has a long rectangular shape almost like a handle of a spoon except with a curve to fit the elbow. They are attached to each other to make a unit in the shape of a large spoon or spade with curvatures to stand in posterior surfaces of forearm and hand and function as a splint. The support has a long zone of hook fastener attachment means shown at ATM2 on the rear surface of the pieces SUP-F and SUP-H. Also attached to the support is a long strap shown at STR-L, made from a stretchable, loop fastener attachment means with attachment means ATM1 zone on the rear surface of its first end and hook fastener attachment means ATM2 on the rear surface of its second end so that the first end with attachment means ATM1 will attach to the outer surface of the body of support SUP-H and can wrap around the support obliquely and move up wrapping to hold the support around the hand and the elbow securely, and the second end will attach to the outer surface of the strap itself. The advantages of this unit are many. It allows the size of the handle and main body of this support to be changed, since the hands of people have different sizes, or the needed padding may have different sizes. Thus having a model for everybody in hospital or emergency center is not possible or will be costly; however, this model allows two pieces of different sizes to be attached to each other for making a unit that would fit a given case.

It is very light, and it is very easy to handle and can be packed compact to be carried by users for potential circumstance, going to the woods, mountains, bike riding and in army. Note, the two pieces of the supports may be attached to each other by use of attachment means on a detachable re-attachable basis, as shown in FIG. 1CD where the lower end of the support SUP-F is attached to the rear surface of the support SUP-H by use of attachment means ATM2. It should be noted that that the support may also be used with more than one strap as shown in the units in FIG. 16 for the leg or in FIGS. 14 and 15 for the units for the arm and thigh. Advantages of the units with multiple straps are that they allow each strap to be easily adjusted, which is very important. Importantly, another unit of such support with a smaller size with a zone of hook fastener attachment means ATM2 on its outside surface may be also used, for being placed in the palm and on the anterior surface of the forearm so that this unit also allows a strap to wrap around in order to keep these two supports securely in front and back of the hand and forearm for more security if there is a broken bone involved that needs more support. Similar, units may be made for the foot, legs etc.

FIG. 1E shows another example of a shaped support, in which the support has the shape of a pocket shown at POC and will be pulled to the front of the feet. This will simplify the use significantly.

Some Explanation about the Straps.

The body of strap/s for the use with these supports has the following properties.

1. It can be any stretchable strap that is attached to the support, at its first end by a fixed or a detachable, re-attachable basis and in its second end has a zone of attachment means that allows it to be attached to the body of the support on a detachable, re-attachable basis. An example of this model is shown in FIGS. 4, 4A and 4B, 10, 11, 14, 16, 17 and similar.

2. The second type of straps which are used with these units is a stretchable fabric with a body that is also capable of attaching directly to another attachment means such as a hook-fastener attachment means ATM2 on a detachable, re-attachable basis, as shown in FIGS. 3 and 3A, 4C, 4D, 5, 6 and similar. This kind of strap has been introduced by this applicant to the USPTO previously and the example is made from Lyrca™ and in this application it is referred as STR-L. Importantly the support unit may use one or more bands of double-sided attachment means made from ATM2 referred to as DS-ATM2 shown in FIGS. 2 and 2A as explained earlier, so that this double-sided hook fastener attachment means DS-ATM2 can be attached to the outer surface of the support on a detachable, re-attachable basis, for use with the straps made from STR-L. An example of such modification of support is shown at FIGS. 4C and 4D. Such a model will allow.

A. The strap, STR-L to attach to the support by use of its end piece ATM2 on a detachable, re-attachable basis.

B. If the strap STR-L attaches to the zones of the ATM2 of the support directly, in any area that the ATM2, or the double sided attachment means are attached.

The free end of the straps, STR, may have the following options. 1. Having a zone of attachment means ATM2 for attaching to the support or the outer surface of the strap itself as shown in FIG. 7AB. 2. Having a rather large zone of attachment means ATM1 as shown in FIG. 8. 3. Having a large zone of attachment means ATM1, with bands of attachment means ATM2s as shown in FIG. 8. 4. Having, a zone of attachment means ATM2 on its lower surface as shown in FIGS. 7A, 7AB and many other figures. 5. Having a zone of attachment means ATM1 and hook fastener attachment means ATM2 next or close to each other in upper side as shown in FIG. 8. 6. Having a zone of attachment means ATM1 and attachment means ATM2 next or close to each other on its lower side as well as shown in FIGS. 8 and 8A. 7. Having zones of attachment means ATM2 in both upper and lower side of its end as shown in FIG. 7AB. 8. Having zones of attachment means ATM1 in both upper and lower sides of its ends. 9. The body of the strap to have multiple zones of attachment means ATM1 and attachment means ATM2 scattered on its upper surface in different sizes, shapes and locations. An example is shown at FIGS. 8 and 8A. The body of the strap to have multiple zones of attachment means ATM1 and attachment means ATM2 scattered on its lower surface, in different sizes and shapes. An example is shown at FIGS. 8 and 8A. Importantly, Please note that the size, numbers and locations of the zones of attachment means ATM1 and attachment means ATM2 in both upper and lower surfaces of the strap shown at FIGS. 8 and 8A may vary.

The above mentioned properties will provide multiple important options such as: the strap may attach to the support with use of one or more zones of attachment means ATM2. This will be possible when the support is covered with one type of attachment means such as a layer of attachment means ATM1. A similar strap may be attached to the end of the first strap, by using one zone of attachment means ATM1 to attach to the zone of attachment means ATM2 from the end of the second strap to elongate the combination. The second end of a strap, STR may also have the same options and options such as a zone of hook fastener attachment means ATM2 that allows the strap to be attached to the support on a detachable, re-attachable basis. The strap may have options for allowing its length to be adjusted so that the length of the strap can be shortened if desired, and to have options for allowing its length to be adjusted, so that the length of the strap can be lengthened if desired, by attaching a second strap as explained in the text. The length of strap may be adjusted by use of various D shaped rings, as commonly done in this age of science, so that the length of the strap can be shortened or lengthened if desired. Note the strap may attach to the support with use of one zone of attachment means ATM1 at its body—this is for the models which the support has a surface made of or has at least one zone of attachment means ATM2. The number and direction of the attachment and use of straps may vary, for example the unit may have one strap, it may have two straps or more, moving in one direction such as the unit shown at FIGS. 6, 9, 10, 10 A, 14, 15 and 16. Or they may come from the opposite side of the first strap as shown in FIG. 9B, which at times is easier to handle, for example when used by one hand. Also, strap may be attached vertically to the first strap as shown in FIG. 1F or 32. Also some straps may have lesser width and may be called as bands, such as the unit shown at FIGS. 10 and 10A.

Special Roles of Supports.

Please note these supports play many important roles, their first role being functioning as an stabilizer of the system, so that the straps will attach to the body of the support to be stable and not to slip, move down or fall. Second, it functions to make the placement and handling of the straps easier. An example of this is shown at FIG. 16. The main idea, explained in this text and previous inventions of this applicant, allows making multiple models of strap-support means for use in different areas of the body. These also include units for control bleeding or extravasations of fluids by strangulation of the limbs, as well as introducing units that guard the wound site as shown in FIGS. 25 and 26. Also, means are introduced that help in preventing ulcerations in areas by controlling the pressure in a limb, such as the lower legs and ankles, such units being shown at FIGS. 21, 22 and 22A. Models are shown for use in patients who have vascular problems with extravasations of intravascular fluid inside the tissue as shown in FIGS. 16, 16A, 16B and 16C, the models shown in these figures allowing the wound in the ankles and legs to be squeezed to prevent and reduce tissue swelling. In previous applications, this applicant shows means that allow a limb to be elevated for a better drainage. All in all, the applicant tries to introduce units for improving human and animal life.

Some More Explanation about the Straps.

Body of the straps may be made from.

S1. A stretchable fabric or material that has zones of loop fastening attachment means ATM1 or hook fastening attachment means ATM2 on them, such as one example with attachment means ATM2 on its rear surface as shown in FIGS. 4 and 4A; this zone/s may be localized only at the end of the strap or the strap may have multiple zones of attachment means attached to the surface or embedded to the body of the strap either on one surface of the strap or on both surfaces, as shown in FIGS. 8 and 8A.

S2. Importantly, the other generation of stretchable straps may be used which functions also as a loop fastener attachment means ATM1 as shown at FIGS. 3, 3A, 7 and 7A, at STR-L. Note the lower surface of the strap which has capability of functioning as loop fastener attachment means is shown at ATM1, at FIG. 7A. Importantly, note in practice the applicant has used fabric Lycra™ which in at least in some models provides both surfaces functioning as loop fastener attachment means, as shown in FIG. 3, although one surface has this property more than the other—he refers to this type of strap as STR-L. Thus it allows the end of the strap with attachment means ATM2 on its rear to wrap around and attach to the outer surface of the strap STR-L on a detachable, re-attachable basis. The body of these straps can be further fortified by having zones of loop fastening attachment means ATM1 and/or hook fastening attachment means ATM2 on it. The addition of hook fastener attachment means ATM1 is to fortify the attachment of the attachment means ATM2 to it. These zones may be localized only at the end of the strap or the strap may have multiple zones of attachment means of either kind attached to the surface or embedded to the body of the strap either on one surface of the strap or on both surfaces. An example of this is shown at FIGS. 8 and 8A.

S3. The stretchable fabric may be modified to have both of its surfaces function as more potent loop fastener attachment means, ATM1, as shown in FIG. 3A, and in FIG. 7AB at STR-L, where both the upper and the lower surfaces of the strap have the capability of functioning as loop fastener attachment means shown at ATM1. This kind of fabric may be made either by manufacturing such material, or by sewing together pieces of the presently available, Lycra™ fabric back to back so that opposite strap surfaces that have more capability of the ATM1 will function as the stretchable fabric and provide more potent loop fastener attachment means ATM1. Such a fabric then can be further fortified by having zones of hook and/or loop fastening attachment means on it similar to the model shown at FIGS. 8 and 8A. These zones may be localized only at the end of the strap or the strap may have multiple zones of attachment means of either kind attached to the surface or embedded to the body of the strap either on one surface of the strap or on both of its surfaces. Note importantly and in other words the strap means made from a material such as Lycra™, will directly attach to the zones of hook attachment means ATM2 of the support on a detachable, re-attachable attachment basis. This makes a very valuable unit that allows the attachment of a such strap means, with end piece or zones of hook-fastener attachment means, ATM2, to occur on a double-function basis as follows:

1. The zones of the hook-fastener attachment means, ATM2, from the ends of the strap will attach to the outer surface of the Type I support, SUP-1 on a detachable, re-attachable basis.

2. The body of such strap means, made from a loop-fastener attachment means, ATM1, will also attach to the zones of the hook-fastener attachment means, ATM2, located on the support, SUP-1 on a detachable, re-attachable basis as well. This is the reason why a double-attachment occurs that is very useful since allows a very easy and comfortable use of such straps in many models of these units. Since the attachment of the strap to the ATM2 of support will keep the strap stable and allows the user to attach the end of the strap to the outer surface of the support on a more controlled and comfortable fashion and in a location that fits, very Importantly, at this point the strap may be pulled more or less to fit the surface of the support.

Straps with Special End Pieces.

Some straps may have special end pieces for the reason of being handled easily or for other reasons; one such example is shown at FIG. 4B. In this model the end of the strap in the right side has a non-stretchable end piece, shown at END-P that allows it to be grabbed easily and to allow this piece to attach to the support unit. For this purpose this end piece has one or more zones of hook fastener attachment means shown as ATM2-1R and ATM2-2R which are located in its rear surface of this end piece. These may be sewn or, the attached to these units. The importance of these end pieces is that based on the research of the applicant, having two attachment means in this end piece will make it more easy or controllable to attach it to a support, since having the support on limb and wrapping the strap around the limb, first the attachment means ATM 2-1R will attach to the support and will keep the strap secure and then second, the attachment means ATM2-2R will be attached to the support again on a detachable, re-attachable basis, allowing a more easy placement. Note also the size and different variables of these units may vary. Similar end pieces are also shown at FIG. 16.

Importantly, these end pieces, may have a body the same as the support and the hook attachment means may be a double-sided attachment means. Importantly, note that the end pieces with two attachment means ATM2 are valuable mostly, when the strap does not have the capability of attaching to the ATM2 itself, since when the body of the strap is the STR-L, the strap will attach itself to the attachment means ATM2 of the support and will be secured before the zone of the attachment means ATM2 at its rear end attaches to the support.

Control of the length of the straps. The length of these straps may be controlled by various means and methods such as:

1. By cutting the end and attaching attachment means to the desired area of the strap. This may be done by use of pieces shown in FIGS. 34, 34A, 35 and 35A.
2. Use of D-rings so that the length of the strap can be controlled. The end piece of the strap, after passing through the D-ring, will make a U turn and be attached to the body of the strap by use of various means, such as adhesives, attachment means of various kinds, sewing etc. The D-Rings are shown in FIGS. 13 and 38.
3. Adding another extension piece of straps to the existing ones. In this model the end of one strap will have attachment means ATM1 and the other strap with end of attachment means ATM2, so that they can attach to each other on a detachable, re-attachable basis.
4. Use of adhesives, attachment means, means that can be used to cut and paste all can be used in order to modify the length of these units as shown at FIGS. 37 and 37 A.
5. Using the extension unit shown at FIG. 38.
6. Custom making is also a method that allows the proper length of strap to be made.

Importantly, please note that the basic unit is using a support means which has an outer layer covered, or at least with a zone of attachment means, to allow a stretchable strap means with one or more zones of attachment means capable of attaching to the outer surface of the support to be attached to it on a detachable, re-attachable basis. This basic idea and model can be modified for use in different areas and with versions which this applicant has previously introduced to the USPTO. Thus these teachings will allow making many different models for use in areas such as hips, elbows, knees, ankles, chest, legs, and head and in any other areas that may be applied.

Importantly, please note that the explanation about this model and figures can be applied for all the other models and figures which are presented in this application, in figure format or the text as applicable. Thus specifically each model that is shown in previous applications and this application can be modified to use a support made from a non-stretchable attachment means. Thus in some of those models adding a double-sided attachment means ATM2 may complement the unit. Thus again and specifically many of these models may be made with a loop fastener support attached to strap means which has an end means with one or more zones of hook fastening attachment means which is capable of attaching to the outer surface of the support on a detachable, re-attachable attachment basis. Also importantly, the sizes, the shapes, configurations, relative sizes, thickness, the materials and all other important specifications of these units may be modified for using different units. Also importantly, note that this applicant believes both, the stretchable fabric and the attachment means ATM2's may be modified to make these units such to attach to each other with significant affinity in both sides of the straps.

The invention claimed is:

1. A wrap for encircling a portion of a living body, the wrap comprising:
a strap, which has a length and which comprises an inner surface, an outer surface, and stretchable material allowing the strap to stretch along its length, for wrapping at least once around a portion of a living body, the stretchable material having an outer surface of loop attachment material, the strap further comprising a zone of hook attachment material disposed on the inner surface of the strap at a location along the length of the strap which provides for detachable/reattachable attachment of the hook attachment material to the loop attachment material of the outer surface of the stretchable material,
in which the stretchable material has an inner surface of loop attachment material, and the strap further comprises a zone of hook attachment material disposed on the outer surface of the strap at a location along the length of the strap which provides for detachable/reattachable attachment of the hook attachment material disposed on the outer surface of the strap to the loop attachment material of the inner surface of the stretchable material.

2. The wrap as set forth in claim 1 in which the strap comprises multiple zones of hook attachment material disposed on the outer surface of the strap at different locations along the length of the strap which provide for detachable/reattachable attachment of the multiple zones of hook attachment material disposed on the outer surface of the strap to the loop attachment material of the inner surface.

3. The wrap as set forth in claim 2 in which the strap comprises multiple zones of hook attachment material disposed on the inner surface of the strap at different locations along the length of the strap which provide for detachable/reattachable attachment of the multiple zones of hook attachment material disposed on the inner surface of the strap to the loop attachment material of the outer surface of the stretchable material.

4. A wrap for encircling a portion of a living body, the wrap comprising:
- a strap, which has a length and which comprises an inner surface, an outer surface, and stretchable material allowing the strap to stretch along its length, for wrapping at least once around a portion of a living body, the stretchable material having an outer surface of loop attachment material, the strap further comprising a zone of hook attachment material disposed on the inner surface of the strap at a location along the length of the strap which provides for detachable/reattachable attachment of the hook attachment material to the loop attachment material of the outer surface of the stretchable material,
- further comprising a support for placement against a portion of a living body, the support comprising a support body, the strap comprising a first lengthwise end attached to the support body, and the zone of hook attachment material disposed on the inner surface of the strap being at a location along the length of the strap spaced from the strap end which is attached to the support body.

5. The wrap as set forth in claim 4 in which the strap comprises a second lengthwise end opposite the first lengthwise end and the zone of hook attachment material disposed on the inner surface of the strap is disposed proximate the second lengthwise end of the strap.

6. The wrap as set forth in claim 5 in which the support body has a shape for conforming to a surface shape of a portion of a living body.

7. The wrap as set forth in claim 6 in which the support body has a shape for conforming to a surface shape of a limb of a living body.

8. The wrap as set forth in claim 7 in which the strap length is long enough to provide for convolutions of the wrap to overlap each other.

9. The wrap as set forth in claim 8 in which the strap comprises multiple zones of hook attachment material disposed on the inner surface of the strap at different locations along the length of the strap which provide for detachable/reattachable attachment of the multiple zones of hook attachment material disposed on the inner surface of the strap to the loop attachment material of the outer surface of the stretchable material.

10. The wrap as set forth in claim 9 in which the strap and the at least one additional strap extend lengthwise away from the support body in the same direction.

11. The wrap as set forth in claim 9 in which the strap and the at least one additional strap extend lengthwise away from the support body in opposite directions.

12. The wrap as set forth in claim 5 further comprising at least one additional strap having a first end attached to the support body and comprising material which is lengthwise stretchable for wrapping at least once around a portion of a living body and has an outer surface comprising loop attachment material, the at least one additional strap further comprising a zone of hook attachment material disposed on an inner surface at a location along the length of the strap which provides for detachable/reattachable attachment of the hook attachment material disposed on the inner surface of the at least one additional strap to loop attachment material of the at least one additional strap.

13. A wrap for encircling a portion of a living body, the wrap comprising:
- A) a support means having an outer face completely covered by attachment means; and
- B) a stretchable strap means having a first end portion attached to and extending from the support means and a second end portion having an inner face comprising both loop attachment material and hook attachment material for detachable, re-attachable attachment to the attachment means covering the outer face of the support means.

14. A wrap as set forth in claim 13 in which the attachment means covering the outer face of the support means comprises a zone of hook attachment material disposed for detachable, re-attachable attachment to the loop attachment material of the second end portion of the strap means and a zone of loop attachment material disposed for detachable, re-attachable attachment to the hook attachment material of the second end portion of the strap means.

15. A wrap as set forth in claim 14 in which the loop attachment material of the second end portion of the strap means is a surface of stretchable material in the strap means.

16. A wrap as set forth in claim 15 in which the support means comprises multiple support pieces having detachable, re-attachable attachment to each other.

17. A wrap as set forth in claim 16 in which the zone of hook attachment material on the outer face of the support means is disposed on two of the multiple support pieces.

18. A wrap as set forth in claim 16 in which the stretchable material of the strap means comprises an outer surface of loop attachment material to which the hook attachment material of the second end portion of the strap means can detachably, re-attachably attach.

* * * * *